US010835586B2

(12) United States Patent
Mahr et al.

(10) Patent No.: US 10,835,586 B2
(45) Date of Patent: Nov. 17, 2020

(54) PEPTIDES AND COMBINATION OF PEPTIDES AND SCAFFOLDS FOR USE IN IMMUNOTHERAPY AGAINST RENAL CELL CARCINOMA (RCC) AND OTHER CANCERS

(71) Applicant: Immatics Biotechnologies GmbH, Tuebingen (DE)

(72) Inventors: Andrea Mahr, Tuebingen (DE); Toni Weinschenk, Aichwald (DE); Oliver Schoor, Tuebingen (DE); Jens Fritsche, Dusslingen (DE); Harpreet Singh, Munich (DE); Colette Song, Ostfildern (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days.

(21) Appl. No.: 16/715,846

(22) Filed: Dec. 16, 2019

(65) Prior Publication Data

US 2020/0147190 A1    May 14, 2020

Related U.S. Application Data

(63) Continuation of application No. 16/367,790, filed on Mar. 28, 2019, now Pat. No. 10,548,958, which is a continuation of application No. 16/212,787, filed on Dec. 7, 2018, now Pat. No. 10,314,899, which is a continuation of application No. 15/978,700, filed on May 14, 2018, now Pat. No. 10,213,498, which is a continuation of application No. 15/799,495, filed on Oct. 31, 2017, now Pat. No. 10,105,428, which is a continuation of application No. 15/082,920, filed on Mar. 28, 2016, now Pat. No. 9,931,388.

(60) Provisional application No. 62/140,767, filed on Mar. 31, 2015.

(51) Int. Cl.
| | |
|---|---|
| *A61K 39/00* | (2006.01) |
| *G16B 25/00* | (2019.01) |
| *C07K 14/47* | (2006.01) |
| *A61P 35/00* | (2006.01) |
| *A61K 35/17* | (2015.01) |
| *C07K 16/18* | (2006.01) |
| *C12N 5/0783* | (2010.01) |
| *C12N 15/115* | (2010.01) |
| *C07K 14/74* | (2006.01) |
| *C07K 16/28* | (2006.01) |
| *C07K 16/30* | (2006.01) |
| *A61K 35/12* | (2015.01) |
| *C07K 14/705* | (2006.01) |

(52) U.S. Cl.
CPC .......... *A61K 39/0011* (2013.01); *A61K 35/17* (2013.01); *A61K 39/001102* (2018.08); *A61P 35/00* (2018.01); *C07K 14/4748* (2013.01); *C07K 14/70539* (2013.01); *C07K 16/18* (2013.01); *C07K 16/2833* (2013.01); *C07K 16/3038* (2013.01); *C12N 5/0636* (2013.01); *C12N 15/115* (2013.01); *G16B 25/00* (2019.02); *A61K 2035/124* (2013.01); *A61K 2039/505* (2013.01); *A61K 2039/5158* (2013.01); *A61K 2039/572* (2013.01); *C07K 14/705* (2013.01); *C07K 2317/73* (2013.01); *C07K 2317/76* (2013.01); *C07K 2319/33* (2013.01); *C07K 2319/55* (2013.01); *C12N 2310/16* (2013.01)

(58) Field of Classification Search
None
See application file for complete search history.

(56) References Cited

U.S. PATENT DOCUMENTS

| | | | |
|---|---|---|---|
| 6,934,639 B1 | 8/2005 | Chen et al. | |
| 7,368,548 B2 | 5/2008 | Dahary et al. | |
| 7,569,662 B2 | 8/2009 | Pollock et al. | |
| 7,667,001 B1 | 2/2010 | Pollock et al. | |
| 7,705,120 B2 | 4/2010 | Lillie et al. | |
| 8,008,431 B2 * | 8/2011 | Weinschenk | A61P 35/00 530/300 |
| 8,080,634 B2 | 12/2011 | Singh et al. | |

(Continued)

FOREIGN PATENT DOCUMENTS

| | | |
|---|---|---|
| EP | 1 760 089 A1 | 3/2007 |
| WO | 1998/014466 A1 | 4/1998 |

(Continued)

OTHER PUBLICATIONS

Exhibit A (https://www.genecards.org/cgi-bin/carddisp.pl?gene=EGLN3).*

(Continued)

*Primary Examiner* — Nelson B Moseley, II
(74) *Attorney, Agent, or Firm* — McBee Moore & Vanik IP, LLC

(57) ABSTRACT

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

23 Claims, 21 Drawing Sheets
(15 of 21 Drawing Sheet(s) Filed in Color)
Specification includes a Sequence Listing.

(56) References Cited

U.S. PATENT DOCUMENTS

| | | |
|---|---|---|
| 8,323,657 B2 | 12/2012 | Nishimura |
| 8,323,906 B2 | 12/2012 | Veiby et al. |
| 8,586,006 B2 | 11/2013 | Hood et al. |
| 8,669,230 B2 | 3/2014 | Singh et al. |
| 9,511,128 B2 | 12/2016 | Singh et al. |
| 9,943,579 B2 | 4/2018 | Weinschenk et al. |
| 9,950,048 B2 | 4/2018 | Singh et al. |
| 10,071,148 B2 | 9/2018 | Weinschenk et al. |
| 2005/0106644 A1 | 5/2005 | Cairns |
| 2007/0037165 A1 | 2/2007 | Venter |
| 2007/0264651 A1 | 11/2007 | Agate et al. |
| 2009/0221509 A1 | 9/2009 | Rammensee et al. |
| 2009/0274714 A1 | 11/2009 | Singh et al. |
| 2010/0029573 A1 | 2/2010 | Weinschenk et al. |
| 2010/0099111 A1 | 4/2010 | Challita-Eid et al. |
| 2011/0070253 A1 | 3/2011 | Rammensee et al. |
| 2016/0168200 A1 | 6/2016 | Weinschenk et al. |
| 2019/0076476 A1 | 3/2019 | Weinschenk et al. |

FOREIGN PATENT DOCUMENTS

| | | | | |
|---|---|---|---|---|
| WO | 2004/048599 A2 | 6/2004 | | |
| WO | 2004/085461 A2 | 10/2004 | | |
| WO | 2007/114954 A2 | 10/2007 | | |
| WO | WO 2007/119515 | * 10/2007 | ............. | C12N 15/00 |
| WO | 2009/015842 A2 | 2/2009 | | |
| WO | 2010102262 A1 | 9/2010 | | |
| WO | 2012162468 A1 | 11/2012 | | |
| WO | 2013151668 A2 | 10/2013 | | |
| WO | 2015/018805 A1 | 2/2015 | | |
| WO | WO 2015/018805 | * 2/2015 | ............. | A61K 38/17 |

OTHER PUBLICATIONS

Dannenmann et al., "Spontaneous Peripheral T-cell Responses toward the Tumor-Associated Antigen Cyclin D1 in Pantients with Clear Cell Renal Cell Carcinoma" Cancer Immunology Research. (Nov. 2013) vol. 1, No. 5: 288-295.

Krueger et al., "Lessons to be learned from primary renal cell carcinomas: novel tumor antigens and HLA ligands for immnothrapy" Cancer Immunology Immunothereapy. (2005) vol. 54: 826-836.

Search Report dated Dec. 30, 2015, issued in counterpart Great Britain application No. 1505585.8.

Kramer B F et al., MAGED4-expression in renal cell carcinoma and identification of an HLA-A*25-restricted MHC class I ligand from solid tumor tissue, Cancer Biology & Therapy, Landes Bioscience, US, vol. 4, No. 9, Sep. 1, 2005, pp. 943-948.

Krueger, Tobia et al., Lessons to be learned from primary renal cell carcinomas: novel tumor antigens and HLA ligands for immunotherapy, Cancer Immunology, Immunotherapy, Springer, Berlin, DE, vol. 54, No. 9, pp. 826-836.

Weinschenk, Toni et al., Integrated functional genomics approach for the design of patient-individual antitumor vaccines, Cancer Research, American Association for Cancer Research, US, vol. 62, No. 20, Oct. 15, 2002, pp. 5818-5827.

International Search Report for PCT/EP2016/056601, dated Aug. 3, 2016.

Yee et al., "Adoptive T cell therapy using antigen-specific CD8+ T cell clones for the treatment of patients with metastatic melanoma: In vivo persistence, migration, and antitumor effect of transferred T cells", PNAS, Dec. 10, 2002, pp. 16168-16173, vol. 99, No. 25.

* cited by examiner

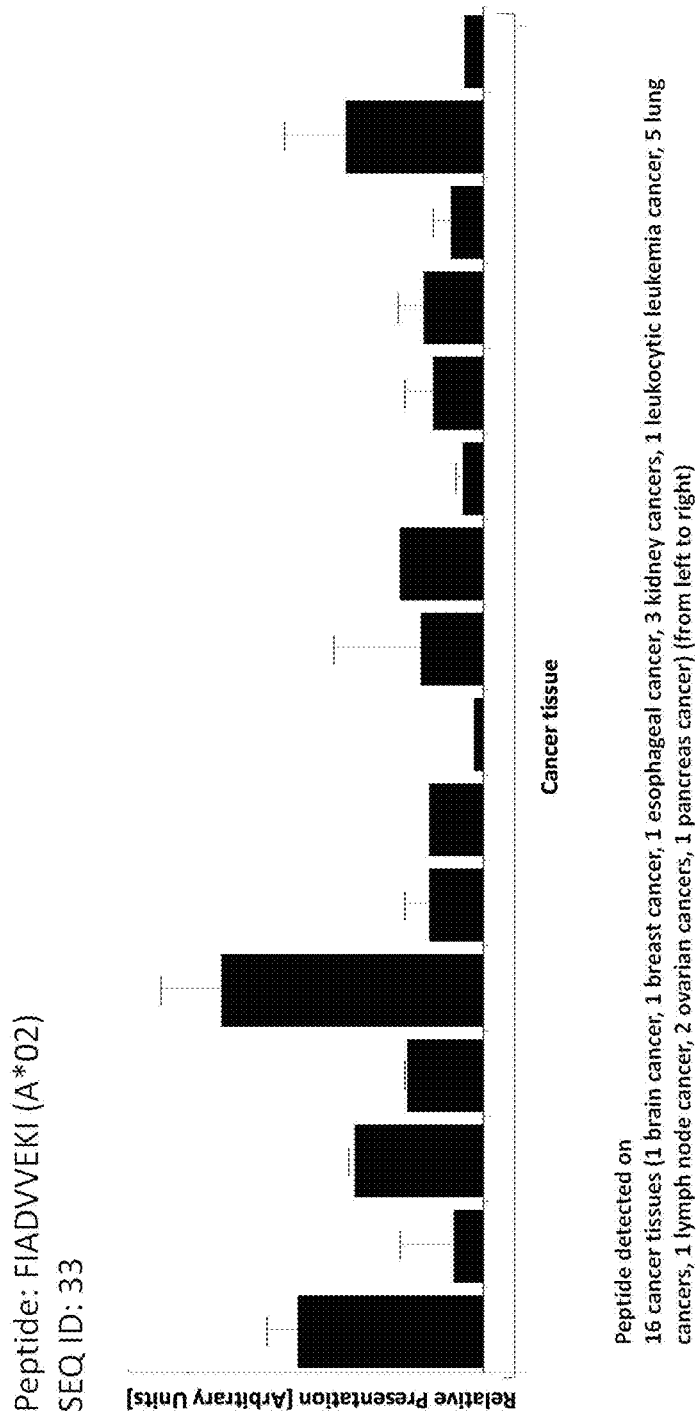

PEPTIDES AND COMBINATION OF PEPTIDES AND SCAFFOLDS FOR USE IN IMMUNOTHERAPY AGAINST RENAL CELL CARCINOMA (RCC) AND OTHER CANCERS

CROSS REFERENCE TO RELATED APPLICATIONS

This application is a continuation of U.S. patent application Ser. No. 16/367,790, filed Mar. 28, 2019, which is a continuation of U.S. patent application Ser. No. 16/212,787, filed Dec. 7, 2018, now U.S. Pat. No. 10,314,899, issued Jun. 11, 2019, which is a continuation of U.S. patent application Ser. No. 15/978,700, filed May 14, 2018, now U.S. Pat. No. 10,213,498, issued Feb. 26, 2019, which is a continuation of U.S. patent application Ser. No. 15/799,495, filed Oct. 31, 2017, now U.S. Pat. No. 10,105,428, issued Oct. 23, 2018, which is a continuation of U.S. patent application Ser. No. 15/082,920, filed Mar. 28, 2016, now U.S. Pat. No. 9,931,388, issued Apr. 3, 2018, which claims the benefit of U.S. Provisional Application No. 62/140,767, filed Mar. 31, 2015, and Great Britain Application No. 1505585.8, filed Mar. 31, 2015, the content of each these applications is herein incorporated by reference in their entirety.

REFERENCE TO SEQUENCE LISTING SUBMITTED AS A COMPLIANT ASCII TEXT FILE (.TXT)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2912919-043011.txt," created on 13 Dec. 2019, and 23,936 bytes in size) is submitted concurrently with the instant application, and the entire contents of the Sequence Listing are incorporated herein by reference.

FIELD

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

The present invention relates to several novel peptide sequences and their variants derived from HLA class I molecules of human tumor cells that can be used in vaccine compositions for eliciting anti-tumor immune responses, or as targets for the development of pharmaceutically/immunologically active compounds and cells.

BACKGROUND OF THE INVENTION

Kidney cancer is more common in men than women and is the ninth most common cancer in men (214 000 cases) and the 14th most common in women (124 000 cases) worldwide in 2012. 70% of the new cases occurred in countries with high and very high levels of human development, with 34% of the estimated new cases in Europe and 19% in North America. There were an estimated 143 000 deaths from kidney cancer in 2012 (91 000 in men, 52 000 in women); kidney cancer is the 16th most common cause of death from cancer worldwide.

The highest incidence rates are found in the Czech Republic. Elevated rates are also found in northern and Eastern Europe, North America, and Australia. Low rates are estimated in much of Africa and East Asia. The case fatality rate is lower in highly developed countries (overall mortality-to-incidence ratio, 0.4) than in countries with low or medium levels of human development (0.5). Only 3.1% of the cases were diagnosed in Africa, but 5.7% of the deaths occurred in this region. Incidence and mortality rates have been increasing in many countries, across different levels of human development (World Cancer Report, 2014).

Most renal cancers are renal cell carcinomas (RCC), a heterogeneous class of tumors arising from different cell types within the renal parenchyma. Most are clear cell renal carcinomas (about 70% of renal cancer cases), followed by papillary (10-15%), chromophobe (about 5%), and collecting duct (<1%) renal cell carcinomas. Each of these renal cell tumor subtypes has distinct genetic characteristics (Moch, 2013; World Health Organization Classification of Tumours, 2004).

Renal cell carcinoma (RCC) is characterized by a lack of early warning signs, diverse clinical manifestations, and resistance to radiation and chemotherapy. A total of 25-30% patients with RCC initially present with overt metastases (Hofmann et al., 2005). About one third of patients with RCC will develop metastatic disease over time. Thus, nearly 50-60% of all patients with RCC will eventually present with metastatic disease (Bleumer et al., 2003; Hofmann et al., 2005). Among those with metastatic disease, approximately 75% have lung metastases, 36% lymph node and/or soft tissue involvement, 20% bone involvement, and 18% liver involvement (Sachdeva et al., 2010).

RCC patients with metastatic disease receiving cytokine-based first-line systemic therapy can be categorized into risk groups predictive for survival based on 5 prognostic factors (Motzer et al., 2004). Pre-treatment features associated with a shorter survival were low Karnofsky Performance Status (<80%), high serum lactate dehydrogenase (>1.5 ULN), low hemoglobin (<LLN), high corrected serum calcium (>10 mg/dL), and time from diagnosis to treatment <1 year. Based on these risk factors, patients were categorized into three risk groups. The median time to death in the 18% of patients with zero risk factors (favorable-risk) was 30 months. 62% of the patients had one or two risk factors (intermediate risk), and the median survival time in this group was 14 months. Patients with 3 or more risk factors (poor risk) who comprised 20% of the patients, had a median survival time of 5 months. The application of this MSKCC risk group categorization has been widely applied in clinical trials for advanced RCC. Risk categorization can be used for planning and interpreting the results of clinical trials and directing therapy.

Risk factors for RCC are cigarette smoking and obesity. Different meta-analyses confirmed that ever-smoking increases the risk of renal cancer compared with never-smoking (Cho et al., 2011; Hunt et al., 2005). There is also a dose-dependent increase in risk related to the number of cigarettes smoked per day. Risk decreases in the 5-year period after smoking cessation. Overweight, especially obesity, is a risk factor for renal cancer in both women and men (Ljungberg et al., 2011). The proportion of all cases of renal cancer attributable to overweight and obesity has been estimated to be about 40% in the USA and up to 40% in European countries (Renehan et al., 2008; Renehan et al., 2010). The mechanisms by which obesity influences renal carcinogenesis are unclear. Sex steroid hormones may affect renal cell proliferation by direct endocrine receptor-mediated effects. Obesity with the combined endocrine disorders, such as decreased levels of sex hormonebinding globulin and progesterone, insulin resistance, and increased levels of growth factors such as insulin-like growth factor 1 (IGF-1), may contribute to renal carcinogenesis. Recently, a case-control study has reported a stronger association of clear cell carcinoma with obesity (World Cancer Report, 2014).

Initial treatment is most commonly either partial or complete removal of the affected kidney(s) and remains the mainstay of curative treatment (Rini et al., 2008). For first-line treatment of patients with poor prognostic score a guidance elaborated by several cancer organizations and societies recommend the receptor tyrosine kinase inhibitors (TKIs) sunitinib (Sutent®) and pazopanib (Votrient®), the monoclonal antibody bevacizumab (Avastin®) combined with interferon-α (IFN-α) and the mTOR inhibitor temsirolimus (Torisel®). Based on guidelines elaborated by the US NCCN as well as the European EAU and ESMO, the TKIs sorafenib, pazopanib or recently axitinib are recommended as second-line therapy in RCC patients who have failed prior therapy with cytokines (IFN-α, IL-2). The NCCN guidelines advise also sunitinib in this setting (high-level evidence according to NCCN Category I).

Everolimus and axitinib are recommended as second-line therapy of those patients who have not benefited from a VEGF-targeted therapy with TKIs according to the established guidelines.

The known immunogenity of RCC has represented the basis supporting the use of immunotherapy and cancer vaccines in advanced RCC.

The interesting correlation between lymphocytes PD-1 expression and RCC advanced stage, grade and prognosis, as well as the selective PD-L1 expression by RCC tumor cells and its potential association with worse clinical outcomes, have led to the development of new anti PD-1/PD-L1 agents, alone or in combination with anti-angiogenic drugs or other immunotherapeutic approaches, for the treatment of RCC (Massari et al., 2015).

In advanced RCC, a phase III cancer vaccine trial called TRIST study evaluates whether TroVax (a vaccine using a tumor-associated antigen, 5T4, with a pox virus vector), added to first-line standard of care therapy, prolongs survival of patients with locally advanced or mRCC. Median survival had not been reached in either group with 399 patients (54%) remaining on study however analysis of the data confirms prior clinical results, demonstrating that TroVax is both immunologically active and that there is a correlation between the strength of the 5T4-specific antibody response and improved survival. Further there are several studies searching for Peptide vaccines usind Epitopes being over-expressed in RCC.

Variuos approaches of tumor vaccines have been under investigation. Studies using whole-tumor approaches, including tumor cell lysates, fusions of dendritic cells with tumor cells, or whole-tumor RNA were done in RCC patients, and remissions of tumor lesions were reported in some of thesetrials (Avigan et al., 2004; Holtl et al., 2002; Marten et al., 2002; Su et al., 2003; Wittig et al., 2001).

In the last years, several human TAAs expressed in RCCs and recognized by antigen-specific CTLs have been defined and characterized using expression cloning, reverse immunology approach, or by applying DNA microarray technology (Dannenmann et al., 2013; Michael and Pandha, 2003; Minami et al., 2014; Renkvist et al., 2001; Wierecky et al., 2006).

Considering the severe side-effects and expense associated with treating cancer, there is a need to identify factors that can be used in the treatment of cancer in general and RCC in particular. There is also a need to identify factors representing biomarkers for cancer in general and RCC in particular, leading to better diagnosis of cancer, assessment of prognosis, and prediction of treatment success.

Immunotherapy of cancer represents an option of specific targeting of cancer cells while minimizing side effects. Cancer immunotherapy makes use of the existence of tumor associated antigens.

The current classification of tumor associated antigens (TAAs) comprises the following major groups:

a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members and NY-ESO-1.

b) Differentiation antigens: These TAAs are shared between tumors and the normal tissue from which the tumor arose. Most of the known differentiation antigens are found in melanomas and normal melanocytes. Many of these melanocyte lineage-related proteins are involved in biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anticancer response by breaking previously established tolerance. Prominent examples for this class of TAAs are Her-2/neu, survivin, telomerase, or WT1.

d) Tumor-specific antigens: These unique TAAs arise from mutations of normal genes (such as β-catenin, CDK4, etc.). Some of these molecular changes are associated with neoplastic transformation and/or progression. Tumor-specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor-(-associated) exon in case of proteins with tumor-specific (-associated) isoforms.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

T-cell based immunotherapy targets peptide epitopes derived from tumor-associated or tumor-specific proteins, which are presented by molecules of the major histocompatibility complex (MHC). The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides.

MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation in the literature (Brossart and Bevan, 1997; Rock et al., 1990). MHC class II molecules can be found predominantly on professional antigen presenting cells (APCs), and primarily present peptides of exogenous or transmembrane proteins that are taken up by APCs e.g. during endocytosis, and are subsequently processed.

Complexes of peptide and MHC class I are recognized by CD8-positive T cells bearing the appropriate T-cell receptor (TCR), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T-cell epitopes derived from tumor associated antigens (TAA) is of great importance for the development of pharmaceutical products for triggering anti-tumor immune responses (Gnjatic et al., 2003). At the tumor site, T helper cells, support a cytotoxic T cell- (CTL-) friendly cytokine milieu (Mortara et al., 2006) and attract effector cells, e.g. CTLs, natural killer (NK) cells, macrophages, and granulocytes (Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006).

Elongated (longer) peptides of the invention can act as MHC class II active epitopes.

T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T cells are sufficient for inhibiting manifestation of tumors via inhibition of angiogenesis by secretion of interferon-gamma (IFNγ) (Beatty and Paterson, 2001; Mumberg et al., 1999). There is evidence for CD4 T cells as direct anti-tumor effectors (Braumuller et al., 2013; Tran et al., 2014a).

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1).

Since both types of response, CD8 and CD4 dependent, contribute jointly and synergistically to the anti-tumor effect, the identification and characterization of tumor-associated antigens recognized by either CD8+ T cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-class-I-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T cells bearing specific T cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to their function, e.g. in cell cycle control or suppression of apoptosis. Additionally, downstream targets of the proteins directly causative for a transformation may be up-regulated und thus may be indirectly tumor-associated. Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor associated antigen, leads to an in vitro or in vivo T-cell-response.

Basically, any peptide able to bind an MHC molecule may function as a T-cell epitope. A prerequisite for the induction of an in vitro or in vivo T-cell-response is the presence of a T cell having a corresponding TCR and the absence of immunological tolerance for this particular epitope.

Therefore, TAAs are a starting point for the development of a T cell based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and the immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of targeting peptide-MHC by specific TCRs (e.g. soluble TCRs) and antibodies or other binding molecules (scaffolds) according to the invention, the immunogenicity of the underlying peptides is secondary. In these cases, the presentation is the determining factor.

SUMMARY OF THE INVENTION

In a first aspect of the present invention, the present invention relates to a peptide comprising an amino acid sequence selected from the group consisting of SEQ ID NO: 1 to SEQ ID NO: 114 or a variant sequence thereof which is at least 77%, preferably at least 88%, homologous (preferably at least 77% or at least 88% identical) to SEQ ID NO: 1 to SEQ ID NO: 114, wherein said variant binds to MHC and/or induces T cells cross-reacting with said peptide, or a pharmaceutical acceptable salt thereof, wherein said peptide is not the underlying full-length polypeptide.

The present invention further relates to a peptide of the present invention comprising a sequence that is selected from the group consisting of SEQ ID NO: 1 to SEQ ID NO: 114 or a variant thereof, which is at least 77%, preferably at least 88%, homologous (preferably at least 77% or at least 88% identical) to SEQ ID NO: 1 to SEQ ID NO: 114, wherein said peptide or variant thereof has an overall length of between 8 and 100, preferably between 8 and 30, and most preferred of between 8 and 14 amino acids.

The following tables show the peptides according to the present invention, their respective SEQ ID NOs, and the prospective source (underlying) genes for these peptides. All peptides in Table 1 and Table 2 bind to HLA-A*02. The peptides in Table 2 have been disclosed before in large listings as results of high-throughput screenings with high error rates or calculated using algorithms, but have not been associated with cancer at all before. The peptides in Table 3 are additional peptides that may be useful in combination with the other peptides of the invention. The peptides in Tables 4A and B are furthermore useful in the diagnosis and/or treatment of various other malignancies that involve an over-expression or over-presentation of the respective underlying polypeptide.

TABLE 1

Peptides according to the present invention

| SEQ ID No | Sequence | Gene ID(s) | Official Gene Symbol(s) |
|---|---|---|---|
| 1 | ALIVSLPYL | 10786 | SLC17A3 |
| 2 | ILWREVVTL | 3299 | HSF4 |
| 3 | RLLGEVQAL | 3299 | HSF4 |
| 4 | FLSQDIITV | 5972 | REN |
| 5 | YLYPNLTRL | 6540 | SLC6A13 |
| 6 | VLFELSKTV | 23250 | ATP11A |
| 7 | FLLSLIDRL | 112399 | EGLN3 |
| 8 | GLASFKSFL | 8490 | RGS5 |
| 9 | ILLQKPDSV | 8490 | RGS5 |
| 10 | KLLQNNYGL | 8490 | RGS5 |
| 11 | FIQTEAPKEV | 8490 | RGS5 |
| 12 | ALDPSGNQLI | 54437 | SEMA5B |
| 13 | KIMAQILTV | 120892 | LRRK2 |
| 14 | ALLTETIFL | 120892 | LRRK2 |
| 15 | ILIKHLVKV | 143872 | ARHGAP42 |
| 16 | FMPEELPQL | 55258 | THNSL2 |
| 17 | ILAQQVHAL | 113220 | KIF12 |
| 18 | YVLDLAAKV | 47 | ACLY |
| 19 | LLDPGSLQL | 646658 | SYNDIG1L |
| 20 | AVANTTFTV | 80270 | HSD3B7 |
| 21 | RLIQGDQILSV | 10207 | INADL |
| 22 | FLSPPLPSV | 593, 641649 | BCKDHA, TMEM91 |
| 23 | YIQEVVQYI | 23236 | PLCB1 |
| 24 | FTLGTTVFL | 4717 | NDUFC1 |
| 25 | LLVPAHLVAA | 11082 | ESM1 |
| 26 | SLMEILYTL | 91949 | COG7 |
| 27 | SLSDLLVSL | 23596 | OPN3 |
| 28 | FIADLVVGL | 2023, 2026, 2027 | ENO1, ENO2, ENO3 |
| 29 | ILLDLEQAL | 9820 | CUL7 |
| 30 | QLFYTKIFL | 5351 | PLOD1 |
| 31 | VLFGLDPAVIKV | 259217 | HSPA12A |
| 32 | FLAGGIRGSGA | 113730 | KLHDC7B |
| 33 | FIADVVEKI | 5654, 94031 | HTRA1, HTRA3 |
| 34 | ELNNQNFYL | 11113 | CIT |

TABLE 1-continued

Peptides according to the present invention

| SEQ ID No | Sequence | Gene ID(s) | Official Gene Symbol(s) |
|---|---|---|---|
| 35 | VLHSLQTQL | 51129 | ANGPTL4 |
| 36 | SLFGKKYIL | 2274 | FHL2 |
| 37 | VLAPVILML | 8714 | ABCC3 |
| 38 | VLLDTILQL | 11077 | HSF2BP |
| 39 | YLLNLNHLGL | 23471 | TRAM1 |
| 40 | YIQEHLLQI | 10625 | IVNS1ABP |
| 41 | GLLKTLQKL | 25932 | CLIC4 |
| 42 | VILDTGTIQL | 9027 | NAT8 |
| 43 | YLKDELDEL | 23255 | SOGA2 |
| 44 | ALFSFVTAL | 80727 | TTYH3 |
| 45 | ALLGIPLTL | 3777, 60598 | KCNK3, KCNK15 |
| 46 | GLSEVLVQI | 57553 | MICAL3 |
| 47 | TLAEVRAVQEI | 56950 | SMYD2 |
| 48 | VVASNIMEV | 5209 | PFKFB3 |
| 49 | VLIVEVPGV | 111 | ADCY5 |
| 50 | SLSDHIVLL | 3675 | ITGA3 |
| 51 | NLWPMILTL | 3675 | ITGA3 |
| 52 | SILDAVQRV | 137902 | PXDNL |
| 53 | FLLEIRQTL | 23161 | SNX13 |
| 54 | ALVAKGLVQA | 10327 | AKR1A1 |
| 55 | YLALILPVL | 9122 | SLC16A4 |
| 56 | ILMDFSNSM | 3691 | ITGB4 |
| 57 | SLQKEILYL | 55102 | ATG2B |
| 58 | FLVDFEQSHL | 1573 | CYP2J2 |
| 59 | SLKNNVVSV | 7045 | TGFBI |
| 60 | ILWKDIEYV | 143425 | SYT9 |
| 61 | SLMGILLRI | 22900 | CARD8 |
| 62 | VLAGPAFLVQL | 55244 | SLC47A1 |
| 63 | GLIEDHFDVTV | 51752 | ERAP1 |
| 64 | LLAASVALA | 4885 | NPTX2 |
| 65 | IIYGGSVTGA | 7167, 729708 | TPI1, TPI1P1 |
| 66 | TLLKTIIKV | 57545 | CC2D2A |
| 67 | LLDVLAPLV | 80781 | COL18A1 |
| 68 | YVLTQPPSV | 28796, 28815, 28831, 3537, 3538 | IGLV3-21, IGLV2-14, IGLJ3, IGLC1, IGLC2 |
| 69 | ILADLLPSL | 25979 | DHRS7B |
| 70 | SLTALRLLL | 9920 | KBTBD11 |

TABLE 1-continued

Peptides according to the present invention

| SEQ ID No | Sequence | Gene ID(s) | Official Gene Symbol(s) |
|---|---|---|---|
| 71 | ALDGHLYAV | 9920 | KBTBD11 |
| 72 | YSLEKVFGI | 10916 | MAGED2 |
| 73 | GLDGIPFTV | 7205 | TRIP6 |
| 74 | GLFHKQVTV | 23037 | PDZD2 |
| 75 | FLIKSINLV | 143879 | KBTBD3 |
| 76 | VLADDHLIEV | 100034743, 5174, 728939 | PDZK1P2, PDZK1, PDZK1P1 |
| 77 | SLIKHKIML | 523 | ATP6V1A |
| 78 | ALLDTVVQA | 8911, 8912 | CACNA1I, CACNA1H |
| 79 | ALADIVWRA | 84182 | FAM188B |
| 80 | KLASMLETL | 112464 | PRKCDBP |
| 81 | SLLPALPKL | 4036 | LRP2 |
| 82 | SLLQATDFMSL | 7070 | THY1 |
| 83 | IQWSIVPEV | 23151 | GRAMD4 |
| 84 | YLMDEGAHL | 7358 | UGDH |
| 85 | FVMSEIRTV | 114991 | ZNF618 |
| 86 | GLLQGKLALL | 4835 | NQO2 |
| 87 | LADGVQKV | 8542 | APOL1 |
| 88 | TLAELHISL | 84166 | NLRC5 |
| 89 | SLLLAVTEV | 3714 | JAG2 |
| 90 | FTLEKNFVI | 1292 | COL6A2 |
| 91 | MLLSSLVSL | 79001 | VKORC1 |
| 92 | FLFRDILEL | 29102 | DROSHA |

TABLE 2

Additional peptides according to the present invention with no prior known cancer association

| SEQ ID No | Sequence | Gene ID(s) | Official Gene Symbol(s) |
|---|---|---|---|
| 93 | GVMAGDIYSV | 123 | PLIN2 |
| 94 | ILHHKVYDL | 1528 | CYB5A |
| 95 | KLTDVGIATL | 115701 | ALPK2 |
| 96 | TLAETLVNL | 283372, 283373 | ANKRD52 |
| 97 | TLISELVQA | 9820 | CUL7 |
| 98 | KIPPVSPSI | 57561 | ARRDC3 |
| 99 | GLAPHLEQI | 79711 | IPO4 |
| 100 | KLNVAPLAV | 653784, 80097 | MZT2A, MZT2B |

TABLE 2-continued

Additional peptides according to the present invention with no prior known cancer association

| SEQ ID No | Sequence | Gene ID(s) | Official Gene Symbol(s) |
|---|---|---|---|
| 101 | HIYDKAFITV | 2321 | FLT1 |
| 102 | LLFDVHTTL | 65250 | C5orf42 |
| 103 | KLQDGLLHI | 7076 | TIMP1 |
| 104 | ALFEGVVRQI | 6236 | RRAD |
| 105 | ALADLDELLIRA | 3339 | HSPG2 |
| 106 | VLMDLKALL | 51428 | DDX41 |
| 107 | VLMDLKALLL | 51428 | DDX41 |
| 108 | VLISVLQAI | 26999 | CYFIP2 |
| 109 | YLWSRVEKL | 120892 | LRRK2 |
| 110 | LLDLHSYLL | 10299 | MARCH6 |
| 111 | TLLETEMLL | 80817 | CEP44 |
| 112 | LLFDHLEPIEL | 25780 | RASGRP3 |
| 113 | SLFDWNVKL | 134111 | UBE2QL1 |
| 114 | ALAVNISAA | 908 | CCT6A |

TABLE 3

Peptides useful for e.g. personalized cancer therapies

| SEQ ID No | Sequence | Gene ID(s) | Official Gene Symbol(s) |
|---|---|---|---|
| 115 | LLDPKTIFL | 26762 | HAVCR1 |
| 116 | GLVDIMVHL | 8701 | DNAH11 |
| 117 | VLFGELPAL | 8701 | DNAH11 |
| 118 | FLNAIETAL | 8701 | DNAH11 |
| 119 | RLHDENILL | 23322 | RPGRIP1L |
| 120 | GLAGDNIYL | 6582 | SLC22A2 |
| 121 | ALLRTVVSV | 2590 | GALNT2 |
| 122 | SLDPSSPQV | 9514 | GAL3ST1 |
| 123 | YVDPVITSI | 4233 | MET |
| 124 | ILSPLSVAL | 5345 | SERPINF2 |
| 125 | KLDPTKTTL | 10397 | NDRG1 |
| 126 | KIQEILTQV | 10643 | IGF2BP3 |
| 127 | VLAPLFVYL | 2535, 8321, 8324 | FZD2, FZD1, FZD7 |
| 128 | YLEEDVYQL | 23255 | SOGA2 |
| 129 | VLAPRVLRA | 5954 | RCN1 |
| 130 | ALPTVLVGV | 5351 | PLOD1 |
| 131 | VMAGDIYSV | 123 | PLIN2 |
| 132 | SVASTITGV | 123 | PLIN2 |
| 133 | QLIDYERQL | 11072 | DUSP14 |
| 134 | VADKIHSV | 11072 | DUSP14 |
| 135 | VVDEGPTGV | 9123 | SLC16A3 |
| 136 | YQDPHSTAV | 1956 | EGFR |
| 137 | TLVAIVVGV | 60681 | FKBP10 |
| 138 | SLDTLMTYV | 22829 | NLGN4Y |
| 139 | ILNVDGLIGV | 47 | ACLY |
| 140 | SLANNVTSV | 131566 | DCBLD2 |
| 141 | LLVDDSFLHTV | 253982 | ASPHD1 |
| 142 | SVDVSPPKV | 113146 | AHNAK2 |
| 143 | ALFVRLLALA | 7045 | TGFBI |
| 144 | RLLDVLAPLV | 80781 | COL18A1 |
| 145 | SLHFLILYV | 487, 488 | ATP2A1, ATP2A2 |
| 146 | KLIDLSQVMYL | 346389 | MACC1 |
| 147 | ALADKELLPSV | 84883 | AIFM2 |
| 148 | KLLTEVHAA | 101 | ADAM8 |
| 149 | SILTIEDGIFEV | 100287551, 3306, 3312 | HSPA8P8, HSPA2, HSPA8 |
| 150 | TLMPNINKL | 5169 | ENPP3 |
| 151 | YMYEGPAPRI | 5169 | ENPP3 |

The present invention furthermore generally relates to the peptides according to the present invention for use in the treatment of proliferative diseases, such as, for example, lung cancer, brain cancer, stomach cancer, colon or rectal cancer, liver cancer, pancreatic cancer, prostate cancer, leukemia, breast cancer, melanoma, ovarian cancer, and esophageal cancer.

Particularly preferred are the peptides—alone or in combination—according to the present invention selected from the group consisting of SEQ ID NO: 1 to SEQ ID NO: 114. More preferred are the peptides—alone or in combination—selected from the group consisting of SEQ ID NO: 1 to SEQ ID NO: 63 (see Table 1), and their uses in the immunotherapy of RCC, lung cancer, brain cancer, stomach cancer, colon or rectal cancer, liver cancer, pancreatic cancer, prostate cancer, leukemias, breast cancer, melanoma, ovarian cancer, and esophageal cancer, and preferably RCC.

As shown in the following Table 4A, many of the peptides according to the present invention are also found on other tumor types and can, thus, also be used in the immunotherapy of other indications. Also refer to FIG. 1E and Example 1.

TABLE 4A

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation.

| SEQ ID No | Sequence | Other relevant organs/diseases |
|---|---|---|
| 1 | ALIVSLPYL | Liver |
| 2 | ILWREVVTL | Ovary |
| 5 | YLYPNLTRL | Liver |
| 8 | GLASFKSFL | Pancreas |
| 12 | ALDPSGNQLI | Ovary |
| 14 | ALLTETIFL | Leukocytes |
| 15 | ILIKHLVKV | Liver |
| 16 | FMPEELPQL | Pancreas, Breast, Ovary |
| 21 | RLIQGDQILSV | Lung, Colon, Rectum, Liver, Ovary |
| 23 | YIQEVVQYI | Liver |
| 24 | FTLGTTVFL | Liver, Prostate, Leukocytes, Esophagus |
| 26 | SLMEILYTL | Colon, Rectum, Pancreas, Prostate, Ovary |
| 27 | SLSDLLVSL | Lung, Liver, Pancreas, Leukocytes |
| 28 | FIADLVVGL | Melanoma |
| 29 | ILLDLEQAL | Lung, Pancreas, Prostate, Breast, Ovary |
| 30 | QLFYTKIFL | Lung, Colon, Rectum, Ovary |
| 31 | VLFGLDPAVIKV | Brain, Ovary |
| 32 | FLAGGIRGSGA | Stomach |
| 33 | FIADVVEKI | Lung, Leukocytes, Ovary |
| 34 | ELNNQNFYL | Melanoma, Esophagus |
| 36 | SLFGKKYIL | Colon, Rectum |
| 37 | VLAPVILML | Lung, Colon, Rectum, Pancreas, Ovary |
| 38 | VLLDTILQL | Brain, Liver, Pancreas, Melanoma, Ovary |
| 39 | YLLNLNHLGL | Lung, Liver, Leukocytes |
| 44 | ALFSFVTAL | Lung, Melanoma, Ovary |
| 45 | ALLGIPLTL | Prostate, Ovary, Esophagus |
| 46 | GLSEVLVQI | Colon, Rectum |
| 47 | TLAEVRAVQEI | Liver, Melanoma |
| 49 | VLIVEVPGV | Ovary |
| 50 | SLSDHIVLL | Lung |
| 51 | NLWPMILTL | Lung, Pancreas, Esophagus |
| 52 | SILDAVQRV | Lung, Brain, Pancreas, Ovary |
| 54 | ALVAKGLVQA | Melanoma, Ovary |
| 55 | YLALILPVL | Melanoma |
| 56 | ILMDFSNSM | Pancreas |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation.

| SEQ ID No | Sequence | Other relevant organs/diseases |
|---|---|---|
| 59 | SLKNNVVSV | Pancreas, Ovary, Esophagus |
| 61 | SLMGILLRI | Leukocytes |
| 63 | GLIEDHFDVTV | Lung, Colon, Rectum, Prostate, Leukocytes, Melanoma, Ovary |
| 65 | IIYGGSVTGA | Breast |
| 66 | TLLKTIIKV | Brain |
| 67 | LLDVLAPLV | Lung, Stomach, Liver, Pancreas, Breast, Esophagus |
| 68 | YVLTQPPSV | Lung, Pancreas, Leukocytes, Esophagus |
| 69 | ILADLLPSL | Lung, Brain, Pancreas, Breast, Ovary |
| 72 | YSLEKVFGI | Liver |
| 73 | GLDGIPFTV | Brain, Pancreas, Breast, Melanoma |
| 78 | ALLDTVVQA | Liver, Prostate |
| 79 | ALADIVWRA | Lung, Brain, Colon, Rectum, Liver, Pancreas, Prostate, Ovary, Esophagus |
| 82 | SLLQATDFMSL | Colon, Rectum, Pancreas, Esophagus |
| 84 | YLMDEGAHL | Liver |
| 85 | FVMSEIRTV | Liver |
| 86 | GLLQGKLALL | Liver, Melanoma |
| 87 | LADGVQKV | Breast, Melanoma |
| 88 | TLAELHISL | Ovary |
| 90 | FTLEKNFVI | Prostate |
| 91 | MLLSSLVSL | Lung, Liver |
| 93 | GVMAGDIYSV | Lung, Colon, Rectum, Liver, Esophagus |
| 94 | ILHHKVYDL | Liver |
| 96 | TLAETLVNL | Lung, Stomach, Colon, Rectum, Pancreas, Prostate, Breast, Ovary, Esophagus |
| 97 | TLISELVQA | Lung, Colon, Rectum, Pancreas, Prostate, Breast, Melanoma, Ovary, Esophagus |
| 98 | KIPPVSPSI | Lung, Liver, Breast |
| 99 | GLAPHLEQI | Liver, Ovary |
| 100 | KLNVAPLAV | Lung, Brain, Colon, Rectum, Liver, Pancreas, Melanoma, Ovary |
| 101 | HIYDKAFITV | Liver, Ovary |
| 102 | LLFDVHTTL | Lung, Brain |
| 103 | KLQDGLLHI | Brain, Colon, Rectum, Liver |
| 104 | ALFEGVVRQI | Liver, Melanoma, Esophagus |
| 105 | ALADLDELLIRA | Pancreas, Melanoma |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation.

| SEQ ID No | Sequence | Other relevant organs/diseases |
| --- | --- | --- |
| 107 | VLMDLKALLL | Prostate, Leukocytes, Ovary |
| 108 | VLISVLQAI | Leukocytes |
| 109 | YLWSRVEKL | Pancreas, Ovary |
| 110 | LLDLHSYLL | Stomach, Leukocytes |
| 111 | TLLETEMLL | Pancreas, Breast |
| 112 | LLFDHLEPIEL | Leukocytes |
| 113 | SLFDWNVKL | Liver, Prostate |
| 114 | ALAVNISAA | Lung, Brain, Liver, Pancreas, Esophagus |
| 115 | LLDPKTIFL | Colon, Rectum, Liver |
| 116 | GLVDIMVHL | Ovary |
| 117 | VLFGELPAL | Lung, Pancreas, Breast, Ovary |
| 119 | RLHDENILL | Lung, Brain, Colon, Rectum, Liver, Pancreas, Prostate, Ovary, Esophagus |
| 121 | ALLRTVVSV | Lung, Liver, Pancreas, Breast, Ovary |
| 122 | SLDPSSPQV | Liver |
| 123 | YVDPVITSI | Lung |
| 124 | ILSPLSVAL | Liver, Pancreas |
| 125 | KLDPTKTTL | Prostate |
| 126 | KIQEILTQV | Lung, Brain, Stomach, Colon, Rectum, Liver, Pancreas, Leukocytes, Ovary, Esophagus |
| 127 | VLAPLFVYL | Lung, Pancreas, Breast, Melanoma |
| 128 | YLEEDVYQL | Lung, Pancreas |
| 129 | VLAPRVLRA | Lung, Brain, Colon, Rectum, Liver, Pancreas, Ovary |
| 130 | ALPTVLVGV | Lung, Brain, Stomach, Colon, Rectum, Liver, Melanoma, Esophagus |
| 131 | VMAGDIYSV | Lung, Liver, Pancreas, Esophagus |
| 132 | SVASTITGV | Liver, Breast |
| 133 | QLIDYERQL | Lung, Colon, Rectum, Liver, Pancreas, Esophagus |
| 134 | VADKIHSV | Stomach, Pancreas, Esophagus |
| 135 | VVDEGPTGV | Lung, Brain, Stomach, Liver, Pancreas, Leukocytes, Breast, Ovary, Esophagus |
| 136 | YQDPHSTAV | Brain, Liver |
| 137 | TLVAIVVGV | Lung, Brain, Stomach, Colon, Rectum, Liver, Pancreas, Prostate, Breast, Ovary |
| 138 | SLDTLMTYV | Lung, Brain, Colon, Rectum, Pancreas, Prostate, Leukocytes, Esophagus |
| 139 | ILNVDGLIGV | Brain, Colon, Rectum, Liver, Prostate |
| 140 | SLANNVTSV | Lung, Brain, Pancreas, Melanoma, Ovary, |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation.

| SEQ ID No | Sequence | Other relevant organs/diseases |
|---|---|---|
| | | Esophagus |
| 141 | LLVDDSFLHTV | Brain, Liver, Pancreas, Melanoma, Ovary, Esophagus |
| 142 | SVDVSPPKV | Lung, Pancreas, Melanoma, Esophagus |
| 143 | ALFVRLLALA | Lung, Brain, Stomach, Colon, Rectum, Liver, Melanoma, Esophagus |
| 144 | RLLDVLAPLV | Liver |
| 145 | SLHFLILYV | Lung, Brain, Colon, Rectum, Liver, Melanoma, Ovary |
| 146 | KLIDLSQVMYL | Lung, Colon, Rectum, Pancreas, Ovary |
| 147 | ALADKELLPSV | Lung, Colon, Rectum, Liver, Pancreas, Melanoma, Ovary |
| 148 | KLLTEVHAA | Lung, Stomach, Colon, Rectum, Liver, Pancreas, Breast, Ovary, Esophagus |
| 149 | SILTIEDGIFEV | Lung, Brain, Colon, Rectum, Liver, Pancreas, Prostate, Leukocytes, Breast, Melanoma, Ovary |
| 150 | TLMPNINKL | Liver |

TABLE 4B

Peptides according to the present invention and their specific uses in other proliferative diseases, especially in other cancerous diseases. The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, cartilage, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID No | Sequence | Additional Entities |
|---|---|---|
| 2 | ILWREVVTL | Melanoma, NHL |
| 4 | FLSQDIITV | Uterine Cancer |
| 6 | VLFELSKTV | AML |
| 8 | GLASFKSFL | Melanoma, Urinary bladder cancer, Uterine Cancer, Gallbladder Cancer, Bile Duct Cancer |
| 10 | KLLQNNYGL | BRCA, Gallbladder Cancer, Bile Duct Cancer |
| 12 | ALDPSGNQLI | Brain Cancer |
| 13 | KIMAQILTV | CLL, NHL |
| 14 | ALLTETIFL | NHL |
| 15 | ILIKHLVKV | Uterine Cancer, NHL |

TABLE 4B-continued

Peptides according to the present invention and their specific uses in other proliferative diseases, especially in other cancerous diseases. The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, cartilage, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID No | Sequence | Additional Entities |
|---|---|---|
| 17 | ILAQQVHAL | Uterine Cancer |
| 18 | YVLDLAAKV | SCLC, CLL, BRCA, Melanoma, Uterine Cancer, NHL |
| 20 | AVANTTFTV | Esophageal Cancer, Urinary bladder cancer, Uterine Cancer |
| 21 | RLIQGDQILSV | SCLC, BRCA, Esophageal Cancer, Urinary bladder cancer, Uterine Cancer, Gallbladder Cancer, Bile Duct Cancer, OC |
| 24 | FTLGTTVFL | Melanoma, Uterine Cancer, NHL |
| 26 | SLMEILYTL | Melanoma, Gallbladder Cancer, Bile Duct Cancer, AML, OC, SCLC |
| 27 | SLSDLLVSL | CRC, Melanoma, Uterine Cancer, AML, NHL |
| 28 | FIADLVVGL | SCLC, CLL, AML, NHL |
| 29 | ILLDLEQAL | Melanoma, Urinary bladder cancer, Uterine Cancer, Gallbladder Cancer, Bile Duct Cancer, AML, NHL, OC |
| 30 | QLFYTKIFL | Melanoma, Esophageal Cancer, Urinary bladder cancer, Uterine Cancer, Gallbladder Cancer, Bile Duct Cancer |
| 33 | FIADVVEKI | SCLC, BRCA, Esophageal Cancer |
| 34 | ELNNQNFYL | CRC, Urinary bladder cancer, AML, NHL |
| 36 | SLFGKKYIL | Urinary bladder cancer, Uterine Cancer, Gallbladder Cancer, Bile Duct Cancer |
| 38 | VLLDTILQL | NSCLC, SCLC, CLL, BRCA, Esophageal Cancer, Urinary bladder cancer, Uterine Cancer, Gallbladder Cancer, Bile Duct Cancer, AML, NHL, OC |
| 39 | YLLNLNHLGL | NHL |
| 40 | YIQEHLLQI | Melanoma |
| 43 | YLKDELDEL | Esophageal Cancer, Gallbladder Cancer, Bile Duct Cancer, NHL |
| 45 | ALLGIPLTL | BRCA, Melanoma, Urinary bladder cancer, Uterine Cancer, OC |
| 46 | GLSEVLVQI | SCLC, HCC, Melanoma, Urinary bladder cancer, Gallbladder Cancer, Bile Duct Cancer, NHL |
| 48 | VVASNIMEV | BRCA, Melanoma |
| 49 | VLIVEVPGV | Gallbladder Cancer, Bile Duct Cancer, OC |
| 50 | SLSDHIVLL | PC, Melanoma, Esophageal Cancer, Urinary bladder cancer, Gallbladder Cancer, Bile Duct Cancer |
| 51 | NLWPMILTL | Melanoma, Uterine Cancer, Gallbladder Cancer, Bile Duct Cancer, Esophageal Cancer |
| 52 | SILDAVQRV | SCLC, BRCA, Melanoma, Uterine Cancer |
| 54 | ALVAKGLVQA | NHL |

TABLE 4B-continued

Peptides according to the present invention and their specific uses in other proliferative diseases, especially in other cancerous diseases. The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, cartilage, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID No | Sequence | Additional Entities |
|---|---|---|
| 55 | YLALILPVL | CLL |
| 56 | ILMDFSNSM | Urinary bladder cancer, Gallbladder Cancer, Bile Duct Cancer |
| 57 | SLQKEILYL | Melanoma |
| 59 | SLKNNVVSV | Melanoma, Uterine Cancer, Gallbladder Cancer, Bile Duct Cancer |
| 61 | SLMGILLRI | BRCA |
| 62 | VLAGPAFLVQL | Uterine Cancer |
| 63 | GLIEDHFDVTV | SCLC |
| 64 | LLAASVALA | Brain Cancer, AML |
| 65 | IIYGGSVTGA | CLL, Melanoma, Urinary bladder cancer, Uterine Cancer |
| 66 | TLLKTIIKV | Melanoma, Urinary bladder cancer |
| 67 | LLDVLAPLV | CRC, Melanoma, Urinary bladder cancer, Uterine Cancer, Gallbladder Cancer, Bile Duct Cancer |
| 68 | YVLTQPPSV | BRCA |
| 69 | ILADLLPSL | SCLC, Melanoma, Esophageal Cancer, Uterine Cancer, AML, NHL |
| 72 | YSLEKVFGI | Brain Cancer, GC, CRC, PrC, BRCA, Melanoma, OC, Urinary bladder cancer, AML, PC |
| 73 | GLDGIPFTV | GC, Urinary bladder cancer, Uterine Cancer, AML |
| 75 | FLIKSINLV | CLL, Melanoma, AML |
| 76 | VLADDHLIEV | HCC, Gallbladder Cancer, Bile Duct Cancer |
| 77 | SLIKHKIML | CRC, Melanoma, Uterine Cancer |
| 78 | ALLDTVVQA | BRCA |
| 79 | ALADIVWRA | SCLC, BRCA, Urinary bladder cancer, Uterine Cancer, Gallbladder Cancer, Bile Duct Cancer, Esophageal Cancer, OC |
| 80 | KLASMLETL | Melanoma |
| 81 | SLLPALPKL | BRCA |
| 82 | SLLQATDFMSL | NSCLC, Brain Cancer, BRCA, Melanoma, Uterine Cancer, NHL, PC |
| 83 | IQWSIVPEV | CLL, Melanoma, Gallbladder Cancer, Bile Duct Cancer, AML, NHL |
| 84 | YLMDEGAHL | Gallbladder Cancer, Bile Duct Cancer |
| 85 | FVMSEIRTV | Uterine Cancer, Gallbladder Cancer, Bile Duct Cancer |

TABLE 4B-continued

Peptides according to the present invention and their specific uses in other proliferative diseases, especially in other cancerous diseases. The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, cartilage, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID No | Sequence | Additional Entities |
|---|---|---|
| 86 | GLLQGKLALL | Uterine Cancer, NHL |
| 88 | TLAELHISL | CLL, Esophageal Cancer |
| 89 | SLLLAVTEV | SCLC, BRCA, Melanoma, Urinary bladder cancer |
| 90 | FTLEKNFVI | CRC, BRCA, PC |
| 91 | MLLSSLVSL | SCLC, Melanoma, Urinary bladder cancer, Gallbladder Cancer, Bile Duct Cancer |
| 92 | FLFRDILEL | Melanoma, AML |
| 93 | GVMAGDIYSV | Gallbladder Cancer, Bile Duct Cancer, PC |
| 95 | KLTDVGIATL | Melanoma, NHL |
| 96 | TLAETLVNL | SCLC, HCC, CLL, Melanoma, Urinary bladder cancer, Uterine Cancer, Gallbladder Cancer, Bile Duct Cancer, AML, NHL |
| 97 | TLISELVQA | SCLC, GC, HCC, CLL, Urinary bladder cancer, Uterine Cancer, Gallbladder Cancer, Bile Duct Cancer, NHL |
| 98 | KIPPVSPSI | Uterine Cancer, NHL |
| 99 | GLAPHLEQI | BRCA, Melanoma, AML, NHL |
| 100 | KLNVAPLAV | CLL, BRCA, Uterine Cancer, AML, NHL, OC |
| 101 | HIYDKAFITV | SCLC, BRCA |
| 102 | LLFDVHTTL | SCLC, Melanoma, Urinary bladder cancer, Uterine Cancer, AML |
| 103 | KLQDGLLHI | SCLC, PC, Melanoma, OC, NHL |
| 104 | ALFEGVVRQI | Urinary bladder cancer |
| 105 | ALADLDELLIRA | BRCA |
| 106 | VLMDLKALL | AML |
| 107 | VLMDLKALLL | AML |
| 108 | VLISVLQAI | BRCA, AML, NHL |
| 109 | YLWSRVEKL | CLL, NHL |
| 110 | LLDLHSYLL | Uterine Cancer |
| 111 | TLLETEMLL | Urinary bladder cancer |
| 112 | LLFDHLEPIEL | BRCA, NHL |

TABLE 4B-continued

Peptides according to the present invention and their specific uses in other proliferative diseases, especially in other cancerous diseases. The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, blood cells, blood vessel, bone marrow, brain, cartilage, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID No | Sequence | Additional Entities |
|---|---|---|
| 113 | SLFDWNVKL | SCLC, BRCA, Esophageal Cancer, Gallbladder Cancer, Bile Duct Cancer, AML, NHL |
| 114 | ALAVNISAA | GC, CRC, CLL, BRCA, Melanoma, Urinary bladder cancer, Uterine Cancer, Gallbladder Cancer, Bile Duct Cancer, AML, NHL, PC |

NSCLC = non-small cell lung cancer, SCLC = small cell lung cancer, RCC = kidney cancer, CRC = colon or rectum cancer, GC = stomach cancer, HCC = liver cancer, PC = pancreatic cancer, PrC = prostate cancer, BRCA = breast cancer, MCC = Merkel cell carcinoma, OC = ovarian cancer, NHL = non-Hodgkin lymphoma, AML = acute myeloid leukemia, CLL = chronic lymphocytic leukemia.

Thus, another aspect of the present invention relates to the use of at least one peptide according to the present invention according to any one of SEQ ID No. 21, 27, 29, 30, 33, 37, 39, 44, 50, 51,52, 63, 67, 68, 69, 79, 91,93, 96, 97, 98, 100, 102, 114, 117, 119, 121, 123, 126, 127, 128, 129, 130, 131, 165, 137, 138, 140, 142, 143, 145, 146, 147, 148 and 149, for the—in one preferred embodiment combined—treatment of lung cancer.

Thus, another aspect of the present invention relates to the use of at least one peptide according to the present invention according to any one of SEQ ID No 31, 38, 52, 66, 69, 73, 79, 100, 102, 103, 114, 119, 126, 129, 130, 135, 136, 137, 138, 139, 140, 141, 143, 145 and 149 for the—in one preferred embodiment combined—treatment of brain cancer.

Thus, another aspect of the present invention relates to the use of at least one peptide according to the present invention according to any one of Seq ID No 32, 67, 96, 110, 126, 130, 134, 135, 137, 143 and 148 for the—in one preferred embodiment combined—treatment of gastric cancer.

Thus, another aspect of the present invention relates to the use of at least one peptide according to the present invention according to any one of Seq ID No 21, 26, 30, 36, 37, 46, 63, 79, 82, 93, 96, 97, 100, 103, 115, 119, 126, 129, 130, 133, 137, 138, 139, 143, 145, 146 147, 148 and 149 for the—in one preferred embodiment combined—treatment of colorectal cancer.

Thus, another aspect of the present invention relates to the use of at least one peptide according to the present invention according to any one of Seq ID No 1, 5, 15, 21, 23, 24, 27, 38, 39, 47, 67, 72, 78, 79, 84, 85, 86, 91,93, 94, 98, 99, 100, 101,103, 104, 113, 114, 115, 119, 121,122, 124, 126, 129, 130, 131,132, 133, 135, 136, 137, 139, 141,143, 144, 145, 147, 148, 149 and 150 for the—in one preferred embodiment combined—treatment of hepatic cancer.

Thus, another aspect of the present invention relates to the use of at least one peptide according to the present invention according to any one of Seq ID No 8, 16, 26, 27, 29, 37, 38, 51,52, 56, 59, 67, 68, 69, 73, 79, 82, 96, 97, 100, 105, 109, 111, 114, 117, 119, 121,124, 126, 127, 128, 129, 131,133, 134, 135, 137, 138, 140, 141,142, 146, 147, 148 and 149 for the—in one preferred embodiment combined—treatment of pancreatic cancer.

Thus, another aspect of the present invention relates to the use of at least one peptide according to the present invention according to any one of Seq ID No 24, 26, 29, 45, 63, 78, 79, 90, 96, 97, 107, 113, 119, 125, 137, 138, 139 and 149 for the—in one preferred embodiment combined—treatment of prostate cancer.

Thus, another aspect of the present invention relates to the use of at least one peptide according to the present invention according to any one of Seq ID No 14, 24, 27, 33, 39, 61, 63, 68, 107, 108, 110, 112, 126, 135, 138 and 149 for the—in one preferred embodiment combined—treatment of leukemias.

Thus, another aspect of the present invention relates to the use of at least one peptide according to the present invention according to any one of Seq ID No 16, 29, 65, 67, 69, 73, 87, 96, 97, 98, 111, 117, 121, 127, 132, 135, 137, 148 and 149 for the—in one preferred embodiment combined—treatment of breast cancer.

Thus, another aspect of the present invention relates to the use of at least one peptide according to the present invention according to any one of Seq ID No 28, 34, 38, 44, 47, 54, 55, 63, 73, 86, 87, 97, 100, 104, 105, 127, 130, 140, 141, 142, 143, 145, 147 and 149 for the—in one preferred embodiment combined—treatment of melanoma.

Thus, another aspect of the present invention relates to the use of at least one peptide according to the present invention according to any one of Seq ID No 2, 12, 16, 21, 26, 29, 30, 31,33, 37, 38, 44, 45, 49, 52, 54, 59, 63, 69, 79, 88, 96, 97, 99, 100, 101, 107, 109, 116, 117, 119, 121, 126, 129, 135, 137, 140, 141, 145, 146, 147, 148 and 149 for the—in one preferred embodiment combined—treatment of ovarian cancer.

Thus, another aspect of the present invention relates to the use of at least one peptide according to the present invention according to any one of Seq ID No 24, 34, 45, 51, 59, 67, 68, 79, 82, 93, 96, 97, 104, 114, 119, 126, 130, 131, 133, 134, 135, 138, 140, 141, 142, 143 and 148 for the—in one preferred embodiment combined—treatment of esophageal cancer.

Thus, another aspect of the present invention relates to the use of the peptides according to the present invention for the—preferably combined—treatment of a proliferative disease selected from the group of RCC, lung cancer, brain cancer, gastric cancer, colorectal cancer, hepatic cancer, pancreatic cancer, prostate cancer, leukemias, breast cancer, melanoma, ovarian cancer, and esophageal cancer, and preferably RCC.

Preferably, the present invention relates to the use of the peptides according to the present invention according to SEQ ID NO: 1 and/or 15 for the—preferably combined—treatment of a proliferative disease selected from the group of RCC, lung cancer, brain cancer, gastric cancer, colorectal cancer, hepatic cancer, pancreatic cancer, prostate cancer, leukemias, breast cancer, melanoma, ovarian cancer, and esophageal cancer, and preferably RCC.

The present invention furthermore relates to peptides according to the present invention that have the ability to bind to a molecule of the human major histocompatibility complex (MHC) class-I or—in an elongated form, such as a length-variant—MHC class-II.

The present invention further relates to the peptides according to the present invention wherein said peptides (each) consist or consist essentially of an amino acid sequence according to SEQ ID NO: 1 to SEQ ID NO: 114.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present invention further relates to a nucleic acid, encoding the peptides according to the present invention. The present invention further relates to the nucleic acid according to the present invention that is DNA, cDNA, PNA, RNA or combinations thereof.

The present invention further relates to an expression vector capable of expressing and/or expressing a nucleic acid according to the present invention.

The present invention further relates to a peptide according to the present invention, a nucleic acid according to the present invention or an expression vector according to the present invention for use in the treatment of diseases and in medicine, in particular in the treatment of cancer.

The present invention further relates to antibodies that are specific against the peptides according to the present invention or complexes of said peptides according to the present invention with MHC, and methods of making these.

The present invention further relates to T-cell receptors (TCRs), in particular soluble TCR (sTCRs) and cloned TCRs engineered into autologous or allogeneic T cells, and methods of making these, as well as NK cells or other cells bearing said TCR or cross-reacting with said TCRs.

The antibodies and TCRs are additional embodiments of the immunotherapeutic use of the peptides according to SEQ ID 1 to SEQ ID 151 according to the invention at hand.

The present invention further relates to a host cell comprising a nucleic acid according to the present invention or an expression vector as described before. The present invention further relates to the host cell according to the present invention that is an antigen presenting cell, and preferably is a dendritic cell.

The present invention further relates to a method for producing a peptide according to the present invention, said method comprising culturing the host cell according to the present invention, and isolating the peptide from said host cell or its culture medium.

The present invention further relates to said method according to the present invention, wherein the antigen is loaded onto class I or II MHC molecules expressed on the surface of a suitable antigen-presenting cell or artificial antigen-presenting cell by contacting a sufficient amount of the antigen with an antigen-presenting cell.

The present invention further relates to the method according to the present invention, wherein the antigen-presenting cell comprises an expression vector capable of expressing or expressing said peptide containing SEQ ID No. 1 to SEQ ID No.: 114, preferably containing SEQ ID No. 1 to SEQ ID No. 63, or a variant amino acid sequence.

The present invention further relates to activated T cells, produced by the method according to the present invention, wherein said T cell selectively recognizes a cell which expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as produced according to the present invention.

The present invention further relates to the use of any peptide as described, the nucleic acid according to the present invention, the expression vector according to the present invention, the cell according to the present invention, the activated T lymphocyte, the T cell receptor or the antibody or other peptide- and/or peptide-MHC-binding molecules according to the present invention as a medicament or in the manufacture of a medicament. Preferably, said medicament is active against cancer.

Preferably, said medicament is for a cellular therapy, a vaccine or a protein based on a soluble TCR or antibody.

The present invention further relates to a use according to the present invention, wherein said cancer cells are RCC, lung cancer, brain cancer, stomach cancer, colon or rectal cancer, liver cancer, pancreatic cancer, prostate cancer, leukemias, breast cancer, melanoma, ovarian cancer, and esophageal cancer, and preferably RCC cells.

The present invention further relates to biomarkers based on the peptides according to the present invention, herein called "targets" that can be used in the diagnosis of cancer, preferably RCC. The marker can be over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker.

For example, an antibody or soluble TCR can be used to stain sections of the tumor to detect the presence of a peptide of interest in complex with MHC.

Optionally the antibody carries a further effector function such as an immune stimulating domain or toxin.

The present invention also relates to the use of these novel targets in the context of cancer treatment.

ABCC3 is associated with hepatocellular carcinoma, ovarian cancer, rectal cancer, osteosarcoma, breast cancer, non-small cell lung cancer, glioblastoma multiforme and pancreatic ductal adenocarcinoma (Mohelnikova-Duchonova et al., 2013; Molina-Pinelo et al., 2014; Goode et al., 2014; Liu et al., 2014c; Yu et al., 2014; Sedlakova et al., 2015; Zuniga-Garcia et al., 2015; Wang et al., 2014c).

ACLY is aberrantly expressed in various tumors, such as breast, liver, colon, lung and prostate cancers, and is correlated reversely with tumor stage and differentiation (Zu et al., 2012).

ADAM8 over-expression in pancreatic cancer is associated with increased migration and invasiveness of pancreatic ductal adenocarcinoma cells (Schlomann et al., 2015).

ADAM8 is involved in tumor cell migration and invasion in lung cancer, renal cell carcinoma and brain cancers (Mochizuki and Okada, 2007).

ADCY5 gene hyper-methylation and reduced mRNA expression occurs in acute lymphoblastic leukemia, chronic lymphocytic leukemia and lung adenocarcinoma (Kuang et al., 2008; Tong et al., 2010; Sato et al., 2013a).

AHNAK2 is an important element of the non-classical secretion pathway of fibroblast growth factor 1 (FGF1), a factor involved in tumor growth and invasion (Kirov et al., 2015).

The expression of AIFM2 was shown to be down-regulated in the majority of human tumors (Wu et al., 2004; Mei et al., 2006). AIFM2 was identified as one of nine genes which were associated with functional suppression of tumorigenicity in ovarian cancer cell lines (Notaridou et al., 2011).

AKR1A1 was shown to be up-regulated in breast cancer and is associated with lung cancer and laryngeal cancer (Penning, 2014; Hlavac et al., 2014; Kim et al., 2012).

ALPK2 expression is down-regulated in colorectal adenoma and plays a possible role in the transition of normal colonic crypt to adenoma (Yoshida et al., 2012). ALPK2 shows a strong association between copy number loss and under-expression in gastric cancer (Junnila et al., 2010).

ANGPTL4 was shown to be up-regulated in breast cancer, serous ovarian cancer and is associated with glioblastoma, hepatocellular carcinoma, oral squamous cell carcinoma and lung cancer (Ferguson et al., 2013; Tanaka et al., 2015; Ng et al., 2014; Garner et al., 2015; Schumann et al., 2015; Johnson et al., 2015).

APOL1 expression is down-regulated in renal cell carcinoma tissues and cell lines (Hu et al., 2012).

ARRDC3 is associated with breast cancer and prostate cancer (Wang et al., 2014a; Huang et al., 2012a).

ATG2B frameshift mutations are common in gastric and colon carcinomas with high microsatellite instability (Kang et al., 2009).

ATP11A was shown to be up-regulated in colorectal cancer and is associated with lymphoblastic leukemia and is suggested as a biomarker of metastasis in colorectal cancer (Miyoshi et al., 2010; Zhang et al., 2005).

ATP2A1 was shown to be up-regulated in cancer cachexia (Fontes-Oliveira et al., 2013).

ATP2A2 is associated with skin cancer, colon cancer and lung cancer (Korosec et al., 2006; Hovnanian, 2007).

CACNA1H is associated with aldosterone-producing adenomas, prostate cancer and breast cancer (Felizola et al., 2014; Asaga et al., 2006; Gackiere et al., 2013).

CACNA1I is associated with colon cancer, breast cancer and prostate cancer (Basson et al., 2015).

CARD8 is highly expressed in several cancer cell lines including ovarian, breast and lung cancer as well as in tissues derived from patients with colorectal carcinoma, gastric or breast cancer (Pathan et al., 2001; Yamamoto et al., 2005).

CCT6A is associated with testicular germ cell tumors and malignant melanomas (Tanic et al., 2006; Alagaratnam et al., 2011).

CIT is frequently up-regulated in hepatocellular carcinoma (HCC) as compared with adjacent non-tumor tissues. CIT knock-down by RNAi suppresses tumorigenicity of HCC cells in vivo (Fu et al., 2011).

CLIC4 down-regulation in tumor cells and up-regulation in tumor stroma is common to many human cancers including renal, ovarian, breast, lung and cutaneous cancers, and marks malignant progression (Suh et al., 2007a; Okudela et al., 2014; Suh et al., 2007b).

Differential expression of COL18A1 was reported for bladder cancer, rhabdoid tumors and ovarian carcinoma and specific polymorphisms within the gene were shown to increase the risk for sporadic breast cancer (Fang et al., 2013; Gadd et al., 2010; Lourenco et al., 2006; Peters et al., 2005).

COL6A2 is associated with cervical cancer, poor overall survival in high-grade serous ovarian cancer, B-precursor acute lymphoblastic leukemia, hepatocellular carcinoma, primary and metastatic brain tumors, squamous cell carcinoma of the lung, head and neck squamous cell carcinoma and was described as a potential DNA methylation for cervical cancer (Cheon et al., 2014; Chen et al., 2014c; Vachani et al., 2007; Liu et al., 2010b; Seong et al., 2012; Hogan et al., 2011).

CUL7 is associated with pancreatic cancer and hepatocellular carcinoma (Wang et al., 2014b; Paradis et al., 2013).

CYB5A expression is down-regulated in hepatocellular carcinoma (Khan et al., 2013a). CYB5A is a prognostic factor for pancreatic ductal adenocarcinoma that exerts its tumor-suppressor function through autophagy induction and TRAF6 modulation (Giovannetti et al., 2014). CYB5A encodes an enzyme which detoxifies carcinogenic molecules and is a prognostic factor for pancreatic cancer (Blanke et al., 2014; Giovannetti et al., 2014).

CYFIP2 expression is increased in newly formed lymph nodes in breast cancer (Gantsev et al., 2013). CYFIP2 expression is reduced in human gastric tumor samples, compared with control tissues (Cheng et al., 2013). CYFIP2 is one of several apoptosis-related genes methylated in chronic lymphocytic leukemia (Halldorsdottir et al., 2012).

CYP2J2 is an enzyme, which was shown to be over-expressed in a variety of human cancers, including esophageal, lung, breast, stomach, liver and colon cancer. CYP2J2 increases the proliferation and inhibits the apoptosis of carcinoma cells by promoting EGFR phosphorylation and activation of PI3K and MAPK signaling and further metabolizes tyrosine kinase inhibitors, thereby conferring resistance to anti-cancer agents (Jiang et al., 2005; Narjoz et al., 2014).

DCBLD2 is up-regulated in glioblastomas and head and neck cancers (HNCs) and is required for EGFR-stimulated tumorigenesis (Feng et al., 2014). Furthermore, DCBLD2 is up-regulated in highly metastatic lung cancer sublines and tissue samples (Koshikawa et al., 2002). In contrast, the expression of DCBLD2 is silenced by hypermethylation of its promoter in gastric cancer (Kim et al., 2008).

DDX41 is associated with acute myeloid leukemia (Antony-Debre and Steidl, 2015).

DROSHA, one of the two critical enzymes in microRNA biosynthesis, is over-expressed in a number of cancers including gastrointestinal tumors, breast cancer and cervical cancer and appears to enhance proliferation, colony formation and migration of tumor cells (Avery-Kiejda et al., 2014; Havens et al., 2014; Zhou et al., 2013).

Single nucleotide polymorphisms in the DUSP14 gene are associated with altered melanoma risk (Yang et al., 2014a; Liu et al., 2013).

EGFR was shown to be up-regulated in breast cancer and salivary gland adenoid carcinoma and is associated with non-small cell lung cancer, hepatocellular carcinoma and colorectal cancer (Dienstmann et al., 2015; Wang et al., 2015b; Steinway et al., 2015; Xiao et al., 2015; Inoue et al., 2015).

EGLN3 expression was shown to be up-regulated in non-small cell lung cancer and renal cell carcinomas. Moreover, EGLN3 is associated with clear-cell renal cell carcinoma and colorectal cancer (Tanaka et al., 2014; Yang et al., 2014d; Toth et al., 2014; Chu et al., 2014).

ENO1 expression was shown to be up-regulated in non-small cell lung cancer. Furthermore, ENO1 is associated with endometrial carcinoma, pancreatic ductal adenocarcinoma, glioblastoma and nasopharyngeal carcinoma (Yang et al., 2014b; Naryzhnyi et al., 2014; Principe et al., 2015; Fu et al., 2015; Zhao et al., 2015a).

ENO2 is associated with lung cancer, solid neuroendocrine carcinoma, granular cell tumors and pancreatic cancer (Sigari et al., 2014; Zizi-Sermpetzoglou et al., 2014; Liu et al., 2014a; Bedir et al., 2015; Wang et al., 2013b).

ENO3 is associated with B cell lymphoma, alveolar soft part sarcoma, rhabdomyosarcoma and neuroblastoma (Oka et al., 1989; Mukai et al., 1986; Royds et al., 1985; Ishiguro et al., 1984).

ENPP3 is associated with neuroblastoma, stage II colorectal cancer, head and neck squamous cell carcinoma, acute basophilic leukemia and bile duct carcinoma (Agesen et al., 2012; Staal-Viliare et al., 2007; Gomez-Villafuertes et al., 2014; Yano et al., 2004; Thiel et al., 2011).

ERAP1 is associated with cervical carcinoma, renal cell carcinoma, esophageal squamous cell carcinoma, melanoma, ovarian carcinoma and neuroblastoma (Mehta et al., 2015; Forloni et al., 2010; Liu et al., 2010a; Kamphausen et al., 2010; Ayshamgul et al., 2011; Stoehr et al., 2013).

ESM1 expression was shown to be elevated in gastric cancer and is associated with hepatoblastoma, nasopharyngeal carcinoma and ovarian cancer and may be a potential biomarker for gastric cancer (Yu et al., 2013; Dong et al., 2014; Lv et al., 2014; El Behery et al., 2013).

FHL2 was shown to be up-regulated in acute myeloid leukemia, ovarian cancer, lung cancer, colon carcinoma, breast cancer, pancreatic ductal adenocarcinoma, and human malignant melanoma and down-regulated in prostate cancer and rhabdomyosarcoma (Kleiber et al., 2007; Westphal et al., 2015; Qian et al., 2010; Zienert et al., 2015).

FKBP10 was identified as a novel gene that participates in the acquisition and maintenance of the Adriamycin-resistant phenotype in leukemia cells (Sun et al., 2014b).

FKBP10 has been associated with colorectal cancer through its up-regulation (Olesen et al., 2005). In contrast, the under-expression of FKBP10 was characteristic for epithelial ovarian carcinomas (Quinn et al., 2013).

FLT1 is associated with colon cancer, prostate cancer, non-small cell lung cancer and pancreatic cancer (Awasthi et al., 2015; Heist et al., 2015; Tsourlakis et al., 2015; Zhang et al., 2015).

FZD1 is associated with esophageal cancer, thyroid carcinoma, uterus sarcoma, prostate cancer, squamous cell/adenosquamous carcinoma and adenocarcinoma of the gallbladder, colon cancer and breast cancer (Goksel et al., 2014; Hung et al., 2014; Davidov et al., 2014; Su et al., 2015; Zhang et al., 2012a; Planutis et al., 2013; Devaney et al., 2013; Li et al., 2014a).

FZD2 was shown to be up-regulated in esophageal cancer and is associated with gastrointestinal stromal tumor, salivary adenoid cystic carcinoma and colorectal cancer (Wang and Zheng, 2014; Ding et al., 2015; Prakash et al., 2005; Liu et al., 2014b).

FZD7 was shown to be up-regulated in ovarian cancer and is associated with cervical cancer, hepatocellular carcinoma, colorectal cancer, melanoma, breast cancer, gastric cancer and central neurocytoma (Anastas et al., 2014; Li et al., 2014c; Gonzalez et al., 2014; Song et al., 2014; Deng et al., 2015; Asad et al., 2014; Vasiljevic et al., 2013; Rocken and Warneke, 2012; Dey et al., 2013).

GAL3ST1 activity is increased in renal cell carcinoma (RCC) tissue and the RCC cell line SMKT-R3 (Honke et al., 1996). GAL3ST1 expression is up-regulated in ovarian epithelial carcinoma cells versus normal ovarian stromal tissue and normal surface ovarian epithelial cells (Liu et al., 2010c).

GALNT2, the N-acetylgalactosaminyltransferase 2, was shown to exert anti-proliferative and anti-metastatic activity through the decrease of MMP-2 and TGF-β1 in gastric cancer cells and through the inhibition EGF receptor activity in hepatocellular carcinoma, where it is frequently down-regulated. In contrast, in squamous cell carcinoma over-expression of GALNT2 was reported to enhance the invasive potential of tumor cells by modifying O-glycosylation and EGFR activity (Hua et al., 2012; Lin et al., 2014; Wu et al., 2011).

GRAMD4 is up-regulated in hepatocellular carcinoma (HCC) cell lines and HCC tissues, and the increased expression is correlated with the clinicopathological characteristics of HCC (Zhang et al., 2013).

HAVCR1 was described as a novel biomarker candidate associated with ovarian clear cell carcinoma and renal cell carcinoma (Bonventre, 2014; Kobayashi et al., 2015). HAVCR1 was shown to activate the IL-6/STAT-3/HIF-1A axis in clear cell renal cell carcinoma-derived cell lines and determines tumor progression and patient outcome (Cuadros et al., 2014). Constitutive expression of HAVCR1 in the kidney was described as a potential susceptibility trait for clear cell renal cell carcinoma development (Cuadros et al., 2013). HAVCR1 was described as being up-regulated in renal cell and ovarian clear cell carcinomas and colorectal cancer (Wang et al., 2013c). HAVCR1 up-regulation was described as a potential diagnostic biomarker for colorectal cancer and a prognostic marker for a longer disease-free interval after surgery, which may also be involved in the metastatic cascade in colorectal cancer (Wang et al., 2013c). HAVCR1 was shown to be associated with T cell large granular lymphocyte leukemia (Wlodarski et al., 2008).

HSF2BP encodes the HSF2 binding protein which associates with HSF2 and may be involved in modulating HSF2 activation (RefSeq, 2002).

HSF4 encodes heat-shock transcription factor 4, which activates heat-shock response genes under conditions of heat or other stresses (RefSeq, 2002). HSF4 was shown to be down-regulated in glioblastoma (Mustafa et al., 2010).

Different studies suggest an important role of HSPA2 in disease progression of cervical cancer, renal cell carcinoma and bladder cancer. Polymorphisms within the gene are associated with the development of gastric cancer (Ferrer-Ferrer et al., 2013; Garg et al., 2010a; Garg et al., 2010b; Singh and Suri, 2014).

HSPA8 was shown to be over-expressed in esophageal squamous cell carcinoma and high expression levels of HSPA8 in esophageal cancer cells in vitro counter-acted oxidative stress-induced apoptosis of these cells. Furthermore, HSPA8 is over-expressed in multiple myeloma and colonic carcinoma and BCR-ABL1-induced expression of HSPA8 promotes cell survival in chronic myeloid leukemia (Chatterjee et al., 2013; Dadkhah et al., 2013; Jose-Eneriz et al., 2008; Kubota et al., 2010; Wang et al., 2013a).

HSPG2 is associated with melanoma, oral squamous cell carcinoma, clear cell renal cell carcinoma and prostate tumor and its down-regulation was shown in hepatocellular carcinoma and colon tumor (Nikitovic et al., 2014; Warren et al., 2014; Gbormittah et al., 2014; Zaghloul et al., 2015; Kawahara et al., 2014; Suhovskih et al., 2015; 2015; Elewa et al., 2015; Lai et al., 2011).

HTRA1 is associated with hepatocellular carcinoma, splenic marginal zone lymphoma, squamous cell carcinoma and neuroblastoma and was shown to be down-regulated in gastric cancer, breast cancer, gallbladder cancer and lung adenocarcinoma (Xu et al., 2014; D'Angelo et al., 2014; Fujinaga et al., 2014; Sahasrabuddhe et al., 2014; Franco et al., 2015; Arribas et al., 2015; Zhao et al., 2015b; Bao et al., 2015).

HTRA3 was shown to be up-regulated in oral squamous cell carcinoma and thyroid carcinoma and down-regulated in ovarian cancer, breast cancer, endometrial cancer and lung cancer, and is associated with colorectal cancer and may be a potential prognostic biomarker for oral cancer (Karagiannis et al., 2014; Zhao et al., 2014; Moriya et al., 2015; Narkiewicz et al., 2009; Beleford et al., 2010; Zurawa-Janicka et al., 2012; Yin et al., 2013).

IGF2BP3 encodes insulin-like growth factor II mRNA binding protein 3, an oncofetal protein, which represses translation of insulin-like growth factor II (RefSeq, 2002). In vitro studies have shown that IGF2BP3 promotes tumor cell proliferation, adhesion, and invasion. Furthermore, IGF2BP3 has been shown to be associated with aggressive and advanced cancers (Bell et al., 2013; Gong et al., 2014). IGF2BP3 over-expression has been described in numerous tumor types and correlated with poor prognosis, advanced tumor stage and metastasis, as for example in neuroblastoma, colorectal carcinoma, intrahepatic cholangiocarcinoma, hepatocellular carcinoma, prostate cancer, and renal cell carcinoma (Bell et al., 2013; Findeis-Hosey and Xu, 2012; Hu et al., 2014; Szarvas et al., 2014; Jeng et al., 2009; Chen et al., 2011; Chen et al., 2013; Hoffmann et al., 2008; Lin et al., 2013; Yuan et al., 2009).

IGLC1 newly acquired and recurrent deletions were detected in 3 out of 45 patients that showed tyrosine kinase inhibitor (TKI) resistance in chronic myeloid leukemia (CML) (Nowak et al., 2010).

IGLC2 loss of heterozygosity has been shown in 50% of informative cases of intracranial meningiomas (Kim et al., 1993).

IGLJ3 is the joining gene universally used for the composition of the preferred light chain IG lambda in hairy cell leukemia (Forconi et al., 2008).

IGLV2-14 is the third most frequent IGLV gene in chronic lymphocytic leukemia (CLL) compared with the relevant repertoires from normal, auto-reactive, and neoplastic cells (Stamatopoulos et al., 2005).

IGLV3-21 is the most frequent IGLV gene in chronic lymphocytic leukemia (CLL) compared with the relevant repertoires from normal, auto-reactive, and neoplastic cells (Stamatopoulos et al., 2005).

INADL is down-regulated in non-small cell lung cancer in response to cisplatin-gemcitabine combination chemotherapy (Ma et al., 2015).

ITGA3 was shown to be up-regulated in colorectal carcinoma and is associated with prostate cancer, epidermoid carcinoma, early gastric carcinoma and osteosarcoma (Yang et al., 2014c; Chong et al., 2014; Lustosa et al., 2014; Ren et al., 2014; Bauer et al., 2014; Mertens-Walker et al., 2015).

ITGB4 is associated with prostate cancer, gastric cancer, breast cancer, oral squamous cell carcinoma and ovarian cancer and was shown to be up-regulated in pancreatic ductal adenocarcinoma (Chen et al., 2014b; Xin et al., 2014; Zubor et al., 2015; Masugi et al., 2015; Gao et al., 2015b; Kawakami et al., 2015). ITGB4 (also called CD104) tends to associate with the alpha 6 subunit and is likely to play a pivotal role in the biology of several invasive carcinomas such as esophageal squamous cell carcinoma, bladder and ovarian carcinoma (Kwon et al., 2013; Pereira et al., 2014; Chen et al., 2014b). A single nucleotide polymorphism in ITGB4 seems to influence tumor aggressiveness and survival and may have prognostic value for breast cancer patients (Brendle et al., 2008).

IVNS1ABP is associated with BCL1/JH positive multiple myelomas and might be a potential prognostic marker of multiple myelomas (Ni et al., 2012).

JAG2 was shown to be up-regulated in pancreatic ductal adenocarcinoma, hepatocellular carcinoma and retinoblastoma and is associated with multiple myeloma, endometrial cancer, prostate cancer, osteosarcoma, head and neck cancer and urothelial carcinoma of bladder (Sun et al., 2014a; Li et al., 2014b; Carvalho et al., 2014; Xiao et al., 2014; Zhang et al., 2014a; Sasnauskiene et al., 2014; Lu et al., 2014; Hu et al., 2015; Li et al., 2013).

KCNK15 gene hyper-methylation was found in several cell lines, including colon cancer, leukemia, and bladder cancer (Shu et al., 2006).

KIF12 was shown to be over-expressed in breast cancer and is associated with kidney tumors, uterus cancer and pancreatic cancer (Katoh and Katoh, 2005; Tan et al., 2012).

KLHDC7B is associated with cervical squamous cell carcinoma and is a potential biomarker for cervical squamous cell carcinoma (Guo et al., 2015).

LRP2 is associated with hepatocellular carcinoma, pancreatic cancer, malignant melanoma, primary central nervous system lymphoma and clear cell renal cell carcinoma (Fernandez-Banet et al., 2014; Andersen et al., 2015; Pedersen et al., 2010; Schuetz et al., 2005; Anderson et al., 2013).

LRRK2 is associated with hormone-related cancer, breast cancer and concomitant non-skin cancers in Parkinson's disease patients and may be associated with hematological cancers in patients with Parkinson's disease (Ruiz-Martinez et al., 2014; Agalliu et al., 2015; Inzelberg et al., 2012).

MACC1 is over-expressed in many cancer entities including gastric, colorectal, lung and breast cancer and is associated with cancer progression, metastasis and poor survival of patients (Huang et al., 2013; Ma et al., 2013; Stein, 2013; Wang et al., 2015a; Wang et al., 2015c; Illm et al., 2015). MACC1 promotes carcinogenesis through targeting beta-catenin and PI3K/AKT signaling pathways, which leads to an increase of c-Met and beta-catenin and their downstream target genes including c-Myc, cyclin D1, caspase9, BAD and MMP9 (Zhen et al., 2014; Yao et al., 2015).

MAGED2 over-expression is associated with melanoma, breast cancer and colon cancer (Li et al., 2004; Strekalova et al., 2015).

MET was shown to be up-regulated in dedifferentiated liposarcoma and is associated with melanocytic tumors, hepatocellular carcinoma, non-small cell lung cancer, hereditary papillary kidney cancers and gastric adenocarcinomas (Petrini, 2015; Finocchiaro et al., 2015; Steinway et al., 2015; Bill et al., 2015; Yeh et al., 2015).

NAT8 is associated with lymphoblastic leukemia (Mak et al., 2014).

NDRG1 is a metastasis suppressor in cancers such as pancreatic cancer and was shown to be down-regulated in prostate cancer and colon cancer, whereas it was shown to be up-regulated in hepatocellular carcinoma and cervical adenocarcinoma (Nishio et al., 2008; Cheng et al., 2011; Bae et al., 2013; Richardson et al., 2013).

NLRC5 was shown to be down-regulated in lymphoid-derived tumor cell lines (Staehli et al., 2012).

NPTX2 is down-regulated by promoter hyper-methylation in pancreatic cancer, Ewing sarcoma and glioblastoma (Zhang et al., 2012b; Alholle et al., 2013; Shukla et al., 2013).

NQO2 is associated with endometrial cancer, papillary thyroid microcarcinoma and esophageal cancer (Hevir-Kene and Rizner, 2015; Malik et al., 2012; Lee et al., 2013).

OPN3 expression is decreased in 5-fluorouracil-resistant hepatocellular carcinoma cell lines Bel7402 and HepG2 compared to 5-fluorouracil-sensitive Bel7402 and HepG2 cells (Jiao et al., 2012).

PDZD2 is associated with small intestinal neuroendocrine tumors and prostate cancer (Tam et al., 2006; Rehfeld et al., 2014).

Overexpression of PDZK1 may play a role in drug resistance of multiple myeloma (RefSeq, 2002).

PFKFB3 was shown to be up-regulated in gastric cancer, colon cancer, lung cancer, breast cancer and is associated with pancreatic cancer, prostate cancer and glioblastoma (Minchenko et al., 2014; Fleischer et al., 2011; Ragnum et al., 2013).

PLCB1 is associated with primary head and neck squamous cell carcinoma, myeloid leukemia and glioblastoma multiforme (Guerrero-Preston et al., 2014; Waugh, 2014; Ramazzotti et al., 2011).

PLIN2 is involved in lipid storage and a plasma biomarker for the detection of early-stage colorectal cancer (Matsubara et al., 2011). PLIN2 is significantly increased in patients with clear cell and papillary renal cell carcinoma compared with controls. The preoperative urinary concentrations of PLIN2 reflect the tumor size and stage (Morrissey et al., 2014).

PLIN2 expression is significantly higher in lung adenocarcinoma specimens than in normal tissues and lung squamous cell carcinomas (Zhang et al., 2014b).

PLOD1 expression is associated with human breast cancer progression (Gilkes et al., 2013).

PRKCDBP was shown to be down-regulated in breast cancer brain metastases and primary breast cancer. Additionally, PRKCDBP is associated with breast cancer, colorectal cancer, endometrial cancer, lung cancer and gastric cancer (Bai et al., 2012; Moutinho et al., 2014; Li et al., 2015; Tong et al., 2012; Wikman et al., 2012).

RASGRP3 was shown to be up-regulated in glioblastoma, breast cancer and human melanoma and is associated with prostate cancer, hepatocellular carcinoma and oral cancers (Nagy et al., 2014; Sowalsky et al., 2015; Lee et al., 2015; Yang et al., 2011; Bhatnagar et al., 2012; Martinez-Lopez et al., 2012).

RCN1 is localized to the plasma membrane in human endothelial and prostate cancer cell lines (RefSeq, 2002). RCN1 is over-expressed in breast cancer (Amatschek et al., 2004).

REN is associated with renal cell carcinoma, pancreatic cancer, desmoplastic small round cell tumor and juxtaglomerular cell tumor (Elouazzani et al., 2014; Lee et al., 2014; Nakai et al., 2015; Araujo et al., 2015).

RGS5 was shown to be down-regulated in lung cancer, up-regulated in clear cell renal cell carcinoma, hepatocellular carcinoma, several lymphoma subtypes and parathyroid adenoma, and is associated with colorectal cancer, neuroblastoma, ovarian cancer, non-small cell lung cancer and gastric cancer (Volz et al., 2015; Xu et al., 2015; Wang et al., 2010a; Dannenmann et al., 2013; Koh et al., 2011; Huang et al., 2012b; Altman et al., 2012; Kumps et al., 2013; Sethakorn and Dulin, 2013; Hu et al., 2013).

RPGRIP1L suppresses anchorage-independent growth partly through the mitotic checkpoint protein Mad2 and is a candidate tumor suppressor gene in human hepatocellular carcinoma (Lin et al., 2009).

RRAD was shown to be down-regulated in lung cancer, ovarian cancer and nasopharyngeal carcinoma and is associated with glioblastoma multiforme, esophageal squamous cell carcinoma and hepatocellular carcinoma (Wang et al., 2014d; Yeom et al., 2014; Liu et al., 2015; Mo et al., 2012; Lin and Chuang, 2012; Jin et al., 2013).

SEMA5B is up-regulated in renal cell carcinoma, but, so far, its expression has not been found in other cancer types or normal tissues (Hirota et al., 2006).

The plasma level of the plasmin-alpha 2-plasmin inhibitor complex was shown to be a predictor of survival in non-small cell lung carcinoma and low activity of alpha 2-antiplasmin has been observed in the blood of the patients with prostatic carcinoma (Taguchi et al., 1996; Zietek et al., 1996).

The SLC16A3 expression has been associated with poor prognosis in hepatocellular cancer patients and increased cell proliferation, migration and invasion in cell line experiments (Gao et al., 2015a). The functional involvement of SLC16A3 in the tumorigenesis was shown in a subset of pancreatic cancer (Baek et al., 2014).

SLC16A4 was shown to be up-regulated in non-small lung cancer, gland adenoid carcinoma, pancreatic ductal carcinoma, oral squamous cell carcinoma and gastric cancer and is associated with breast cancer and hepatocellular carcinoma (Baek et al., 2014; Gao et al., 2015a; Yan et al., 2014; Jensen et al., 2014; Koo and Yoon, 2015; Granja et al., 2015; Baenke et al., 2015).

High expression of organic anion transporter 2 and organic cation transporter 2 is an independent predictor of good outcomes in patients with metastatic colorectal cancer treated with FOLFOX-based chemotherapy (Tashiro et al., 2014). mRNA expression of SLC22A2, SLC22A11, SLC28A1, SLC28A3 and SLC29A1 was down-regulated in pancreatic tumors when compared with non-neoplastic pancreatic tissues (Mohelnikova-Duchonova et al., 2013a). SLC22A2 (also known as OCT2) regulates uptake of cisplatin in proximal tubules, and inhibition of OCT2 protects against severe cisplatin-induced nephrotoxicity (Sprowl et al., 2013).

SLC47A1 is associated with prostate cancer (Joerger et al., 2015).

SLC6A13 expression was shown to be up-regulated in colon cancer (Tran et al., 2014b).

SMYD2 was shown to be up-regulated in esophageal squamous primary carcinoma, breast cancer, liver cancer, gastric cancer and acute lymphoblastic leukemia (Sakamoto et al., 2014; Komatsu et al., 2015; Nguyen et al., 2015).

SYT9 is associated with cervical cancer and prostate cancer and may present a potential biomarker for cervical cancer (Chen et al., 2014c; Bao et al., 2011).

TGFBI expression was shown to be elevated in cholangiocarcinoma, hepatic carcinoma, gastric carcinoma, esophageal squamous cell carcinoma and clear cell renal cell carcinoma. Furthermore, TGFBI was shown to be associated with colorectal cancer (Lebdai et al., 2015; Ozawa et al., 2014; Zhu et al., 2015; Han et al., 2015).

THY1 is a candidate tumor suppressor gene in nasopharyngeal carcinoma bearing anti-invasive activity (Lung et al., 2010).

TIMP1 protein expression is associated with poor prognosis in patients with metastatic liver disease, in childhood acute lymphoblastic leukemia and in breast cancer (Bunatova et al., 2012; Scrideli et al., 2010; Sieuwerts et al., 2007). TIMP1 is a potential serum marker for the detection of pancreatic cancer (Slater et al., 2013). TIMP1 is a well-known thyroid cancer marker (Griffith et al., 2006).

TPI1 was shown to be down-regulated in osteosarcoma and is associated with breast cancer, esophageal squamous cell carcinoma, glioblastoma, endometrial cancer and ovarian cancer (Zamani-Ahmadmahmudi et al., 2014; Chen et al., 2014a; Yoshida et al., 2013; Khan et al., 2013b; Gao et al., 2014).

TRIP6 was shown to be up-regulated in Ewings's sarcoma, nasopharyngeal carcinoma and glioblastoma and is associated with breast cancer (Pavlikova et al., 2015; Lai et al., 2010; Fei et al., 2013; Grunewald et al., 2013).

UBE2QL1 transcription was shown to be down-regulated in renal cell carcinoma (Wake et al., 2013).

UGDH is associated with colorectal cancer, prostate cancer, ovarian serous adenocarcinoma, breast cancer and hepatocellular carcinoma (Lapointe and Labrie, 1999; Konno, 2001; Fan et al., 2009; Wei et al., 2009; Wang et al., 2010b).

VKORC1 polymorphisms might be associated with the risk of developing prostate cancer (Nimptsch et al., 2009). VKORC1 influences PIVKAII (protein induced by vitamin K absence) concentration, which is used for screening for hepatocellular carcinoma (Wang et al., 2010c).

DETAILED DESCRIPTION OF THE INVENTION

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

The term "T-cell response" means the specific proliferation and activation of effector functions induced by a peptide in vitro or in vivo. For MHC class I restricted cytotoxic T cells, effector functions may be lysis of peptide-pulsed, peptide-precursor pulsed or naturally peptide-presenting target cells, secretion of cytokines, preferably Interferongamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11 or 12 or longer, and in case of MHC class II peptides (elongated variants of the peptides of the invention) they can be as long as 13, 14, 15, 16, 17, 18, 19 or 20 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present invention differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 5

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1 - Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| A*02 | Caucasian (North America) | 49.1% |
| A*02 | African American (North America) | 34.1% |
| A*02 | Asian American (North America) | 43.2% |
| A*02 | Latin American (North American) | 48.3% |
| DR1 | Caucasian (North America) | 19.4% |
| DR2 | Caucasian (North America) | 28.2% |
| DR3 | Caucasian (North America) | 20.6% |
| DR4 | Caucasian (North America) | 30.7% |
| DR5 | Caucasian (North America) | 23.3% |
| DR6 | Caucasian (North America) | 26.7% |
| DR7 | Caucasian (North America) | 24.8% |
| DR8 | Caucasian (North America) | 5.7% |
| DR9 | Caucasian (North America) | 2.1% |
| DR1 | African (North) American | 13.20% |
| DR2 | African (North) American | 29.80% |
| DR3 | African (North) American | 24.80% |
| DR4 | African (North) American | 11.10% |
| DR5 | African (North) American | 31.10% |
| DR6 | African (North) American | 33.70% |
| DR7 | African (North) American | 19.20% |
| DR8 | African (North) American | 12.10% |
| DR9 | African (North) American | 5.80% |
| DR1 | Asian (North) American | 6.80% |
| DR2 | Asian (North) American | 33.80% |
| DR3 | Asian (North) American | 9.20% |
| DR4 | Asian (North) American | 28.60% |
| DR5 | Asian (North) American | 30.00% |
| DR6 | Asian (North) American | 25.10% |
| DR7 | Asian (North) American | 13.40% |
| DR8 | Asian (North) American | 12.70% |
| DR9 | Asian (North) American | 18.60% |
| DR1 | Latin (North) American | 15.30% |
| DR2 | Latin (North) American | 21.20% |
| DR3 | Latin (North) American | 15.20% |
| DR4 | Latin (North) American | 36.80% |
| DR5 | Latin (North) American | 20.00% |
| DR6 | Latin (North) American | 31.10% |
| DR7 | Latin (North) American | 20.20% |
| DR8 | Latin (North) American | 18.60% |
| DR9 | Latin (North) American | 2.10% |
| A*24 | Philippines | 65% |
| A*24 | Russia Nenets | 61% |
| A*24:02 | Japan | 59% |
| A*24 | Malaysia | 58% |
| A*24:02 | Philippines | 54% |
| A*24 | India | 47% |
| A*24 | South Korea | 40% |
| A*24 | Sri Lanka | 37% |
| A*24 | China | 32% |
| A*24:02 | India | 29% |
| A*24 | Australia West | 22% |
| A*24 | USA | 22% |
| A*24 | Russia Samara | 20% |
| A*24 | South America | 20% |
| A*24 | Europe | 18% |

The peptides of the invention, preferably when included into a vaccine of the invention as described herein bind to A*02. A vaccine may also include pan-binding MHC class II peptides. Therefore, the vaccine of the invention can be used to treat cancer in patients that are A*02 positive, whereas no selection for MHC class II allotypes is necessary due to the pan-binding nature of these peptides.

If A*02 peptides of the invention are combined with peptides binding to another allele, for example A*24, a higher percentage of any patient population can be treated compared with addressing either MHC class I allele alone. While in most populations less than 50% of patients could be addressed by either allele alone, a vaccine comprising HLA-A*24 and HLA-A*02 epitopes can treat at least 60% of patients in any relevant population. Specifically, the following percentages of patients will be positive for at least one of these alleles in various regions: USA 61%, Western Europe 62%, China 75%, South Korea 77%, Japan 86% (calculated from www.allelefrequencies.net).

In a preferred embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

percent identity=$100[1-(C/R)]$ wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference and (iiii) the alignment has to start at position 1 of the aligned sequences; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

As mentioned above, the present invention thus provides a peptide comprising a sequence that is selected from the group of consisting of SEQ ID NO: 1 to SEQ ID NO: 114 or a variant thereof which is 88% homologous to SEQ ID NO: 1 to SEQ ID NO: 114, or a variant thereof that will induce T cells cross-reacting with said peptide. The peptides of the invention have the ability to bind to a molecule of the human major histocompatibility complex (MHC) class-I or elongated versions of said peptides to class II.

In the present invention, the term "homologous" refers to the degree of identity (see percent identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T cells induced by a variant of a specific peptide will be able to cross-react with the peptide itself (Appay et al., 2006; Colombetti et al., 2006; Fong et al., 2001; Zaremba et al., 1997).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 114. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T cells.

These T cells can subsequently cross-react with cells and kill cells that express a polypeptide that contains the natural amino acid sequence of the cognate peptide as defined in the aspects of the invention. As can be derived from the scientific literature and databases (Rammensee et al., 1999; Godkin et al., 1997), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO: 114, by maintaining the known anchor residues, and would be able to determine whether such variants maintain the ability to bind MHC class I or II molecules. The variants of the present invention retain the ability to bind to the TCR of activated T cells, which can subsequently cross-react with and kill cells that express a polypeptide containing the natural amino acid sequence of the cognate peptide as defined in the aspects of the invention.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, non-standard amino acids (i.e., other than the common naturally occurring proteinogenic amino acids) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

A peptide consisting essentially of the amino acid sequence as indicated herein can have one or two non-anchor amino acids (see below regarding the anchor motif) exchanged without that the ability to bind to a molecule of the human major histocompatibility complex (MHC) class-I or -II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) class-I or —II is substantially changed, or is negatively affected, when compared to the non-modified peptide.

The amino acid residues that do not substantially contribute to interactions with the T-cell receptor can be modified by replacement with other amino acids whose incorporation do not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 6

Variants and motif of the peptides according to SEQ ID NO: 1, 4 and 5.

| Position | 1 | 2 | 3 | 4 | 5 | 6 | 7 | 8 | 9 |
|---|---|---|---|---|---|---|---|---|---|
| SEQ ID NO: 1 | A | L | I | V | S | L | P | Y | L |
| Variant | | | | | | | | | V |
| | | | | | | | | | I |
| | | | | | | | | | A |
| | | M | | | | | | | V |
| | | M | | | | | | | I |
| | | M | | | | | | | |
| | | M | | | | | | | A |
| | | A | | | | | | | V |
| | | A | | | | | | | I |
| | | A | | | | | | | |
| | | A | | | | | | | A |
| | | V | | | | | | | V |
| | | V | | | | | | | I |
| | | V | | | | | | | |
| | | V | | | | | | | A |
| | | T | | | | | | | V |
| | | T | | | | | | | I |
| | | T | | | | | | | |
| | | T | | | | | | | A |
| | | Q | | | | | | | V |

TABLE 6-continued

Variants and motif of the peptides according to SEQ ID NO: 1, 4 and 5.

| Position | 1 | 2 | 3 | 4 | 5 | 6 | 7 | 8 | 9 |
|---|---|---|---|---|---|---|---|---|---|
|  |  | Q |  |  |  |  |  |  | I |
|  |  | Q |  |  |  |  |  |  |  |
|  |  | Q |  |  |  |  |  |  | A |
| SEQ ID NO: 4 Variant | F | L | S | Q | D | I | I | T | V |
|  |  |  |  |  |  |  |  |  | I |
|  |  |  |  |  |  |  |  |  | L |
|  |  |  |  |  |  |  |  |  | A |
|  |  | M |  |  |  |  |  |  |  |
|  |  | M |  |  |  |  |  |  | I |
|  |  | M |  |  |  |  |  |  | L |
|  |  | M |  |  |  |  |  |  | A |
|  |  | A |  |  |  |  |  |  |  |
|  |  | A |  |  |  |  |  |  | I |
|  |  | A |  |  |  |  |  |  | L |
|  |  | A |  |  |  |  |  |  | A |
|  |  | V |  |  |  |  |  |  |  |
|  |  | V |  |  |  |  |  |  | I |
|  |  | V |  |  |  |  |  |  | L |
|  |  | V |  |  |  |  |  |  | A |
|  |  | T |  |  |  |  |  |  |  |
|  |  | T |  |  |  |  |  |  | I |
|  |  | T |  |  |  |  |  |  | L |
|  |  | T |  |  |  |  |  |  | A |
|  |  | Q |  |  |  |  |  |  |  |
|  |  | Q |  |  |  |  |  |  | I |
|  |  | Q |  |  |  |  |  |  | L |
|  |  | Q |  |  |  |  |  |  | A |
| SEQ ID NO: 5 Variant | Y | L | Y | P | N | L | T | R | L |
|  |  |  |  |  |  |  |  |  | V |
|  |  |  |  |  |  |  |  |  | I |
|  |  |  |  |  |  |  |  |  | A |
|  |  | M |  |  |  |  |  |  | V |
|  |  | M |  |  |  |  |  |  | I |
|  |  | M |  |  |  |  |  |  |  |
|  |  | M |  |  |  |  |  |  | A |
|  |  | A |  |  |  |  |  |  | V |
|  |  | A |  |  |  |  |  |  | I |
|  |  | A |  |  |  |  |  |  |  |
|  |  | A |  |  |  |  |  |  | A |
|  |  | V |  |  |  |  |  |  | V |
|  |  | V |  |  |  |  |  |  | I |
|  |  | V |  |  |  |  |  |  |  |
|  |  | V |  |  |  |  |  |  | A |
|  |  | T |  |  |  |  |  |  | V |
|  |  | T |  |  |  |  |  |  | I |
|  |  | T |  |  |  |  |  |  |  |
|  |  | T |  |  |  |  |  |  | A |
|  |  | Q |  |  |  |  |  |  | V |
|  |  | Q |  |  |  |  |  |  | I |
|  |  | Q |  |  |  |  |  |  |  |
|  |  | Q |  |  |  |  |  |  | A |

Longer (elongated) peptides may also be suitable. It is possible that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

The peptides of the invention can be elongated by up to four amino acids, that is 1, 2, 3 or 4 amino acids can be added to either end in any combination between 4:0 and 0:4. Combinations of the elongations according to the invention can be found in Table 7.

TABLE 7

Combinations of the elongations of peptides of the invention

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

| N-terminus | C-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present invention may be identical to naturally occurring tumor-associated or tumor-specific epitopes or may include epitopes that differ by no more than four residues from the reference peptide, as long as they have substantially identical antigenic activity.

In an alternative embodiment, the peptide is elongated on either or both sides by more than 4 amino acids, preferably to a total length of up to 30 amino acids. This may lead to MHC class II binding peptides. Binding to MHC class II can be tested by methods known in the art.

Accordingly, the present invention provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the elongated class II binding peptides the length can also be 15, 16, 17, 18, 19, 20, 21 or 22 amino acids.

Of course, the peptide or variant according to the present invention will have the ability to bind to a molecule of the human major histocompatibility complex (MHC) class I or II. Binding of a peptide or a variant to a MHC complex may be tested by methods known in the art.

Preferably, when the T cells specific for a peptide according to the present invention are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 µM, and most preferably no more than about 10 µM. It is also preferred that the substituted peptide be recognized by T cells from more than one individual, at least two, and more preferably three individuals.

In a particularly preferred embodiment of the invention the peptide consists or consists essentially of an amino acid sequence according to SEQ ID NO: 1 to SEQ ID NO: 114.

"Consisting essentially of" shall mean that a peptide according to the present invention, in addition to the sequence according to any of SEQ ID NO: 1 to SEQ ID NO: 114 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is part of a fusion protein which comprises, for example, the 80 N-terminal amino acids of the HLA-DR antigen-associated invariant chain (p33, in the following "Ii") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells as described herein.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) (Meziere et al., 1997), incorporated herein by reference. This approach involves making pseudopeptides containing changes involving the backbone, and not the orientation of side chains. Meziere et al. (Meziere et al., 1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH═CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxy-carbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2004 (Lundblad, 2004), which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich (www.sigma-aldrich.com) provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other a-amino groups is, for example, useful in binding of peptides to surfaces or the cross-linking of proteins/peptides. Lysine is the site of attachment of poly (ethylene)glycol and the major site of modification in the glycosylation of proteins. Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1 hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitrile/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

In order to select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (Pinheiro et al., 2015) adjusting for multiple testing by False Discovery Rate (Benjamini and Hochberg, 1995).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural TUMAPs recorded from RCC samples (N=18*02-positive samples) with the fragmentation patterns of corresponding synthetic reference peptides of identical sequences. Since the peptides were directly identified as ligands of HLA molecules of primary tumors, these results provide direct evidence for the natural processing and presentation of the identified peptides on primary cancer tissue obtained from 18 RCC patients.

The discovery pipeline XPRESIDENT® v2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from RCC tissue samples were purified and HLA-associated peptides were isolated and analyzed by LC-MS (see examples). All TUMAPs contained in the present application were identified with this approach on primary RCC samples confirming their presentation on primary RCC.

TUMAPs identified on multiple RCC and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

Furthermore, the discovery pipeline XPRESIDENT® v2. allows for a direct absolute quantitation of MHC-, preferably HLA-restricted, peptide levels on cancer or other infected tissues. Briefly, the total cell count was calculated from the total DNA content of the analyzed tissue sample. The total peptide amount for a TUMAP in a tissue sample was measured by nanoLC-MS/MS as the ratio of the natural TUMAP and a known amount of an isotope-labelled version of the TUMAP, the so-called internal standard. The efficiency of TUMAP isolation was determined by spiking peptide:MHC complexes of all selected TUMAPs into the tissue lysate at the earliest possible point of the TUMAP isolation procedure and their detection by nanoLC-MS/MS following completion of the peptide isolation procedure. The total cell count and the amount of total peptide were calculated from triplicate measurements per tissue sample. The peptide-specific isolation efficiencies were calculated as an average from 10 spike experiments each measured as a triplicate (see Example 6 and Table 12).

The present invention provides peptides that are useful in treating cancers/tumors, preferably RCC that over- or exclusively present the peptides of the invention. These peptides were shown by mass spectrometry to be naturally presented by HLA molecules on primary human RCC samples.

Many of the source gene/proteins (also designated "full-length proteins" or "underlying proteins") from which the peptides are derived were shown to be highly over-expressed in cancer compared with normal tissues—"normal tissues" in relation to this invention shall mean either healthy kidney cells or other normal tissue cells, demonstrating a high degree of tumor association of the source genes (see Example 2). Moreover, the peptides themselves are strongly over-presented on tumor tissue—"tumor tissue" in relation to this invention shall mean a sample from a patient suffering from RCC, but not on normal tissues (see Example 1).

HLA-bound peptides can be recognized by the immune system, specifically T lymphocytes. T cells can destroy the cells presenting the recognized HLA/peptide complex, e.g. RCC cells presenting the derived peptides.

The peptides of the present invention have been shown to be capable of stimulating T cell responses and/or are over-presented and thus can be used for the production of antibodies and/or TCRs, such as soluble TCRs, according to the present invention (see Example 3, Example 4). Furthermore, the peptides when complexed with the respective MHC can be used for the production of antibodies and/or TCRs, in particular sTCRs, according to the present invention, as well. Respective methods are well known to the person of skill, and can be found in the respective literature as well. Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The present description further relates to T-cell receptors (TCRs) comprising an alpha chain and a beta chain ("alpha/beta TCRs"). Also provided are peptides capable of binding to TCRs and antibodies when presented by an MHC molecule. The present description also relates to nucleic acids, vectors and host cells for expressing TCRs and peptides of the present description; and methods of using the same.

The term "T-cell receptor" (abbreviated TCR) refers to a heterodimeric molecule comprising an alpha polypeptide chain (alpha chain) and a beta polypeptide chain (beta chain), wherein the heterodimeric receptor is capable of binding to a peptide antigen presented by an HLA molecule. The term also includes so-called gamma/delta TCRs.

In one embodiment the description provides a method of producing a TCR as described herein, the method comprising culturing a host cell capable of expressing the TCR under conditions suitable to promote expression of the TCR.

The description in another aspect relates to methods according to the description, wherein the antigen is loaded onto class I or II MHC molecules expressed on the surface of a suitable antigen-presenting cell or artificial antigen-presenting cell by contacting a sufficient amount of the antigen with an antigen-presenting cell or the antigen is loaded onto class I or II MHC tetramers by tetramerizing the antigen/class I or II MHC complex monomers.

The alpha and beta chains of alpha/beta TCR's, and the gamma and delta chains of gamma/delta TCRs, are generally regarded as each having two "domains", namely variable and constant domains. The variable domain consists of a concatenation of variable region (V), and joining region (J). The variable domain may also include a leader region (L). Beta and delta chains may also include a diversity region (D). The alpha and beta constant domains may also include C-terminal transmembrane (TM) domains that anchor the alpha and beta chains to the cell membrane.

With respect to gamma/delta TCRs, the term "TCR gamma variable domain" as used herein refers to the concatenation of the TCR gamma V (TRGV) region without leader region (L), and the TCR gamma J (TRGJ) region, and the term TCR gamma constant domain refers to the extracellular TRGC region, or to a C-terminal truncated TRGC sequence. Likewise the term "TCR delta variable domain" refers to the concatenation of the TCR delta V (TRDV) region without leader region (L) and the TCR delta D/J (TRDD/TRDJ) region, and the term "TCR delta constant domain" refers to the extracellular TRDC region, or to a C-terminal truncated TRDC sequence.

TCRs of the present description preferably bind to a peptide-HLA molecule complex with a binding affinity (KD) of about 100 μM or less, about 50 μM or less, about 25 M or less, or about 10 μM or less. More preferred are high affinity TCRs having binding affinities of about 1 μM or less, about 100 nM or less, about 50 nM or less, about 25 nM or less. Non-limiting examples of preferred binding affinity ranges for TCRs of the present invention include about 1 nM to about 10 nM; about 10 nM to about 20 nM; about 20 nM to about 30 nM; about 30 nM to about 40 nM; about 40 nM to about 50 nM; about 50 nM to about 60 nM; about 60 nM to about 70 nM; about 70 nM to about 80 nM; about 80 nM to about 90 nM; and about 90 nM to about 100 nM.

As used herein in connect with TCRs of the present description, "specific binding" and grammatical variants thereof are used to mean a TCR having a binding affinity (KD) for a peptide-HLA molecule complex of 100 μM or less.

Alpha/beta heterodimeric TCRs of the present description may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned above, alpha/beta heterodimeric TCRs of the present description may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

TCRs of the present description may comprise a detectable label selected from the group consisting of a radionuclide, a fluorophore and biotin. TCRs of the present description may be conjugated to a therapeutically active agent, such as a radionuclide, a chemotherapeutic agent, or a toxin.

In an embodiment, a TCR of the present description having at least one mutation in the alpha chain and/or having at least one mutation in the beta chain has modified glycosylation compared to the unmutated TCR.

In an embodiment, a TCR comprising at least one mutation in the TCR alpha chain and/or TCR beta chain has a binding affinity for, and/or a binding half-life for, an peptide-HLA molecule complex, which is at least double that of a TCR comprising the unmutated TCR alpha chain and/or unmutated TCR beta chain. Affinity-enhancement of tumor-specific TCRs, and its exploitation, relies on the existence of a window for optimal TCR affinities.

The existence of such a window is based on observations that TCRs specific for HLA-A2-restricted pathogens have KD values that are generally about 10-fold lower when compared to TCRs specific for HLA-A2-restricted tumor-associated self-antigens. It is now known, although tumor antigens have the potential to be immunogenic, because tumors arise from the individual's own cells only mutated proteins or proteins with altered translational processing will be seen as foreign by the immune system. Antigens that are upregulated or overexpressed (so called self-antigens) will not necessarily induce a functional immune response against the tumor: T-cells expressing TCRs that are highly reactive to these antigens will have been negatively selected within the thymus in a process known as central tolerance, meaning that only T-cells with low-affinity TCRs for self-antigens remain. Therefore, affinity of TCRs or variants of the present description to the peptides according to the invention can be enhanced by methods well known in the art.

The present description further relates to a method of identifying and isolating a TCR according to the present description, said method comprising incubating PBMCs from HLA-A*02-negative healthy donors with A2/peptide monomers, incubating the PBMCs with tetramer-phycoerythrin (PE) and isolating the high avidity T-cells by fluorescence activated cell sorting (FACS)-Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with peptide of interest, incubating PBMCs obtained from the transgenic mice with tetramer-phycoerythrin (PE), and isolating the high avidity T-cells by fluorescence activated cell sorting (FACS)-Calibur analysis.

In one aspect, to obtain T-cells expressing TCRs of the present description, nucleic acids encoding TCR-alpha and/or TCR-beta chains of the present description are cloned into expression vectors, such as gamma retrovirus or lentivirus. The recombinant viruses are generated and then tested for functionality, such as antigen specificity and functional avidity. An aliquot of the final product is then used to transduce the target T-cell population (generally purified from patient PBMCs), which is expanded before infusion into the patient. In another aspect, to obtain T-cells expressing TCRs of the present description, TCR RNAs are synthesized by techniques known in the art, e.g., in vitro transcription systems. The in vitro-synthesized TCR RNAs are then introduced into primary CD8+ T-cells obtained from healthy donors by electroporation to re-express tumor specific TCR-alpha and/or TCR-beta chains.

To increase the expression, nucleic acids encoding TCRs of the present description may be operably linked to strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter, elongation factor (EF)-1a and the spleen focus-forming virus (SFFV) promoter. In a preferred embodiment, the promoter is heterologous to the nucleic acid being expressed. In addition to strong promoters, TCR expression cassettes of the present description may contain additional elements that can enhance transgene expression, including a central polypurine tract (cPPT), which promotes the nuclear translocation of lentiviral constructs (Follenzi et al., 2000), and the woodchuck hepatitis virus posttranscriptional regulatory element (wPRE), which increases the level of transgene expression by increasing RNA stability (Zufferey et al., 1999).

The alpha and beta chains of a TCR of the present invention may be encoded by nucleic acids located in separate vectors, or may be encoded by polynucleotides located in the same vector.

Achieving high-level TCR surface expression requires that both the TCR-alpha and TCR-beta chains of the introduced TCR be transcribed at high levels. To do so, the TCR-alpha and TCR-beta chains of the present description may be cloned into bi-cistronic constructs in a single vector, which has been shown to be capable of over-coming this obstacle. The use of a viral intrariboscomal entry site (IRES) between the TCR-alpha and TCR-beta chains results in the coordinated expression of both chains, because the TCR-alpha and TCR-beta chains are generated from a single transcript that is broken into two proteins during translation, ensuring that an equal molar ratio of TCR-alpha and TCR-beta chains are produced. (Schmitt et al. 2009).

Nucleic acids encoding TCRs of the present description may be codon optimized to increase expression from a host cell. Redundancy in the genetic code allows some amino acids to be encoded by more than one codon, but certain codons are less "op-timal" than others because of the relative availability of matching tRNAs as well as other factors (Gustafsson et al., 2004). Modifying the TCR-alpha and TCR-beta gene sequences such that each amino acid is encoded by the optimal codon for mammalian gene expression, as well as eliminating mRNA instability motifs or cryptic splice sites, has been shown to significantly enhance TCR-alpha and TCR-beta gene expression (Scholten et al., 2006).

Furthermore, mispairing between the introduced and endogenous TCR chains may result in the acquisition of specificities that pose a significant risk for autoimmunity. For example, the formation of mixed TCR dimers may reduce the number of CD3 molecules available to form properly paired TCR complexes, and therefore can significantly decrease the functional avidity of the cells expressing the introduced TCR (Kuball et al., 2007).

To reduce mispairing, the C-terminus domain of the introduced TCR chains of the present description may be modified in order to promote interchain affinity, while decreasing the ability of the introduced chains to pair with the endogenous TCR. These strategies may include replacing the human TCR-alpha and TCR-beta C-terminus domains with their murine counterparts (murinized C-terminus domain); generating a second interchain disulfide bond in the C-terminus domain by introducing a second cysteine residue into both the TCR-alpha and TCR-beta chains of the introduced TCR (cysteine modification); swapping interacting residues in the TCR-alpha and TCR-beta chain C-terminus domains ("knob-in-hole"); and fusing the variable domains of the TCR-alpha and TCR-beta chains directly to CD3 (CD3 fusion). (Schmitt et al. 2009).

In an embodiment, a host cell is engineered to express a TCR of the present description. In preferred embodiments, the host cell is a human T-cell or T-cell progenitor. In some embodiments the T-cell or T-cell progenitor is obtained from a cancer patient. In other embodiments the T-cell or T-cell progenitor is obtained from a healthy donor. Host cells of the present description can be allogeneic or autologous with respect to a patient to be treated. In one embodiment, the host is a gamma/delta T-cell transformed to express an alpha/beta TCR.

A "pharmaceutical composition" is a composition suitable for administration to a human being in a medical setting. Preferably, a pharmaceutical composition is sterile and produced according to GMP guidelines.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

Preferably, the medicament of the present invention is an immunotherapeutic such as a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and (Longenecker et al., 1993)). The peptide may also be tagged, may be a fusion protein, or may be a hybrid molecule. The peptides whose sequence is given in the present invention are expected to stimulate CD4 or CD8 T cells. However, stimulation of CD8 T cells is more efficient in the presence of help provided by CD4 T-helper cells. Thus, for MHC Class I epitopes that stimulate CD8 T cells the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth SEQ ID No. 1 to SEQ ID No. 114, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by Saiki R K, et al. (Saiki et al., 1988).This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed, for example, in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N. J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them. These constructs can also be used for cancer therapy, and may induce immune responses both involving MHC I and MHC II.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbas and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al. (Cohen et al., 1972) and (Green and Sambrook, 2012). Transformation of yeast cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 pg and 1.5 mg, preferably 125 pg to 500 pg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CD8-positive T cells and helper-T (TH) cells to an antigen, and would thus be considered useful in the medicament of the present invention. Suitable adjuvants include, but are not limited to, 1018 ISS, aluminum salts, AMPLIVAX®, AS15, BCG, CP-870, 893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonol®, poly-(ICLC), poly(IC-R), poly(I:C12U), non-CpG bacterial DNA or RNA as well as immunoactive small molecules and antibodies such as cyclophosphamide, sunitinib, Bevacizumab@, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM- CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonol®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomatous or cancerous diseases. Exemplary formulations can be found in, for example, EP2112253.

It is important to realize that the immune response triggered by the vaccine according to the invention attacks the cancer in different cell-stages and different stages of development. Furthermore different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Banchereau et al., 2001; Walter et al., 2012).

As used herein, the term "scaffold" refers to a molecule that specifically binds to an (e.g. antigenic) determinant. In one embodiment, a scaffold is able to direct the entity to which it is attached (e.g. a (second) antigen binding moiety) to a target site, for example to a specific type of tumor cell or tumor stroma bearing the antigenic determinant (e.g. the complex of a peptide with MHC, according to the application at hand). In another embodiment a scaffold is able to activate signaling through its target antigen, for example a T cell receptor complex antigen. Scaffolds include but are not limited to antibodies and fragments thereof, antigen binding domains of an antibody, comprising an antibody heavy chain variable region and an antibody light chain variable region, binding proteins comprising at least one ankyrin repeat motif and single domain antigen binding (SDAB) molecules, aptamers, (soluble) TCRs and (modified) cells such as allogenic or autologous T cells. To assess whether a molecule is a scaffold binding to a target, binding assays can be performed.

"Specific" binding means that the scaffold binds the peptide-MHC-complex of interest better than other naturally occurring peptide-MHC-complexes, to an extent that a scaffold armed with an active molecule that is able to kill a cell bearing the specific target is not able to kill another cell without the specific target but presenting other peptide-MHC complex(es). Binding to other peptide-MHC complexes is irrelevant if the peptide of the cross-reactive peptide-MHC is not naturally occurring, i.e. not derived from the human HLA-peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labelling which provides that the bound scaffold can be detected by determining the presence or absence of a signal provided by the label. For example, the scaffold can be labelled with a fluorescent dye or any other applicable cellular marker molecule. Such marker molecules are well known in the art. For example a fluorescence-labelling, for example provided by a fluorescence dye, can provide a visualization of the bound aptamer by fluorescence or laser scanning microscopy or flow cytometry.

Each scaffold can be conjugated with a second active molecule such as for example IL-21, anti-CD3, and anti-CD28.

For further information on polypeptide scaffolds see for example the background section of WO 2014/071978A1 and the references cited therein.

The present invention further relates to aptamers. Aptamers (see for example WO 2014/191359 and the literature as cited therein) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. Further, it could be shown that some of the aptamers are taken up by tumor cells and thus can function as molecular vehicles for the targeted delivery of anti-cancer agents such as siRNA into tumor cells.

Aptamers can be selected against complex targets such as cells and tissues and complexes of the peptides comprising, preferably consisting of, a sequence according to any of SEQ ID NO:1 to SEQ ID NO: 114, according to the invention at hand with the MHC molecule, using the cell-SELEX (Systematic Evolution of Ligands by Exponential enrichment) technique.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Respective methods for producing such antibodies and single chain class I major histocompatibility complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003), which for the purposes of the present invention are all explicitly incorporated by reference in their entireties.

Preferably, the antibody is binding with a binding affinity of below 20 nanomolar, preferably of below 10 nanomolar, to the complex, which is also regarded as "specific" in the context of the present invention.

The present invention relates to a peptide comprising a sequence that is selected from the group consisting of SEQ ID NO: 1 to SEQ ID NO: 114, or a variant thereof which is at least 88% homologous (preferably identical) to SEQ ID NO: 1 to SEQ ID NO: 114 or a variant thereof that induces T cells cross-reacting with said peptide, wherein said peptide is not the underlying full-length polypeptide.

The present invention further relates to a peptide comprising a sequence that is selected from the group consisting of SEQ ID NO: 1 to SEQ ID NO: 114 or a variant thereof which is at least 88% homologous (preferably identical) to SEQ ID NO: 1 to SEQ ID NO: 114, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) class-I or -II.

The present invention further relates to the peptides according to the invention wherein the peptide consists or consists essentially of an amino acid sequence according to SEQ ID NO: 1 to SEQ ID NO: 114.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

The present invention further relates to a nucleic acid, encoding the peptides according to the invention, provided that the peptide is not the complete (full) human protein.

The present invention further relates to the nucleic acid according to the invention that is DNA, cDNA, PNA, RNA or combinations thereof.

The present invention further relates to an expression vector capable of expressing a nucleic acid according to the present invention.

The present invention further relates to a peptide according to the present invention, a nucleic acid according to the present invention or an expression vector according to the present invention for use in medicine, in particular in the treatment of RCC.

The present invention further relates to a host cell comprising a nucleic acid according to the invention or an expression vector according to the invention.

The present invention further relates to the host cell according to the present invention that is an antigen presenting cell, and preferably a dendritic cell.

The present invention further relates to a method of producing a peptide according to the present invention, said method comprising culturing the host cell according to the present invention, and isolating the peptide from said host cell or its culture medium.

The present invention further relates to the method according to the present invention, where-in the antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 114 or said variant amino acid sequence.

The present invention further relates to activated T cells, produced by the method according to the present invention, wherein said T cells selectively recognizes a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as according to the present invention.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament. The present invention further relates to a use according to the present invention, wherein the medicament is active against cancer.

The present invention further relates to a use according to the invention, wherein the medicament is a vaccine. The present invention further relates to a use according to the invention, wherein the medicament is active against cancer.

The present invention further relates to a use according to the invention, wherein said cancer cells are RCC cells or other solid or haematological tumor cells such as lung cancer, brain cancer, stomach cancer, colon or rectal cancer, liver cancer, pancreatic cancer, prostate cancer, leukemias, breast cancer, melanoma, ovarian cancer, and. esophageal cancer.

The present invention further relates to particular marker proteins and biomarkers based on the peptides according to the present invention, herein called "targets" that can be used in the diagnosis and/or prognosis of RCC. The present invention also relates to the use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g. CDRs, Fv, Fab and Fc fragments) or polymers of those immunoglobulin molecules and humanized versions of immunoglobulin molecules, as long as they exhibit any of the desired properties (e.g., specific binding of a RCC marker (poly)peptide, delivery of a toxin to a RCC cell expressing a cancer marker gene at an increased level, and/or inhibiting the activity of a RCC marker polypeptide) according to the invention.

Whenever possible, the antibodies of the invention may be purchased from commercial sources. The antibodies of the invention may also be generated using well-known methods. The skilled artisan will understand that either full length RCC marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a peptide according to the present invention, such as a peptide according to SEQ ID NO: 1 to SEQ ID NO: 114 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the RCC marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Greenfield, 2014 (Greenfield, 2014)). For example, the antibodies may be tested in ELISA assays or, Western blots, immunohistochemical staining of formalin-fixed cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a F(ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered.

A typical daily dosage of the antibody used alone might range from about 1 (pg/kg to up to 100 mg/kg of body weight or more per day, depending on the factors mentioned above.

Following administration of an antibody, preferably for treating RCC, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of cancer.

It is a further aspect of the invention to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), and domains recruiting effector cells such as an anti-CD3 domain, etc., in order to execute particular functions on target cells. Moreover, it can be expressed in T cells used for adoptive transfer. Further information can be found in WO 2004/033685A1 and WO 2004/074322A1. A combination of sTCRs is described in WO 2012/056407A1. Additional methods for the production are disclosed in WO 2013/057586A1.

It is a further aspect of the invention to provide a TCR, for example a soluble T-cell receptor (sTCR) recognizing a specific peptide-MHC complex as disclosed herein.

In addition, the peptides and/or the TCRs or antibodies or other binding molecules of the present invention can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$O, $^{131}$I, $^{3}$H, $^{32}$P or $^{35}$S) SO that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than 1×10 µM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and Drosophila cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the Drosophila cell line Schneider line 2 is available from the ATCC under Catalogue No CRL 19863; the mouse RMA-S cell line is described in Ljunggren et al. (Ljunggren and Karre, 1985).

Preferably, before transfection the host cell expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T cells are CD8-positive T cells.

If an antigen-presenting cell is transfected to express such an epitope, preferably the cell comprises an expression vector capable of expressing a peptide containing SEQ ID NO: 1 to SEQ ID NO: 114 and/or SEQ ID NO: 115 to SEQ ID NO: 151 or a variant amino acid sequence thereof.

A number of other methods may be used for generating T cells in vitro. For example, autologous tumor-infiltrating lymphocytes can be used in the generation of CTL. Plebanski et al. (Plebanski et al., 1995) made use of autologous peripheral blood lymphocytes (PLBs) in the preparation of T cells. Furthermore, the production of autologous T cells by pulsing dendritic cells with peptide or polypeptide, or via infection with recombinant virus is possible. Also, B cells can be used in the production of autologous T cells. In addition, macrophages pulsed with peptide or polypeptide, or infected with recombinant virus, may be used in the preparation of autologous T cells. S. Walter et al. (Walter et al., 2003) describe the in vitro priming of T cells by using artificial antigen presenting cells (aAPCs), which is also a suitable way for generating T cells against the peptide of choice. In the present invention, aAPCs were generated by the coupling of preformed MHC:peptide complexes to the surface of polystyrene particles (microbeads) by biotin:streptavidin biochemistry. This system permits the exact control of the MHC density on aAPCs, which allows to selectively eliciting high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore such aAPC-based systems often require the addition of appropriate soluble factors, e. g. cytokines, like interleukin-12.

Allogeneic cells may also be used in the preparation of T cells and a method is described in detail in WO 97/26328, incorporated herein by reference. For example, in addition to Drosophila cells and T2 cells, other cells may be used to present antigens such as CHO cells, baculovirus-infected insect cells, bacteria, yeast, and vaccinia-infected target cells. In addition plant viruses may be used (see, for example, Porta et al. (Porta et al., 1994) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO: 114.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to normal levels of expression or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above. Protocols for this so-called adoptive transfer of T cells are also well known in the art. Reviews can be found in: Gattioni et al. and Morgan et al. (Gattinoni et al., 2006; Morgan et al., 2006).

Another aspect of the present invention includes the use of the peptides complexed with MHC to generate a T-cell receptor whose nucleic acid is cloned and is introduced into a host cell, preferably a T cell. This engineered T cell can then be transferred to a patient for therapy of cancer.

Any molecule of the invention, i.e. the peptide, nucleic acid, antibody, expression vector, cell, activated T cell, T-cell receptor or the nucleic acid encoding it, is useful for the treatment of disorders, characterized by cells escaping an immune response. Therefore any molecule of the present invention may be used as medicament or in the manufacture of a medicament. The molecule may be used by itself or combined with other molecule(s) of the invention or (a) known molecule(s).

The present invention is further directed at a kit comprising:
(a) a container containing a pharmaceutical composition as described above, in solution or in lyophilized form;
(b) optionally a second container containing a diluent or reconstituting solution for the lyophilized formulation; and
(c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 pg) and preferably not more than 3 mg/mL/peptide (=1500 pg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably, the administration is s.c., and most preferably i.d. administration may be by infusion pump.

Since the peptides of the invention were isolated from RCC, the medicament of the invention is preferably used to treat RCC.

The present invention further relates to a method for producing a personalized pharmaceutical for an individual patient comprising manufacturing a pharmaceutical composition comprising at least one peptide selected from a warehouse of pre-screened TUMAPs, wherein the at least one peptide used in the pharmaceutical composition is selected for suitability in the individual patient. In one embodiment, the pharmaceutical composition is a vaccine. The method could also be adapted to produce T cell clones for down-stream applications, such as TCR isolations, or soluble antibodies, and other treatment options.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group or set of peptides that have been pre-screened for immunogenicity and/or over-presentation in a particular tumor type. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored. The warehouse (e.g. in the form of a database) is composed of tumor-associated peptides which were highly overexpressed in the tumor tissue of RCC patients with various HLA-A HLA-B and HLA-C alleles. It may contain MHC class I and MHC class II peptides or elongated MHC class I peptides. In addition to the tumor associated peptides collected from several RCC tissues, the warehouse may contain HLA-A*02 and HLA-A*24 marker peptides. These peptides allow comparison of the magnitude of T-cell immunity induced by TUMAPS in a quantitative manner and hence allow important conclusion to be drawn on the capacity of the vaccine to elicit anti-tumor responses. Secondly, they function as important positive control peptides derived from a "non-self" antigen in the case that any vaccine-induced T-cell responses to TUMAPs derived from "self" antigens in a patient are not observed. And thirdly, it may allow conclusions to be drawn, regarding the status of immunocompetence of the patient.

TUMAPs for the warehouse are identified by using an integrated functional genomics approach combining gene expression analysis, mass spectrometry, and T-cell immunology (XPresident®). The approach assures that only TUMAPs truly present on a high percentage of tumors but not or only minimally expressed on normal tissue, are chosen for further analysis. For initial peptide selection, RCC samples from patients and blood from healthy donors were analyzed in a stepwise approach:

1. HLA ligands from the malignant material were identified by mass spectrometry
2. Genome-wide messenger ribonucleic acid (mRNA) expression analysis was used to identify genes over-expressed in the malignant tissue (RCC) compared with a range of normal organs and tissues
3. Identified HLA ligands were compared to gene expression data. Peptides over-presented or selectively presented on tumor tissue, preferably encoded by selectively expressed or over-expressed genes as detected in step 2 were considered suitable TUMAP candidates for a multi-peptide vaccine.
4. Literature research was performed in order to identify additional evidence supporting the relevance of the identified peptides as TUMAPs
5. The relevance of over-expression at the mRNA level was confirmed by redetection of selected TUMAPs from step 3 on tumor tissue and lack of (or infrequent) detection on healthy tissues.
6. In order to assess, whether an induction of in vivo T-cell responses by the selected peptides may be feasible, in vitro immunogenicity assays were performed using human T cells from healthy donors as well as from RCC patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed, the warehouse allows a significantly higher matching of the actual expression of antigens in the tumor with the vaccine. Selected single or combinations of several "off-the-shelf" peptides will be used for each patient in a multitarget approach. In theory an approach based on selection of e.g. 5 different antigenic peptides from a library of 50 would already lead to approximately 17 million possible drug product (DP) compositions.

In an aspect, the peptides are selected for inclusion in the vaccine based on their suitability for the individual patient based on the method according to the present invention as described herein, or as below.

The HLA phenotype, transcriptomic and peptidomic data is gathered from the patient's tumor material, and blood samples to identify the most suitable peptides for each patient containing "warehouse" and patient-unique (i.e. mutated) TUMAPs. Those peptides will be chosen, which are selectively or over-expressed in the patients tumor and, where possible, show strong in vitro immunogenicity if tested with the patients' individual PBMCs.

Preferably, the peptides included in the vaccine are identified by a method comprising: (a) identifying tumor-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumor-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

In addition to, or as an alternative to, selecting peptides using a warehousing (database) model, TUMAPs may be identified in the patient de novo, and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumina). Additionally, tumor mRNA is sequenced for direct quantification of gene expression and validation that mutated genes are expressed in the patients' tumors. The resultant millions of sequence reads are processed through software algorithms. The output list contains mutations and gene expression. Tumor-specific somatic mutations are determined by comparison with the PBMC-derived germline variations and prioritized. The de novo identified peptides can then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the method as described above; (b) comparing the peptides identified in a) with a warehouse of peptides that have been prescreened for immunogenicity and overpresentation in tumors as compared to corresponding normal tissue; (c) selecting at least one peptide from the warehouse that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides for a personalized peptide based vaccine are selected, the vaccine is produced. The vaccine preferably is a liquid formulation consisting of the individual peptides dissolved in between 20-40% DMSO, preferably about 30-35% DMSO, such as about 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 µm sterile filter. The final bulk solution is obtained.

Final bulk solution is filled into vials and stored at −20° C. until use. One vial contains 700 µL solution, containing 0.578 mg of each peptide. Of this, 500 µL (approx. 400 pg per peptide) will be applied for intradermal injection.

In addition to being useful for treating cancer, the peptides of the present invention are also useful as diagnostics. Since the peptides were generated from RCC cells and since it was determined that these peptides are not or at lower levels present in normal tissues, these peptides can be used to diagnose the presence of a cancer.

The presence of claimed peptides on tissue biopsies in blood samples can assist a pathologist in diagnosis of cancer. Detection of certain peptides by means of antibodies, mass spectrometry or other methods known in the art can tell the pathologist that the tissue sample is malignant or inflamed or generally diseased, or can be used as a biomarker for RCC. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate response markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The present invention will now be described in the following examples which describe preferred embodiments thereof, and with reference to the accompanying figures, nevertheless, without being limited thereto. For the purposes of the present invention, all references as cited herein are incorporated by reference in their entireties.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A) Gene: SLC17A3, Peptide: ALIVSLPYL (SEQ ID NO.: 1)—Tissues from left to right: 1 adipose tissues, 3 adrenal glands, 2 arteries, 3 bone marrows, 7 brains, 3 breasts, 13 colons, 1 ovary, 1 duodenum 4 esophagi, 2 gallbladders, 3 hearts, 4 leukocyte samples, 19 livers, 43 lungs, 1 lymph node, 1 ovary, 6 pancreas, 2 peripheral nerves, 1 peritoneum, 1 pituitary gland, 3 pleuras, 1 prostate, 6 recti, 3 skeletal muscles, 3 skins, 2 small intestines, 4 spleens, 5 stomachs, 1 testis, 2 thymi, 3 thyroid glands, 2 uteri, 2 veins, 12 kidneys, 18 RCC. The peptide was also found on liver cancer (not shown). FIG. 1H) Gene: HTR, Peptide: FIADVVEKI (SEQ ID NO.: 33)—Tissues from left to right: 16 cancer tissues (1 brain cancer, 1 breast cancer, 1 esophageal cancer, 3 kidney cancers, 1 leukocytic leukemia cancer, 5 lung cancers, 1 lymph node cancer, 2 ovarian cancers, 1 pancreas cancer). FIG. 1N) Gene: TIMP1, Peptide: KLQDGLLHI (SEQ ID NO.: 103)—Tissues from left to right: 1 cell line (1 blood cells), 29 cancer tissues (2 brain cancers, 5 colon cancers, 3 kidney cancers, 1 liver cancer, 4 lung cancers, 2 lymph node cancers, 3 ovarian cancers, 1 pancreas cancer, 1 rectum cancer, 6 skin cancers, 1 testis cancer).

FIG. 2A) GAL3ST1; FIG. 2B) EGLN3; FIG. 2C) APOL1; and FIG. 2D) MET.

EXAMPLES

Example 1

Figure 1A:
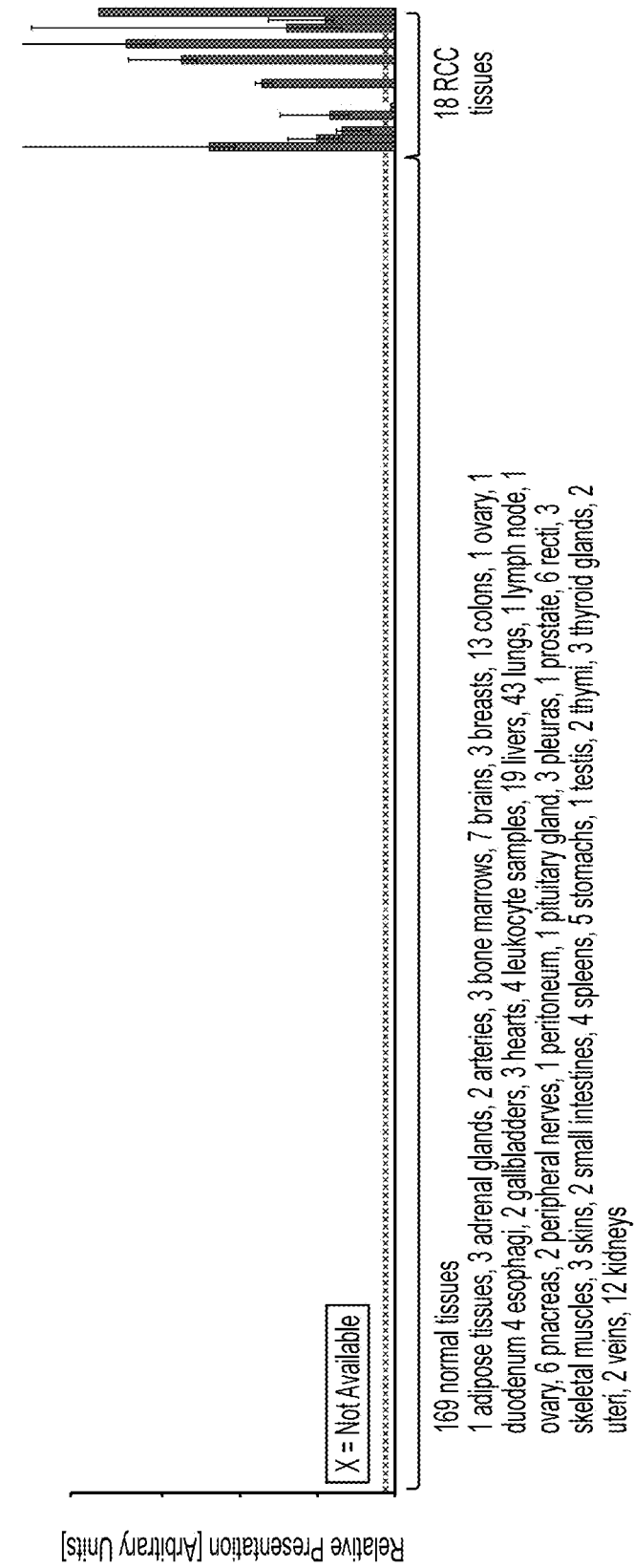
FIGS. 1A to 1N show the over-presentation of various peptides in normal tissues and RCC.
Figure 1B:
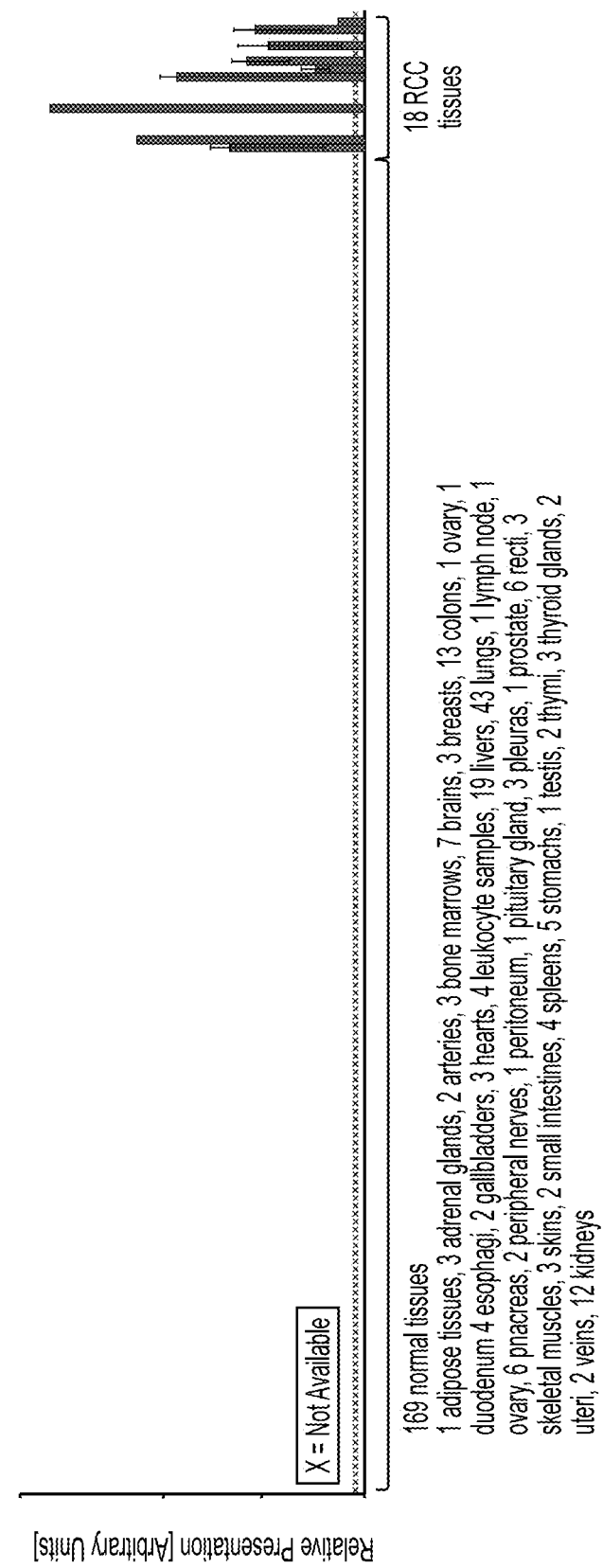
FIG. 1B) Gene: SOGA2, Peptide: YLEEDVYQL (SEQ ID NO.: 128)—Tissues from left to right: 1 adipose tissues, 3 adrenal glands, 2 arteries, 3 bone marrows, 7 brains, 3 breasts, 13 colons, 1 ovary, 1 duodenum 4 esophagi, 2 gallbladders, 3 hearts, 4 leukocyte samples, 19 livers, 43 lungs, 1 lymph node, 1 ovary, 6 pancreas, 2 peripheral nerves, 1 peritoneum, 1 pituitary gland, 3 pleuras, 1 prostate, 6 recti, 3 skeletal muscles, 3 skins, 2 small intestines, 4 spleens, 5 stomachs, 1 testis, 2 thymi, 3 thyroid glands, 2 uteri, 2 veins, 12 kidneys, 18 RCC. The peptide was also found on pancreatic cancer, ovarian cancers, stomach cancer, and lung cancer (not shown).
Figure 1C:
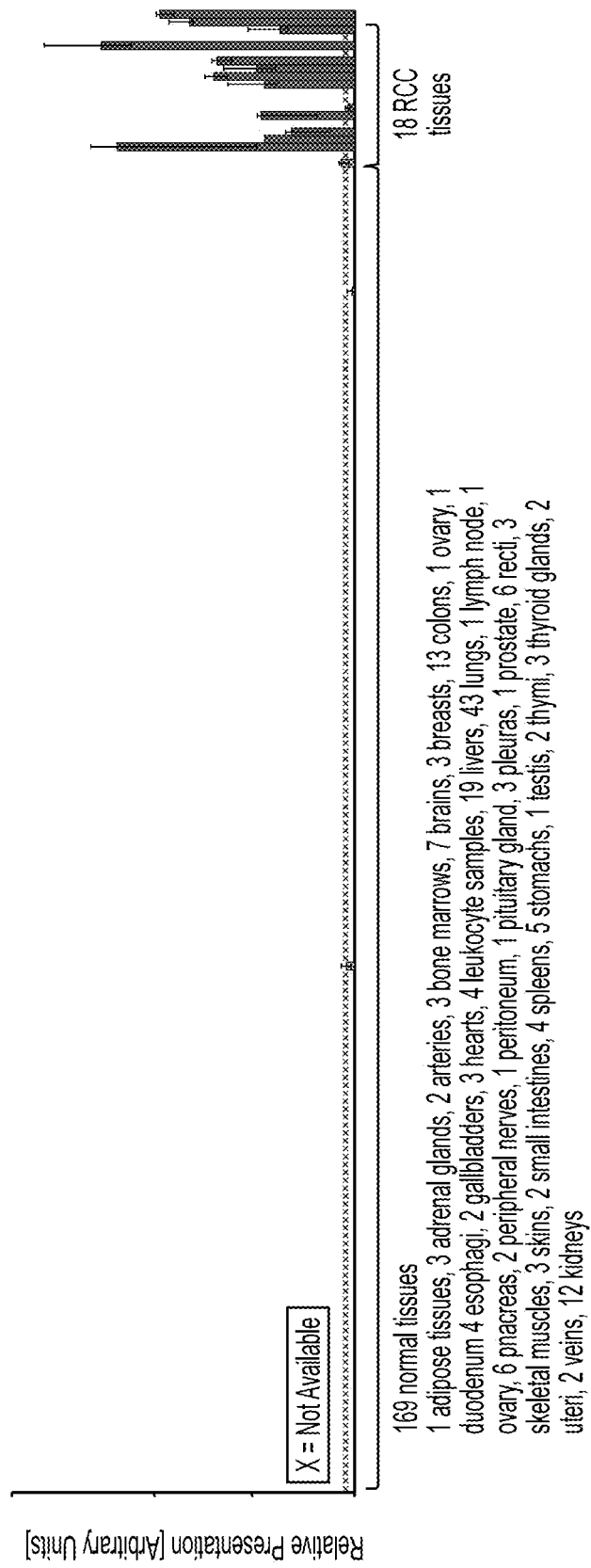
FIG. 1C) Gene: SEMA5B, Peptide: ALDPSGNQLI (SEQ ID NO.: 12)—Tissues from left to right: 1 adipose tissues, 3 adrenal glands, 2 arteries, 3 bone marrows, 7 brains, 3 breasts, 13 colons, 1 ovary, 1 duodenum 4 esophagi, 2 gallbladders, 3 hearts, 4 leukocyte samples, 19 livers, 43 lungs, 1 lymph node, 1 ovary, 6 pancreas, 2 peripheral nerves, 1 peritoneum, 1 pituitary gland, 3 pleuras, 1 prostate, 6 recti, 3 skeletal muscles, 3 skins, 2 small intestines, 4 spleens, 5 stomachs, 1 testis, 2 thymi, 3 thyroid glands, 2 uteri, 2 veins, 12 kidneys, 18 RCC. The peptide was also found on ovarian cancer, brain cancer, and lung cancer (not shown).
Figure 1D:
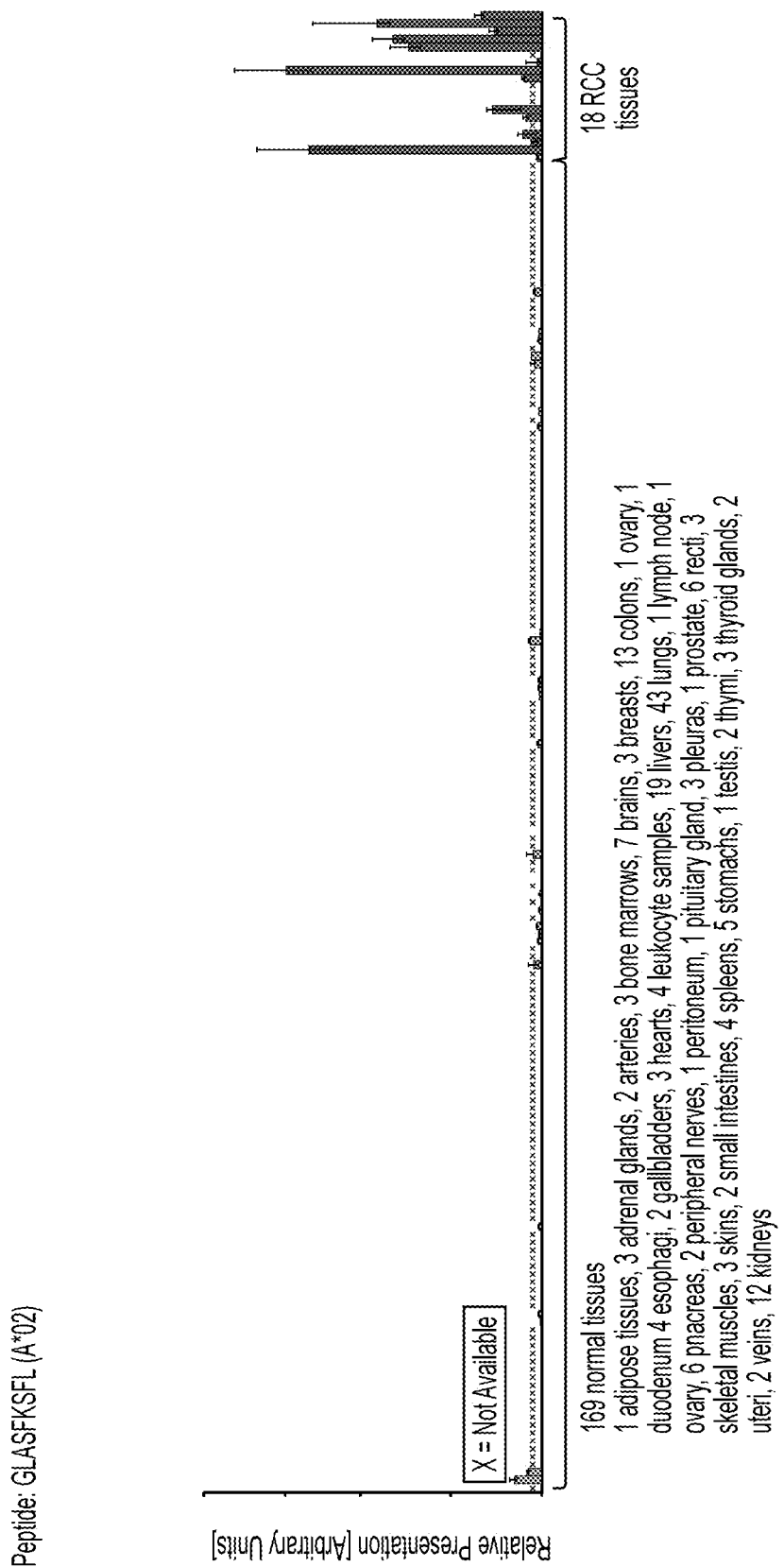
FIG. 1D) Gene: RGS5, Peptide: GLASFKSFL (SEQ ID NO.: 8)—Tissues from left to right: 1 adipose tissues, 3 adrenal glands, 2 arteries, 3 bone marrows, 7 brains, 3 breasts, 13 colons, 1 ovary, 1 duodenum 4 esophagi, 2 gallbladders, 3 hearts, 4 leukocyte samples, 19 livers, 43 lungs, 1 lymph node, 1 ovary, 6 pancreas, 2 peripheral nerves, 1 peritoneum, 1 pituitary gland, 3 pleuras, 1 prostate, 6 recti, 3 skeletal muscles, 3 skins, 2 small intestines, 4 spleens, 5 stomachs, 1 testis, 2 thymi, 3 thyroid glands, 2 uteri, 2 veins, 12 kidneys, 18 RCC. The peptide was also found on prostate cancer, breast cancer, colon cancer, liver cancer, melanoma, ovarian cancer, esophageal cancer, pancreatic cancer, brain cancer, stomach cancer and lung cancer (not shown).
Figure 1E:
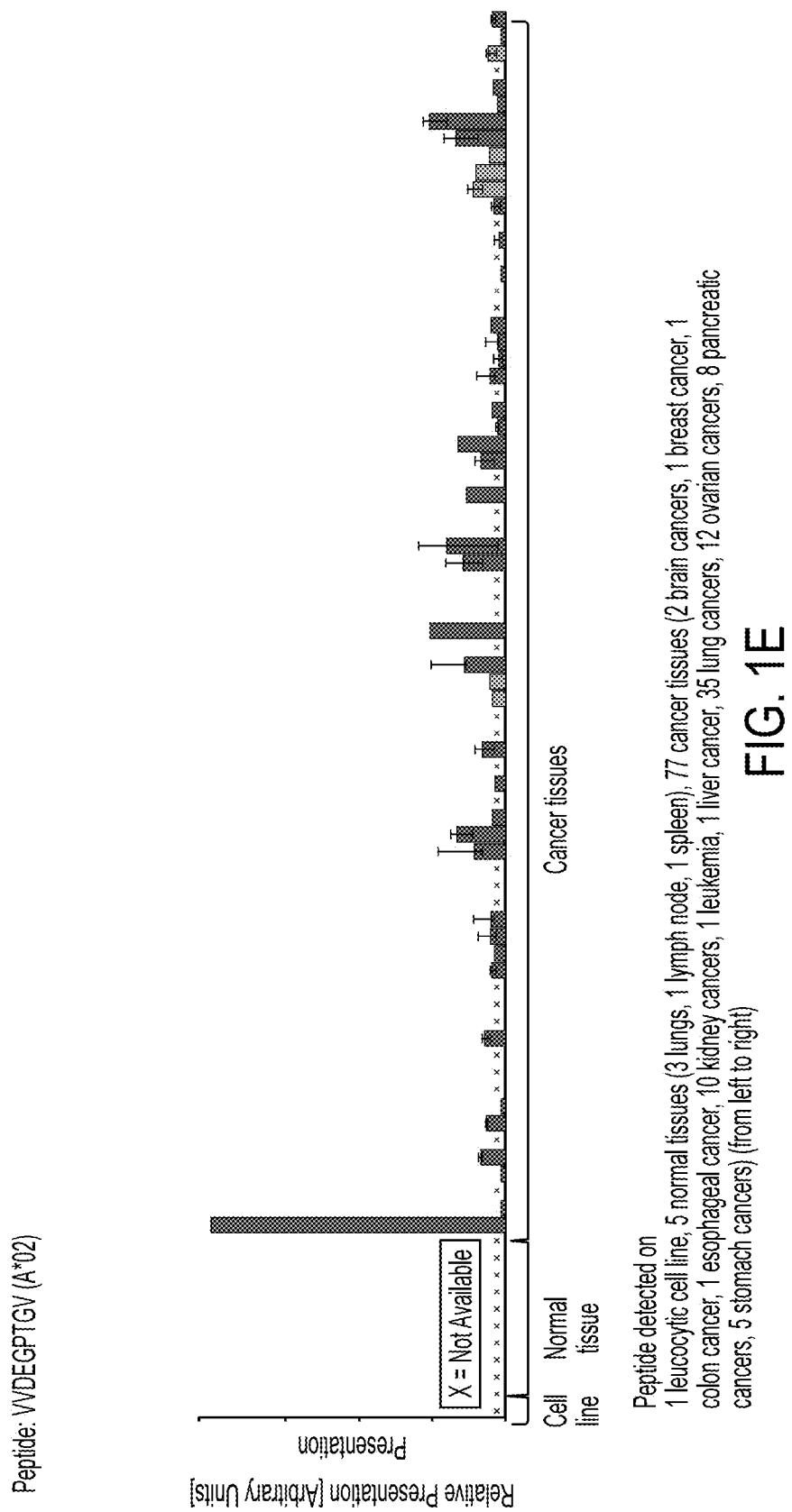
FIG. 1E) Gene: SLC16A3, Peptide: VVDEGPTGV (SEQ ID NO.: 135)—Tissues from left to right: 1 leucocytic cell line, 5 normal tissues (3 lungs, 1 lymph node, 1 spleen), 77 cancer tissues (2 brain cancers, 1 breast cancer, 1 colon cancer, 1 esophageal cancer, 10 kidney cancers, 1 leukemia, 1 liver cancer, 35 lung cancers, 12 ovarian cancers, 8 pancreatic cancers, 5 stomach cancers). Samples without peptide presentation are not shown. The normal (healthy) tissue panel tested was the same as in FIGS. 1A-1D.
Figure 1F:
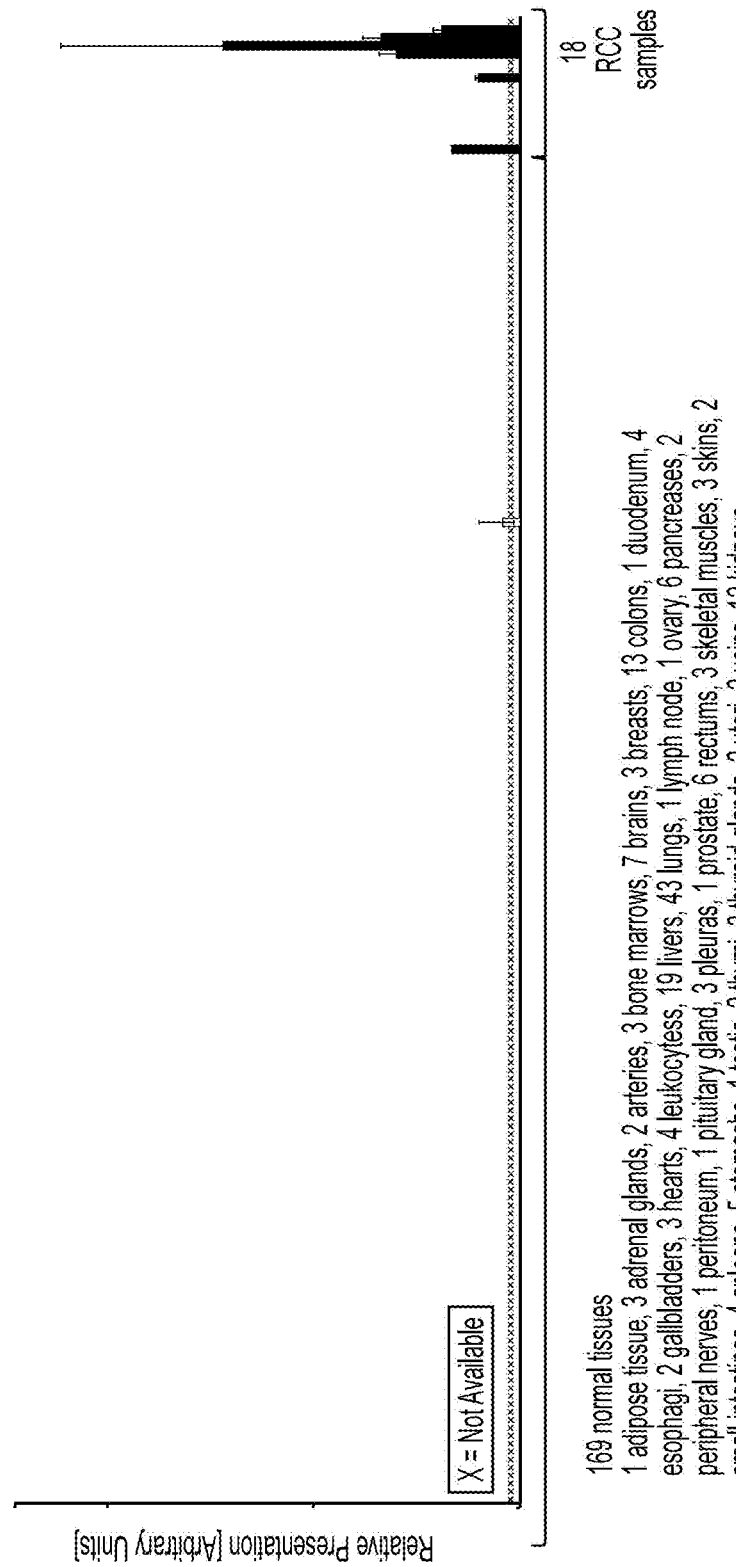
FIG. 1F) Gene:ESM1, Peptide: LLVPAHLVAA (SEQ ID No.: 25)—Tissues from left to right: 1 adipose tissue, 3 adrenal glands, 2 arteries, 3 bone marrows, 7 brains, 3 breasts, 13 colons, 1 duodenum, 4 esophagi, 2 gallbladders, 3 hearts, 4 leukocytes, 19 livers, 43 lungs, 1 lymph node, 1 ovary, 6 pancreases, 2 peripheral nerves, 1 peritoneum, 1 pituitary gland, 3 pleuras, 1 prostate, 6 rectums, 3 skeletal muscles, 3 skins, 2 small intestines, 4 spleens, 5 stomachs, 1 testis, 2 thymi, 3 thyroid glands, 2 uteri, 2 veins, 12 kidneys, 18 RCC. The peptide was also found on pancreatic cancer, esophageal cancer, brain cancer, lung cancer and uterine cancer (not shown).
Figure 1G:
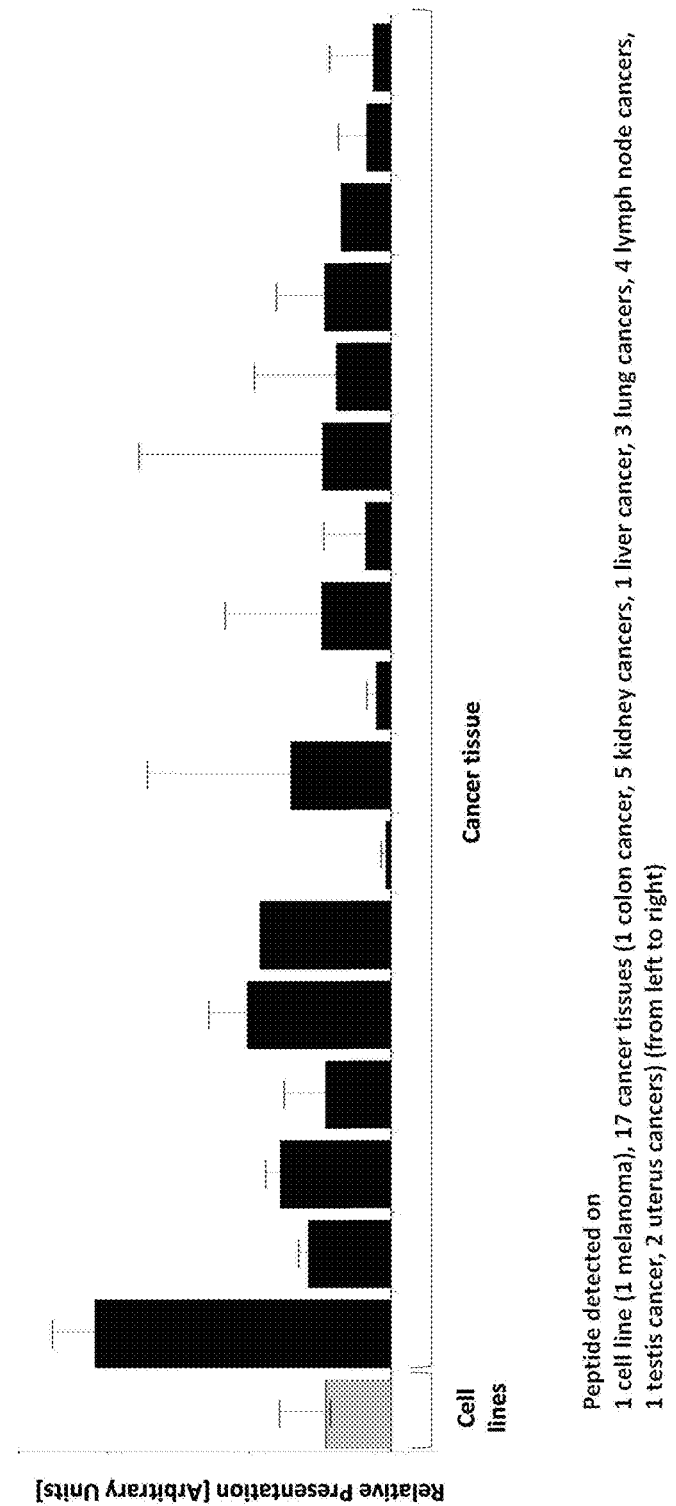
FIG. 1G) Gene: ARHGAP42, Peptide: ILIKHLVKV (SEQ ID NO.: 15)—Tissues from left to right: 1 cell line (1 melanoma), 17 cancer tissues (1 colon cancer, 5 kidney cancers, 1 liver cancer, 3 lung cancers, 4 lymph node cancers, 1 testis cancer, 2 uterus cancers).
Figure 1I:
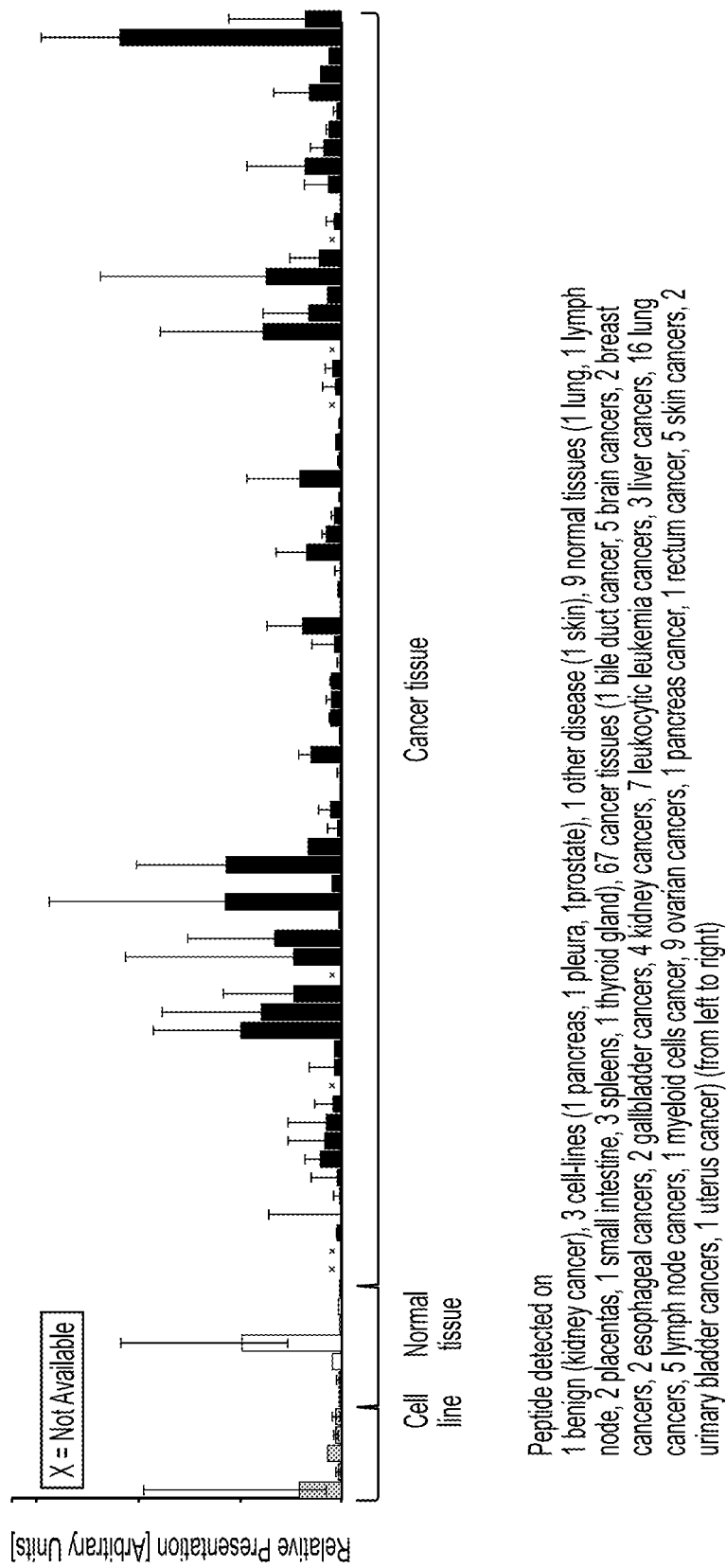
FIG. 1I) Gene: HSF2B, Peptide: VLLDTILQL (SEQ ID NO.: 38)—Tissues from left to right: 1 benign (kidney cancer), 3 cell-lines (1 pancreas, 1 pleura, 1prostate), 1 other disease (1 skin), 9 normal tissues (1 lung, 1 lymph node, 2 placentas, 1 small intestine, 3 spleens, 1 thyroid gland), 67 cancer tissues (1 bile duct cancer, 5 brain cancers, 2 breast cancers, 2 esophageal cancers, 2 gallbladder cancers, 4 kidney cancers, 7 leukocytic leukemia cancers, 3 liver cancers, 16 lung cancers, 5 lymph node cancers, 1 myeloid cells cancer, 9 ovarian cancers, 1 pancreas cancer, 1 rectum cancer, 5 skin cancers, 2 urinary bladder cancers, 1 uterus cancer).
Figure 1J:
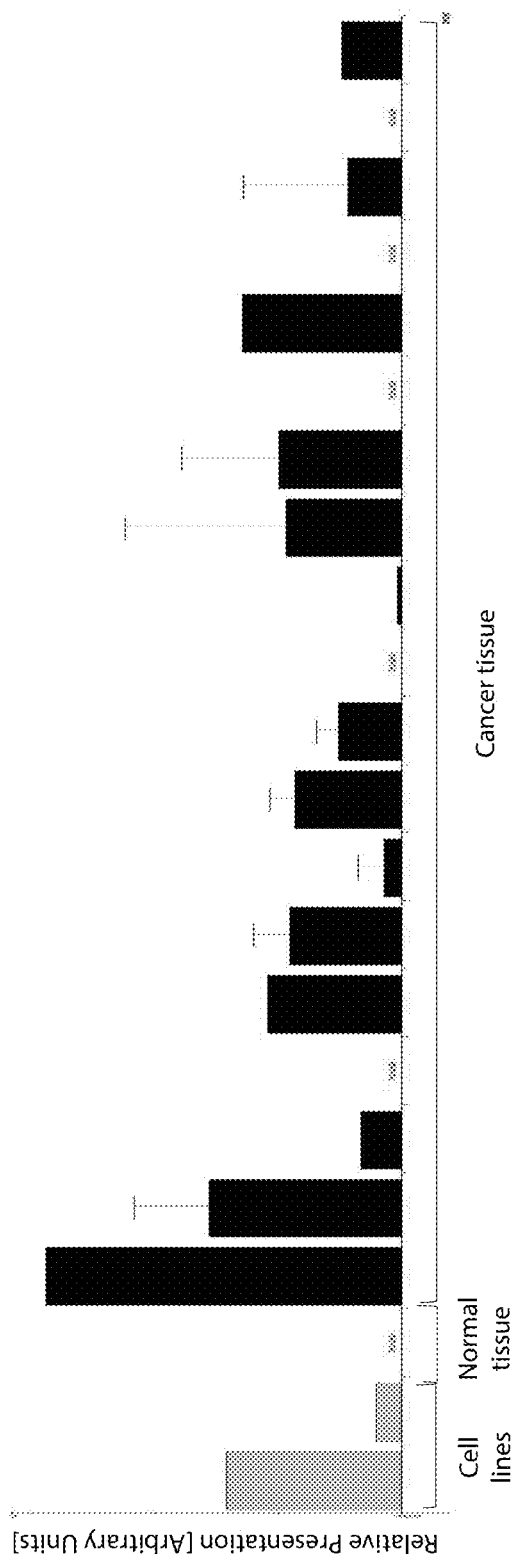
FIG. 1J) Gene: TRAM1, Peptide: YLLNLNHLGL (SEQ ID NO.: 39)—Tissues from left to right: 2 cell lines (1 kidney, 1 pancreas), 1 normal tissues (1 lung), 19 cancer tissues (1 breast cancer, 2 kidney cancers, 3 leukocytic leukemia cancers, 2 liver cancers, 7 lung cancers, 1 lymph node cancer, 1 ovarian cancer, 1 rectum cancer, 1 urinary bladder cancer).
Figure 1K:
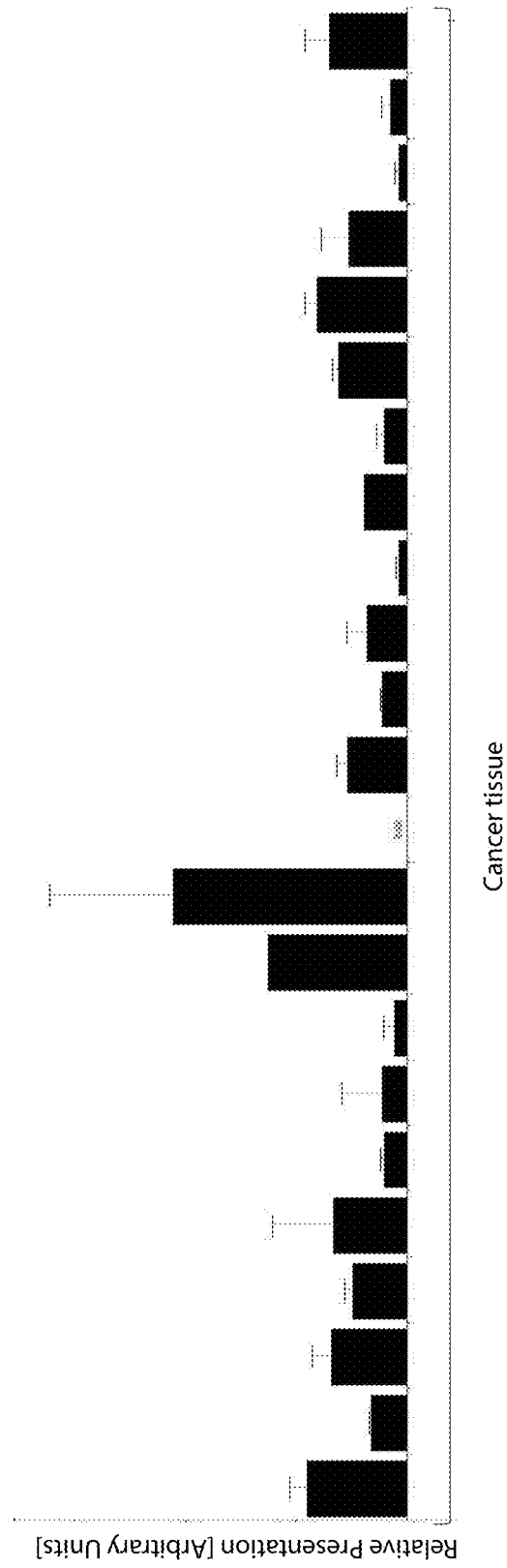
FIG. 1K) Gene: PXDNL, Peptide: SILDAVQRV (SEQ ID NO.: 52)—Tissues from left to right: 23 cancer tissues (3 brain cancers, 4 breast cancers, 3 kidney cancers, 8 lung cancers, 2 ovarian cancers, 1 pancreas cancer, 1 skin cancer, 1 uterus cancer).
Figure 1L:
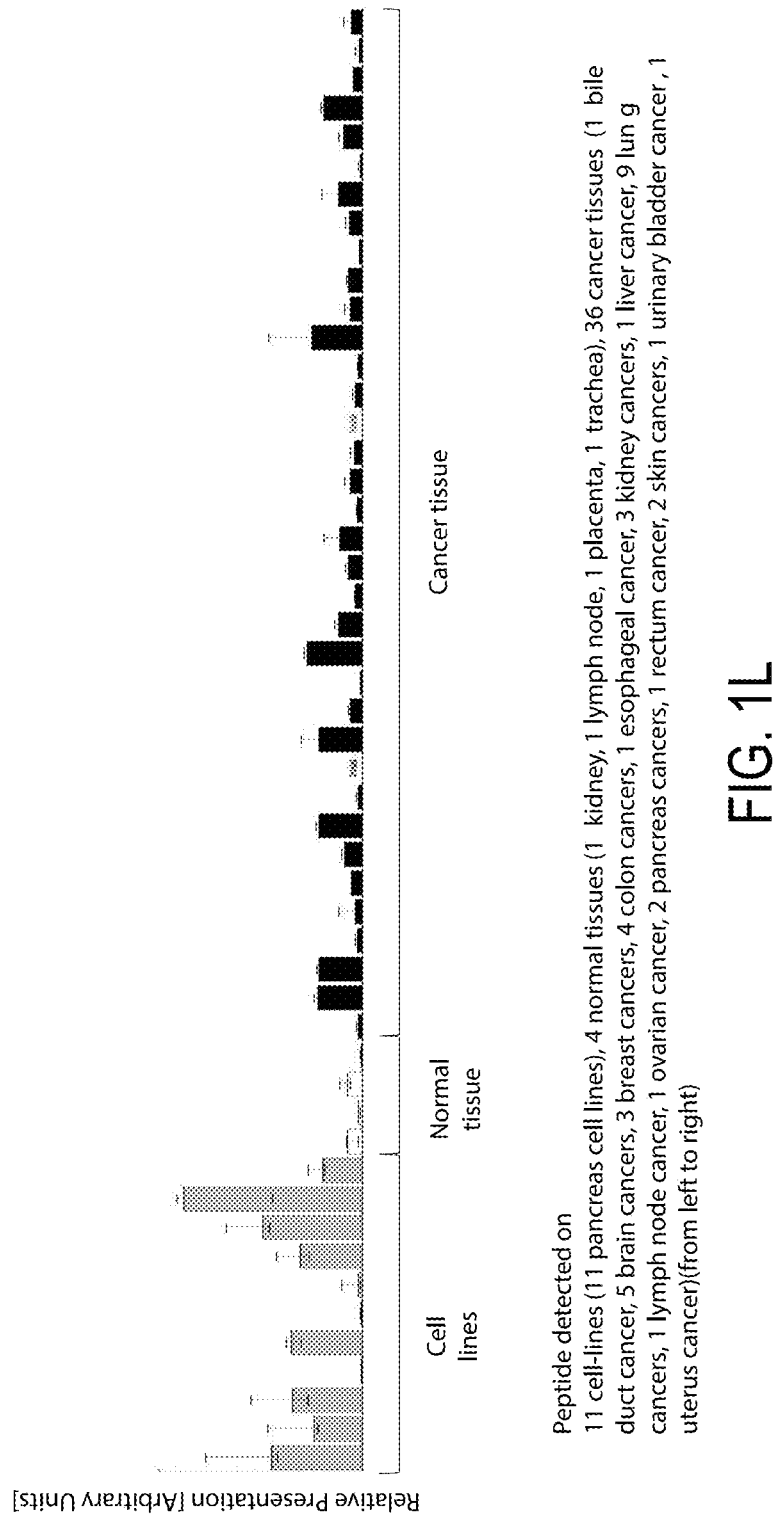
FIG. 1L) Gene: THY1, Peptide: SLLQATDFMSL (SEQ ID NO.: 82)—Tissues from left to right: 11 cell-lines (11 pancreas cell lines), 4 normal tissues (1 kidney, 1 lymph node, 1 placenta, 1 trachea), 36 cancer tissues (1 bile duct cancer, 5 brain cancers, 3 breast cancers, 4 colon cancers, 1 esophageal cancer, 3 kidney cancers, 1 liver cancer, 9 lung cancers, 1 lymph node cancer, 1 ovarian cancer, 2 pancreas cancers, 1 rectum cancer, 2 skin cancers, 1 urinary bladder cancer, 1 uterus cancer).
Figure 1M:
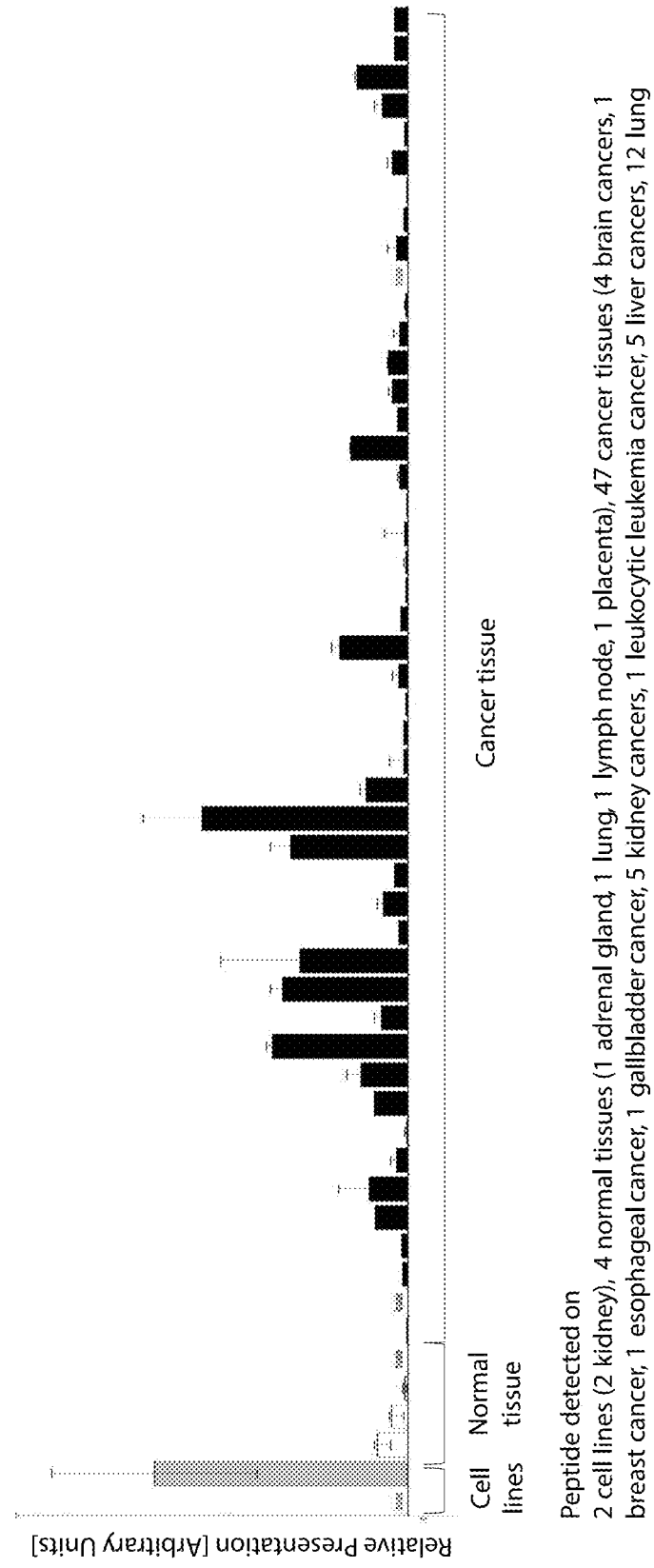
FIG. 1M) Gene: ARRDC3, Peptide: KIPPVSPSI (SEQ ID NO.: 98)—Tissues from left to right: 2 cell lines (2 kidney), 4 normal tissues (1 adrenal gland, 1 lung, 1 lymph node, 1 placenta), 47 cancer tissues (4 brain cancers, 1 breast cancer, 1 esophageal cancer, 1 gallbladder cancer, 5 kidney cancers, 1 leukocytic leukemia cancer, 5 liver cancers, 12 lung cancers, 2 lymph node cancers, 4 ovarian cancers, 3 prostate cancers, 2 skin cancers, 6 uterus cancers).

Identification and Quantitation of Tumor Associated Peptides Presented on the Cell Surface Tissue Samples Patients' tumor tissues were obtained from BioServe (Beltsville, Md., USA); University Hospital of Munich; Kyoto Prefectural University of Medicine (KPUM); University Hospital of Tübingen.

Normal (healthy) tissues were obtained from Bio-Options Inc., CA, USA; BioServe, Beltsville, Md., USA; Capital BioScience Inc., Rockville, Md., USA; Geneticist Inc., Glendale, Calif., USA; University Hospital of Geneva; University Hospital of Heidelberg; Kyoto Prefectural University of Medicine (KPUM); University Hospital Munich; ProteoGenex Inc., Culver City, Calif., USA; University Hospital of Tübingen.

Written informed consents of all patients had been given before surgery or autopsy. Tissues were shock-frozen immediately after excision and stored until isolation of TUMAPs at −70° C. or below.

Isolation of HLA Peptides from Tissue Samples

HLA peptide pools from shock-frozen tissue samples were obtained by immune precipitation from solid tissues according to a slightly modified protocol (Falk et al., 1991; Seeger et al., 1999) using the HLA-A*02-specific antibody BB7.2, the HLA-A, -B, C-specific antibody W6/32, CNBr-activated sepharose, acid treatment, and ultrafiltration.

Mass Spectrometry Analyses

The HLA peptide pools as obtained were separated according to their hydrophobicity by reversed-phase chromatography (nanoAcquity UPLC system, Waters) and the eluting peptides were analyzed in LTQ-velos and fusion hybrid mass spectrometers (ThermoElectron) equipped with an ESI source. Peptide pools were loaded directly onto the analytical fused-silica micro-capillary column (75 μm i.d.× 250 mm) packed with 1.7 μm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometers were operated in the data-dependent mode using a TOP5 strategy. In brief, a scan cycle was initiated with a full scan of high mass accuracy in the Orbitrap (R=30 000), which was followed by MS/MS scans also in the Orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide.

Label-free relative LC-MS quantitation was performed by ion counting i.e. by extraction and analysis of LC-MS features (Mueller et al., 2007). The method assumes that the peptide's LC-MS signal area correlates with its abundance in the sample. Extracted features were further processed by charge state deconvolution and retention time alignment (Mueller et al., 2008; Sturm et al., 2008). Finally, all LC-MS features were cross-referenced with the sequence identification results to combine quantitative data of different samples and tissues to peptide presentation profiles. The quantitative data were normalized in a two-tier fashion according to central tendency to account for variation within technical and biological replicates. Thus each identified peptide can be associated with quantitative data allowing relative quantification between samples and tissues. In addition, all quantitative data acquired for peptide candidates was inspected manually to assure data consistency and to verify the accuracy of the automated analysis. For each peptide a presentation profile was calculated showing the mean sample presentation as well as replicate variations.

Figure 1N:
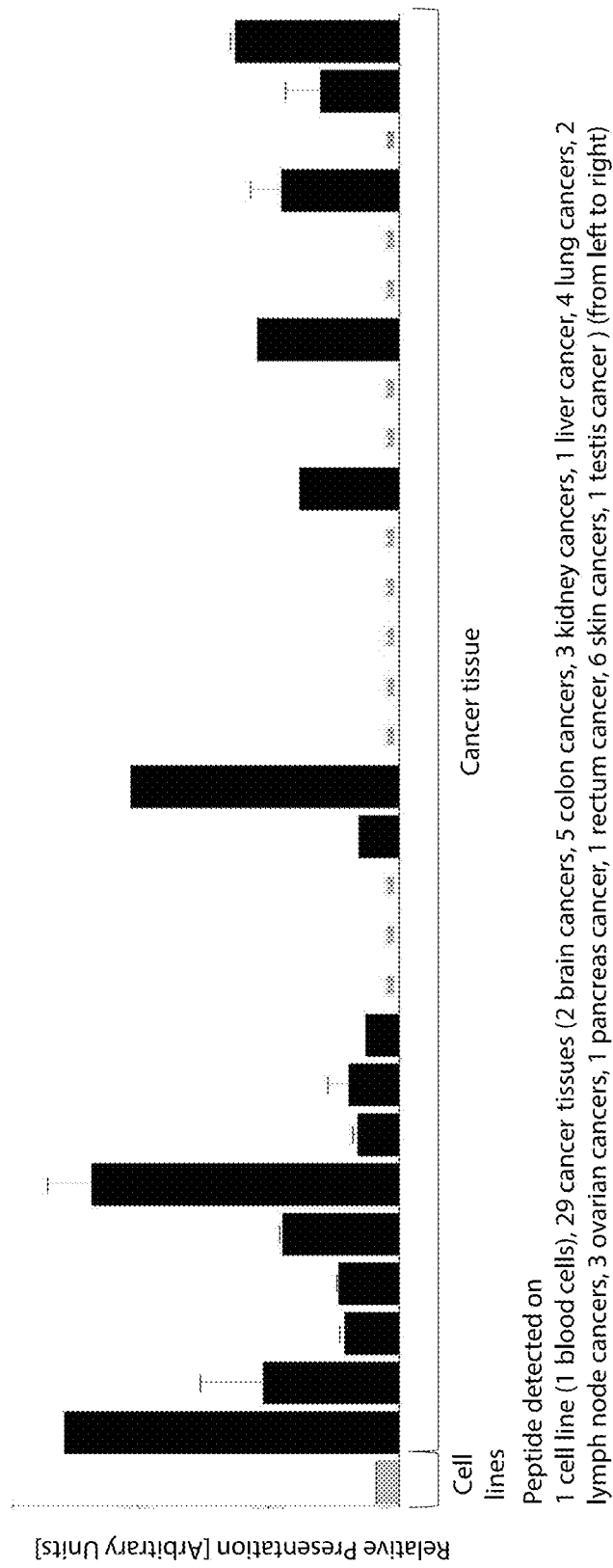
Figure 2A:
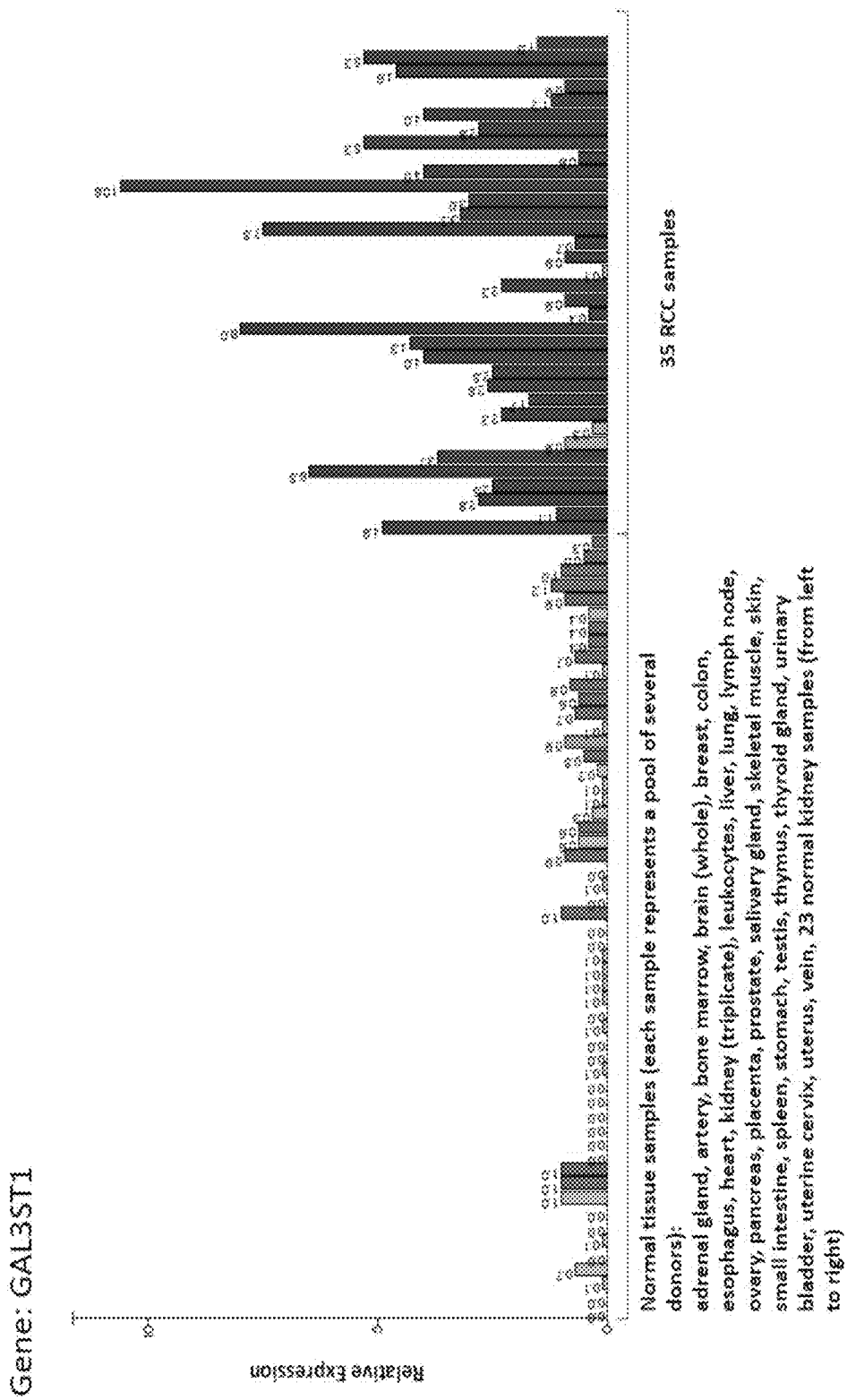
FIGS. 2A to 2D show exemplary expression profiles (relative expression compared to normal kidney) of source genes of the present invention that are highly over-expressed or exclusively expressed in RCC in a panel of normal tissues and 35 RCC samples. Tissues from left to right: adrenal gland, artery, bone marrow, brain (whole), breast, colon, esophagus, heart, kidney (triplicate), leukocytes, liver, lung, lymph node, ovary, pancreas, placenta, prostate, salivary gland, skeletal muscle, skin, small intestine, spleen, stomach, testis, thymus, thyroid gland, urinary bladder, uterine cervix, uterus, vein, 23 normal kidney samples, 35 RCC samples.
Figure 2B:
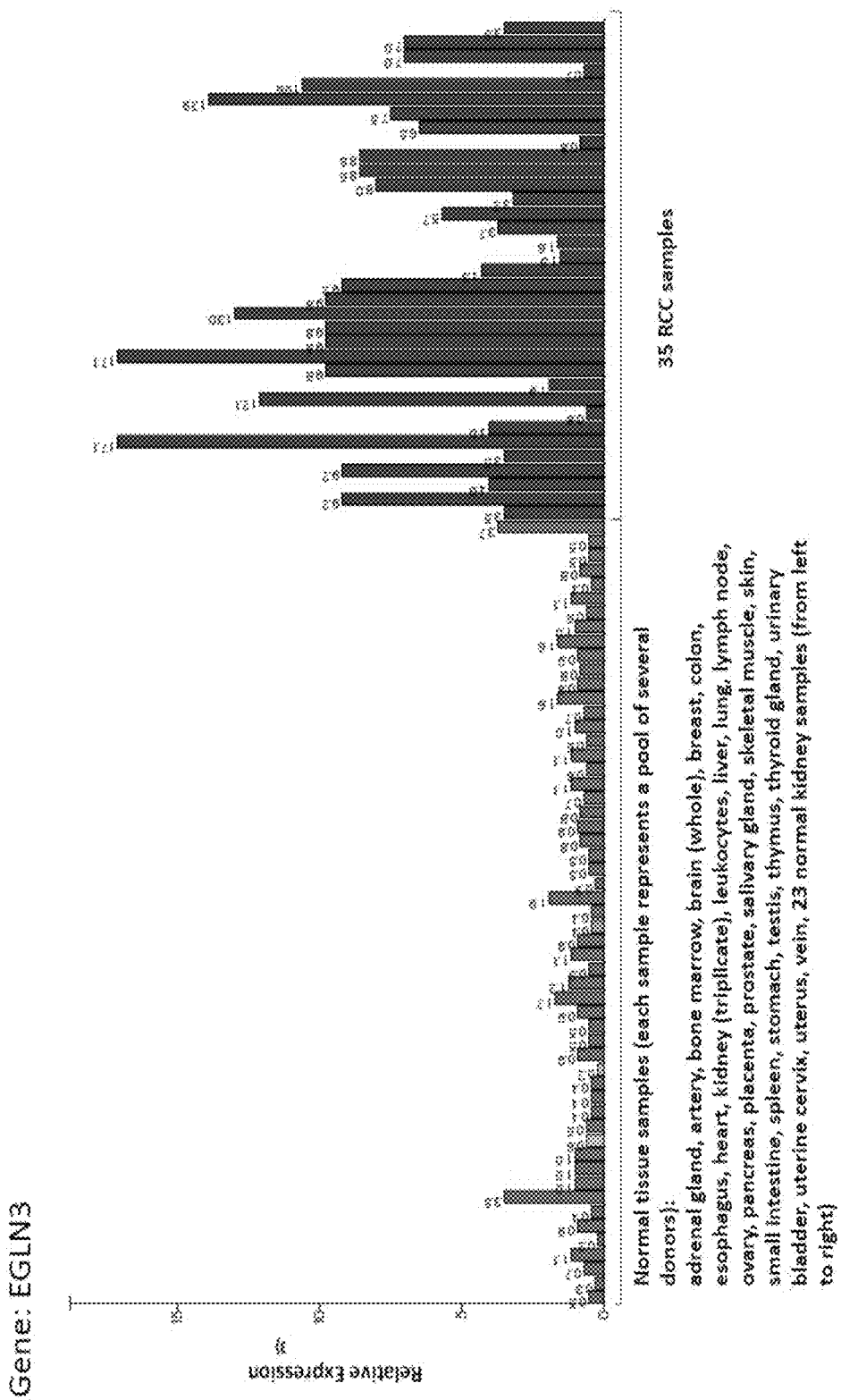
Figure 2C:
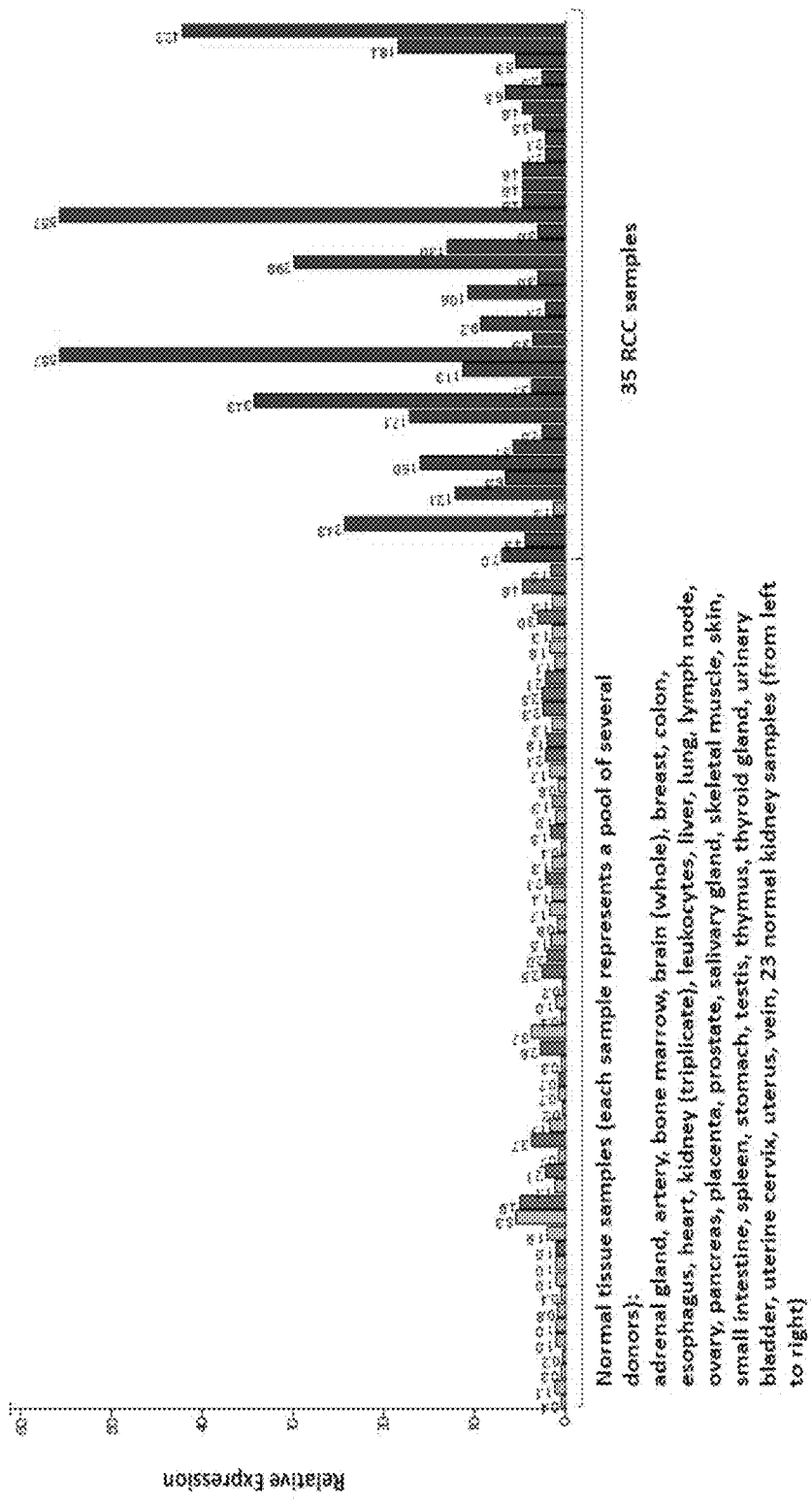
Figure 2D:
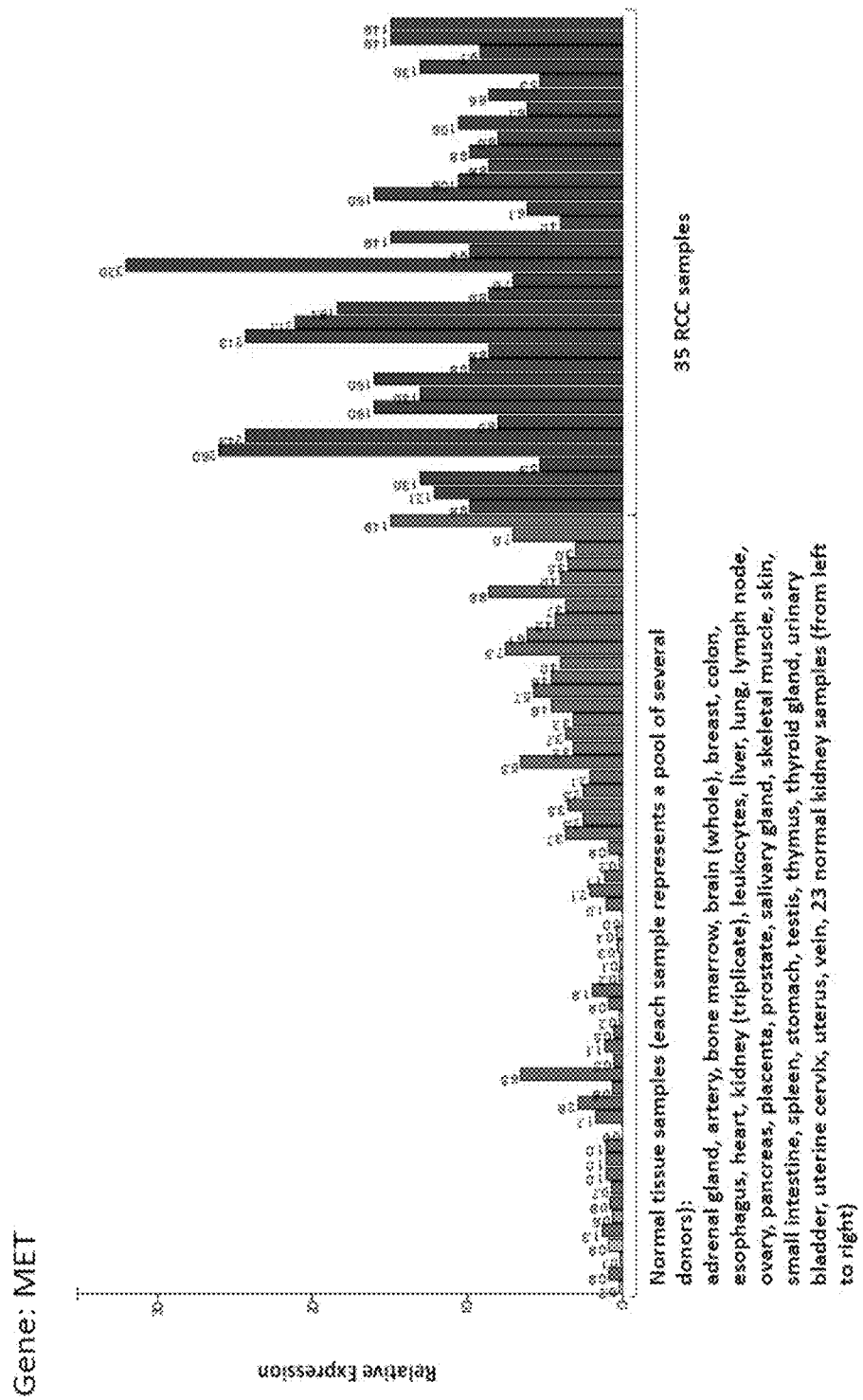
Figure 3A:
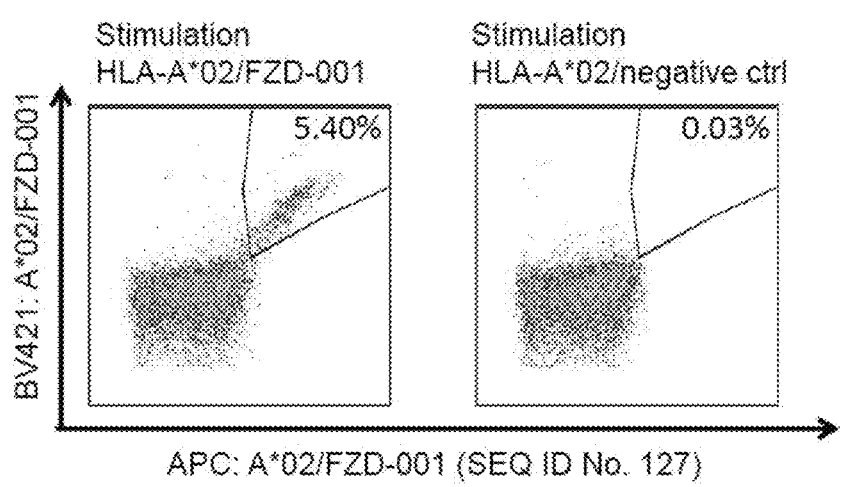
FIGS. 3A-3F show exemplary immunogenicity data: flow cytometry results after peptide-specific multimer staining, as results of peptide-specific in vitro CD8+ T cell responses of a healthy HLA-A*02+donor. CD8+ T cells were primed using artificial APCs coated with anti-CD28 mAb and HLA-A*02 in complex with SeqID No 127 peptide (FIG. 3A, left panel), SeqID No 145 peptide (FIG. 3B, left panel), SeqID No 20 peptide (FIG. 3C, left panel), SeqID No 34 peptide (FIG. 3D, left panel), SeqID No 1 peptide (FIG. 3E, left panel) or SeqID No 15 peptide (FIG. 3F, left panel) respectively. After three cycles of stimulation, the detection of peptide-reactive cells was performed by 2D multimer staining with A*02/FZD-001 (SeqID No 127) (FIG. 3A), A*02/ATP-001 (SeqID No 145) (FIG. 3B), A*02/SeqID No 20 (FIG. 3C), A*02/SeqID No 34 (FIG. 3D), A*02/SeqID No 1 (FIG. 3E) or A*02/SeqID No 15 (FIG. 3F). Right panels (FIGS. 3C, 3D, 3E and 3F) show control staining of cells stimulated with irrelevant A*02/peptide complexes. Viable singlet cells were gated for CD8+lymphocytes. Boolean gates helped excluding false-positive events detected with multimers specific for different peptides. Frequencies of specific multimer+cells among CD8+lymphocytes are indicated.
Figure 3B:
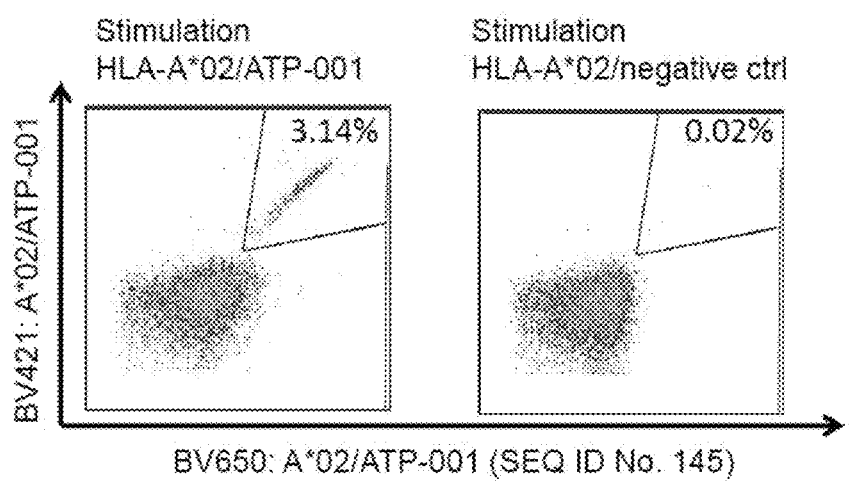
Figure 3C:
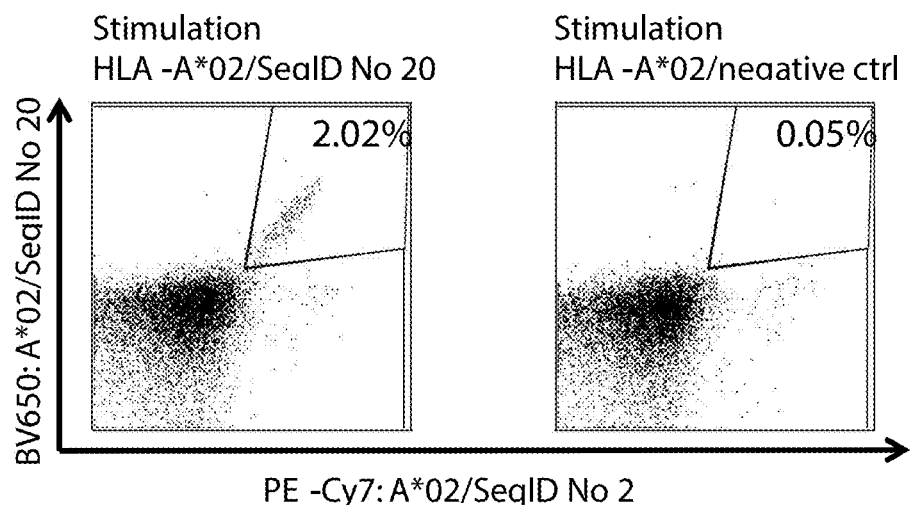
Figure 3D:
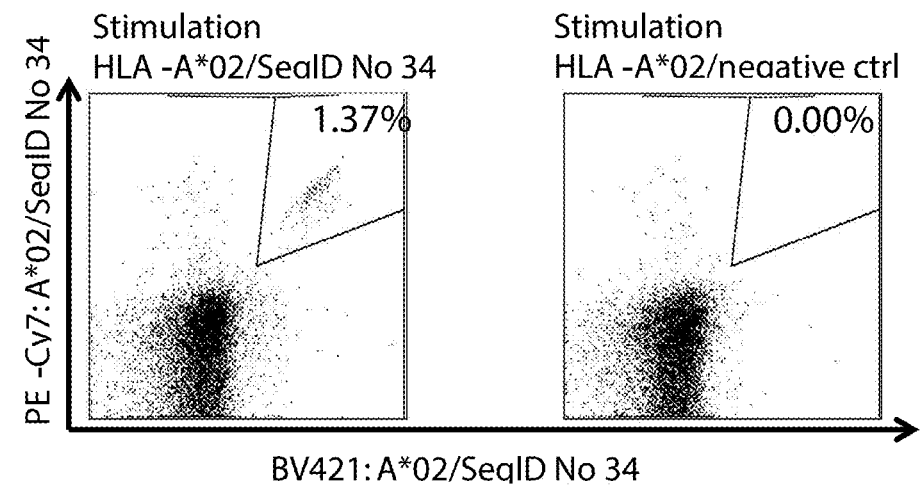
Figure 3E:
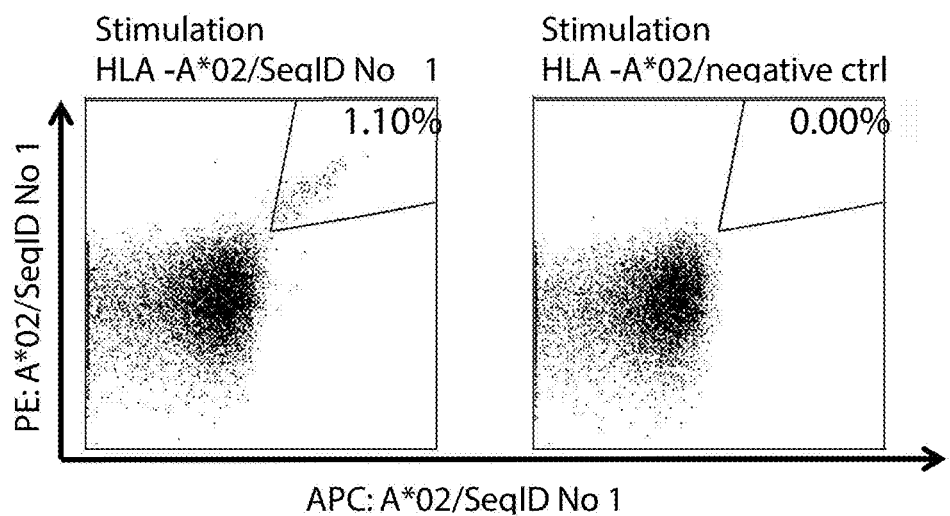
Figure 3F:
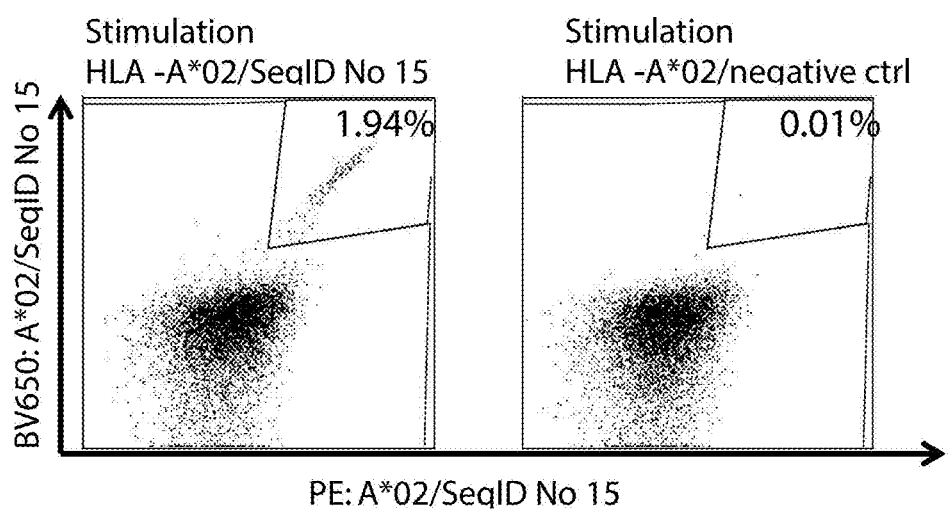

The profiles juxtapose RCC samples to a baseline of normal tissue samples. Presentation profiles of exemplary over-presented peptides are shown in FIGS. 1A-1N. Presentation scores for exemplary peptides are shown in Table 8.

TABLE 8

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+).

| SEQ ID No. | Sequence | Peptide Presentation |
|---|---|---|
| 1 | ALIVSLPYL | +++ |
| 2 | ILWREVVTL | +++ |
| 3 | RLLGEVQAL | +++ |
| 4 | FLSQDIITV | +++ |
| 5 | YLYPNLTRL | +++ |
| 6 | VLFELSKTV | +++ |
| 7 | FLLSLIDRL | +++ |
| 8 | GLASFKSFL | +++ |
| 9 | ILLQKPDSV | +++ |
| 10 | KLLQNNYGL | + |
| 11 | FIQTEAPKEV | +++ |
| 12 | ALDPSGNQLI | +++ |
| 13 | KIMAQILTV | + |
| 14 | ALLTETIFL | ++ |
| 15 | ILIKHLVKV | +++ |
| 16 | FMPEELPQL | +++ |
| 17 | ILAQQVHAL | +++ |
| 18 | YVLDLAAKV | +++ |
| 19 | LLDPGSLQL | + |
| 20 | AVANTTFTV | +++ |
| 21 | RLIQGDQILSV | +++ |
| 23 | YIQEVVQYI | +++ |
| 24 | FTLGTTVFL | ++ |
| 26 | SLMEILYTL | +++ |
| 27 | SLSDLLVSL | ++ |
| 28 | FIADLVVGL | ++ |
| 29 | ILLDLEQAL | + |
| 30 | QLFYTKIFL | ++ |
| 31 | VLFGLDPAVIKV | + |
| 32 | FLAGGIRGSGA | +++ |
| 33 | FIADVVEKI | +++ |
| 34 | ELNNQNFYL | +++ |

TABLE 8-continued

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+).

| SEQ ID No. | Sequence | Peptide Presentation |
|---|---|---|
| 35 | VLHSLQTQL | +++ |
| 36 | SLFGKKYIL | +++ |
| 37 | VLAPVILML | +++ |
| 38 | VLLDTILQL | +++ |
| 39 | YLLNLNHLGL | +++ |
| 40 | YIQEHLLQI | ++ |
| 41 | GLLKTLQKL | + |
| 42 | VILDTGTIQL | +++ |
| 43 | YLKDELDEL | +++ |
| 44 | ALFSFVTAL | + |
| 45 | ALLGIPLTL | ++ |
| 47 | TLAEVRAVQEI | + |
| 48 | VVASNIMEV | +++ |
| 49 | VLIVEVPGV | +++ |
| 50 | SLSDHIVLL | + |
| 51 | NLWPMILTL | +++ |
| 52 | SILDAVQRV | +++ |
| 55 | YLALILPVL | +++ |
| 56 | ILMDFSNSM | + |
| 57 | SLQKEILYL | +++ |
| 58 | FLVDFEQSHL | ++ |
| 60 | ILWKDIEYV | +++ |
| 61 | SLMGILLRI | +++ |
| 62 | VLAGPAFLVQL | +++ |
| 66 | TLLKTIIKV | ++ |
| 67 | LLDVLAPLV | + |
| 68 | YVLTQPPSV | +++ |
| 69 | ILADLLPSL | ++ |
| 70 | SLTALRLLL | + |
| 72 | YSLEKVFGI | + |
| 73 | GLDGIPFTV | ++ |
| 74 | GLFHKQVTV | + |
| 75 | FLIKSINLV | ++ |
| 77 | SLIKHKIML | ++ |
| 78 | ALLDTVVQA | + |
| 79 | ALADIVWRA | + |
| 80 | KLASMLETL | + |
| 83 | IQWSIVPEV | ++ |
| 86 | GLLQGKLALL | + |
| 88 | TLAELHISL | + |
| 89 | SLLLAVTEV | + |
| 90 | FTLEKNFVI | ++ |
| 91 | MLLSSLVSL | + |
| 92 | FLFRDILEL | +++ |
| 93 | GVMAGDIYSV | ++ |
| 94 | ILHHKVYDL | + |
| 96 | TLAETLVNL | + |
| 97 | TLISELVQA | + |
| 98 | KIPPVSPSI | +++ |
| 99 | GLAPHLEQI | + |
| 100 | KLNVAPLAV | + |
| 101 | HIYDKAFITV | ++ |
| 102 | LLFDVHTTL | + |
| 103 | KLQDGLLHI | +++ |
| 104 | ALFEGVVRQI | +++ |
| 105 | ALADLDELLIRA | ++ |
| 106 | VLMDLKALL | + |
| 107 | VLMDLKALLL | ++ |
| 108 | VLISVLQAI | ++ |
| 109 | YLWSRVEKL | + |
| 110 | LLDLHSYLL | + |
| 111 | TLLETEMLL | +++ |
| 112 | LLFDHLEPIEL | + |
| 113 | SLFDWNVKL | ++ |
| 114 | ALAVNISAA | ++ |
| 115 | LLDPKTIFL | +++ |
| 116 | GLVDIMVHL | +++ |
| 117 | VLFGELPAL | +++ |
| 118 | FLNAIETAL | +++ |
| 119 | RLHDENILL | +++ |

TABLE 8-continued

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+).

| SEQ ID No. | Sequence | Peptide Presentation |
|---|---|---|
| 120 | GLAGDNIYL | +++ |
| 121 | ALLRTVVSV | ++ |
| 122 | SLDPSSPQV | ++ |
| 123 | YVDPVITSI | ++ |
| 124 | ILSPLSVAL | + |
| 125 | KLDPTKTTL | +++ |
| 126 | KIQEILTQV | +++ |
| 127 | VLAPLFVYL | ++ |
| 128 | YLEEDVYQL | +++ |
| 129 | VLAPRVLRA | ++ |
| 130 | ALPTVLVGV | ++ |
| 131 | VMAGDIYSV | ++ |
| 132 | SVASTITGV | ++ |
| 133 | QLIDYERQL | ++ |
| 134 | VADKIHSV | +++ |
| 135 | VVDEGPTGV | +++ |
| 136 | YQDPHSTAV | ++ |
| 137 | TLVAIVVGV | ++ |
| 138 | SLDTLMTYV | ++ |
| 139 | ILNVDGLIGV | ++ |
| 140 | SLANNVTSV | ++ |
| 141 | LLVDDSFLHTV | +++ |
| 143 | ALFVRLLALA | ++ |
| 145 | SLHFLILYV | + |
| 150 | TLMPNINKL | +++ |
| 151 | YMYEGPAPRI | +++ |

Example 2

Expression Profiling of Genes Encoding the Peptides of the Invention

Over-presentation or specific presentation of a peptide on tumor cells compared to normal cells is sufficient for its usefulness in immunotherapy, and some peptides are tumor-specific despite their source protein occurring also in normal tissues. Still, mRNA expression profiling adds an additional level of safety in selection of peptide targets for immunotherapies. Especially for therapeutic options with high safety risks, such as affinity-matured TCRs, the ideal target peptide will be derived from a protein that is unique to the tumor and not found on normal tissues.

RNA Sources and Preparation

Surgically removed tissue specimens were provided as indicated above (see Example 1) after written informed consent had been obtained from each patient. Tumor tissue specimens were snap-frozen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues was obtained commercially (Ambion, Huntingdon, UK; Clontech, Heidelberg, Germany; Stratagene, Amsterdam, Netherlands; BioChain, Hayward, Calif., USA). The RNA from several individuals (between 2 and 123 individuals) was mixed such that RNA from each individual was equally weighted.

Quality and quantity of all RNA samples were assessed on an Agilent 2100 Bioanalyzer (Agilent, Waldbronn, Germany) using the RNA 6000 Pico LabChip Kit (Agilent).

Microarray Experiments

Gene expression analysis of all tumor and normal tissue RNA samples was performed by Affymetrix Human Genome (HG) U133A or HG-U133 Plus 2.0 oligonucleotide microarrays (Affymetrix, Santa Clara, Calif., USA). All steps were carried out according to the Affymetrix manual. Briefly, double-stranded cDNA was synthesized from 5-8 g of total RNA, using SuperScript RTII (Invitrogen) and the oligo-dT-T7 primer (MWG Biotech, Ebersberg, Germany) as described in the manual. In vitro transcription was performed with the BioArray High Yield RNA Transcript Labelling Kit (ENZO Diagnostics, Inc., Farmingdale, N.Y., USA) for the U133A arrays or with the GeneChip IVT Labelling Kit (Affymetrix) for the U133 Plus 2.0 arrays, followed by cRNA fragmentation, hybridization, and staining with streptavidin-phycoerythrin and biotinylated anti-streptavidin antibody (Molecular Probes, Leiden, Netherlands). Images were scanned with the Agilent 2500A GeneArray Scanner (U133A) or the Affymetrix Gene-Chip Scanner 3000 (U133 Plus 2.0), and data were analyzed with the GCOS software (Affymetrix), using default settings for all parameters. For normalization, 100 housekeeping genes provided by Affymetrix were used. Relative expression values were calculated from the signal log ratios given by the software and the normal kidney sample was arbitrarily set to 1.0. Exemplary expression profiles of source genes of the present invention that are highly over-expressed or exclusively expressed in RCC are shown in FIGS. 2A-2D. Expression scores for further exemplary genes are shown in Table 9.

TABLE 9

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+).

| Seq ID NO | Gene Name | sequence | Gene Expression |
|---|---|---|---|
| 1 | SLC17A3 | ALIVSLPYL | ++ |
| 2 | HSF4 | ILWREVVTL | ++ |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+).

| Seq ID NO | Gene Name | sequence | Gene Expression |
|---|---|---|---|
| 3 | HSF4 | RLLGEVQAL | ++ |
| 6 | ATP11A | VLFELSKTV | + |
| 7 | EGLN3 | FLLSLIDRL | ++ |
| 18 | ACLY | YVLDLAAKV | + |
| 28 | ENO1, ENO2, ENO3 | FIADLVVGL | + |
| 35 | ANGPTL4 | VLHSLQTQL | ++ |
| 37 | ABCC3 | VLAPVILML | + |
| 40 | IVNS1ABP | YIQEHLLQI | + |
| 50 | ITGA3 | SLSDHIVLL | + |
| 51 | ITGA3 | NLWPMILTL | + |
| 55 | SLC16A4 | YLALILPVL | + |
| 59 | TGFBI | SLKNNVVSV | + |
| 62 | SLC47A1 | VLAGPAFLVQL | + |
| 63 | ERAP1 | GLIEDHFDVTV | + |
| 65 | TPI1, TPI1P1 | IIYGGSVTGA | + |
| 76 | PDZK1P2, PDZK1, PDZK1P1 | VLADDHLIEV | ++ |
| 81 | LRP2 | SLLPALPKL | + |
| 87 | APOL1 | LADGVQKV | ++ |
| 93 | PLIN2 | GVMAGDIYSV | + |
| 94 | CYB5A | ILHHKVYDL | + |
| 101 | FLT1 | HIYDKAFITV | ++ |
| 105 | HSPG2 | ALADLDELLIRA | + |
| 115 | HAVCR1 | LLDPKTIFL | + |
| 120 | SLC22A2 | GLAGDNIYL | + |
| 122 | GAL3ST1 | SLDPSSPQV | +++ |
| 123 | MET | YVDPVITSI | ++ |
| 125 | NDRG1 | KLDPTKTTL | + |
| 127 | FZD2, FZD1, FZD7 | VLAPLFVYL | + |
| 131 | PLIN2 | VMAGDIYSV | + |
| 132 | PLIN2 | SVASTITGV | + |
| 137 | FKBP10 | TLVAIVVGV | + |
| 139 | ACLY | ILNVDGLIGV | + |
| 143 | TGFBI | ALFVRLLALA | + |

Example 3

In Vitro Immunogenicity for MHC Class I Presented Peptides

In order to obtain information regarding the immunogenicity of the TUMAPs of the present invention, the inventors performed investigations using an in vitro T-cell priming assay based on repeated stimulations of CD8+ T cells with artificial antigen presenting cells (aAPCs) loaded with peptide/MHC complexes and anti-CD28 antibody. This way the inventors could show immunogenicity for 22 HLA-A*0201 restricted TUMAPs of the invention so far, demonstrating that these peptides are T-cell epitopes against which CD8+ precursor T cells exist in humans (Table 10).

In Vitro Priming of CD8+ T Cells

In order to perform in vitro stimulations by artificial antigen presenting cells loaded with peptide-MHC complex (pMHC) and anti-CD28 antibody, the inventors first isolated CD8+ T cells from fresh HLA-A*02 leukapheresis products via positive selection using CD8 microbeads (Miltenyi Biotec, Bergisch-Gladbach, Germany) of healthy donors obtained from the University clinics Mannheim, Germany, after informed consent.

PBMCs and isolated CD8+lymphocytes were incubated in T-cell medium (TCM) until use consisting of RPMI-Glutamax (Invitrogen, Karlsruhe, Germany) supplemented with 10% heat inactivated human AB serum (PAN-Biotech, Aidenbach, Germany), 100 U/ml Penicillin/100 pg/ml Streptomycin (Cambrex, Cologne, Germany), 1 mM sodium pyruvate (CC Pro, Oberdorla, Germany), 20 pg/ml Gentamycin (Cambrex). 2.5 ng/ml IL-7 (PromoCell, Heidelberg, Germany) and 10 U/ml IL-2 (Novartis Pharma, Nirnberg, Germany) were also added to the TCM at this step.

Generation of pMHC/anti-CD28 coated beads, T-cell stimulations and readout was performed in a highly defined in vitro system using four different pMHC molecules per stimulation condition and 8 different pMHC molecules per readout condition.

The purified co-stimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.6 μm diameter streptavidin coated polystyrene particles (Bangs Laboratories, Illinois, USA).

pMHC used for positive and negative control stimulations were A*0201/MLA-001 (peptide ELAGIGILTV (SEQ ID NO. 152) from modified Melan-A/MART-1) and A*0201/DDX5-001 (YLLPAIVHI from DDX5 (SEQ ID NO. 153)), respectively.

800.000 beads/200 pl were coated in 96-well plates in the presence of 4×12.5 ng different biotin-pMHC, washed and 600 ng biotin anti-CD28 were added subsequently in a volume of 200 pl. Stimulations were initiated in 96-well plates by co-incubating 1×10$^6$ CD8+ T cells with 2×10$^5$ washed coated beads in 200 pl TCM supplemented with 5 ng/ml IL-12 (PromoCell) for 3 days at 37° C. Half of the medium was then exchanged by fresh TCM supplemented with 80 U/ml IL-2 and incubating was continued for 4 days at 37° C. This stimulation cycle was performed for a total of three times. For the pMHC multimer readout using 8 different pMHC molecules per condition, a two-dimensional combinatorial coding approach was used as previously described (Andersen et al., 2012) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+cells. Evaluation of multimeric analysis was done using the FlowJo software (Tree Star, Oregon, USA). In vitro priming of specific multimer+CD8+lymphocytes was detected by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+among CD8+ T-cells and the percentage of specific multimer+cells was at least 10× the median of the negative control stimulations).

In Vitro Immunogenicity for RCC Peptides

For tested HLA class I peptides, in vitro immunogenicity could be demonstrated by generation of peptide specific T-cell lines. Exemplary flow cytometry results after TUMAP-specific multimer staining for 2 peptides of the invention are shown in FIGS. 3A-3F together with corresponding negative controls. Results for 3 peptides from the invention are summarized in Table 10A) and B).

TABLE 10A in vitro immunogenicity of HLA class I peptides of the invention
Exemplary results of in vitro immunogenicity experiments conducted by the applicant for the peptides of the invention. <20% = +; 20%-49% = ++; 50%-69% = +++; > = 70% = ++++

| Seq ID | Peptide ID | wells | donors |
|---|---|---|---|
| 123 | YVDPVITSI | + | ++++ |
| 127 | VLAPLFVYL | ++ | ++++ |
| 143 | ALFVRLLALA | + | +++ |

TABLE 10B

In vitro immunogenicity of HLA class I peptides of the invention
Exemplary results of in vitro immunogenicity experiments conducted by the applicant for peptides of the invention. Results of in vitro immunogenicity experiments are indicated. Percentage of positive wells and donors (among evaluable) are summarized as indicated
<20% = +; 20%-49% = ++; 50%-69% = +++; > = 70% = ++++

| SEQ ID No | Sequence | Wells positive [%] |
|---|---|---|
| 1 | ALIVSLPYL | + |
| 2 | ILWREVVTL | + |
| 3 | RLLGEVQAL | + |
| 6 | VLFELSKTV | + |
| 7 | FLLSLIDRL | + |
| 9 | ILLQKPDSV | + |
| 15 | ILIKHLVKV | + |
| 16 | FMPEELPQL | + |
| 18 | YVLDLAAKV | ++ |

TABLE 10B-continued

In vitro immunogenicity of HLA class I peptides of the invention
Exemplary results of in vitro immunogenicity experiments conducted by the applicant for peptides of the invention. Results of in vitro immunogenicity experiments are indicated. Percentage of positive wells and donors (among evaluable) are summarized as indicated
<20% = +; 20%-49% = ++; 50%-69% = +++; > = 70% = ++++

| SEQ ID No | Sequence | Wells positive [%] |
|---|---|---|
| 20 | AVANTTFTV | + |
| 22 | FLSPPLPSV | ++ |
| 29 | ILLDLEQAL | + |
| 34 | ELNNQNFYL | ++ |
| 36 | SLFGKKYIL | ++ |
| 94 | ILHHKVYDL | ++ |
| 95 | KLTDVGIATL | ++++ |
| 98 | KIPPVSPSI | ++++ |

Example 4

Synthesis of Peptides

All peptides were synthesized using standard and well-established solid phase peptide synthesis using the Fmoc-strategy. Identity and purity of each individual peptide have been determined by mass spectrometry and analytical RP-HPLC. The peptides were obtained as white to off-white lyophilizates (trifluoro acetate salt) in purities of >50%. All TUMAPs are preferably administered as trifluoro-acetate salts or acetate salts, other salt-forms are also possible.

Example 5

MHC Binding Assays

Candidate peptides for T cell based therapies according to the present invention were further tested for their MHC binding capacity (affinity). The individual peptide-MHC complexes were produced by UV-ligand exchange, where a UV-sensitive peptide is cleaved upon UV-irradiation, and exchanged with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (β2m) of stabilized MHC complexes. The assay was performed as generally described in Rodenko et al. (Rodenko et al., 2006).

96 well MAXISorp plates (NUNC) were coated over night with 2ug/ml streptavidin in PBS at room temperature, washed 4× and blocked for 1 h at 37° C. in 2% BSA containing blocking buffer. Refolded HLA-A*02:01/MLA-001 monomers served as standards, covering the range of 15-500 ng/ml. Peptide-MHC monomers of the UV-exchange reaction were diluted 100 fold in blocking buffer. Samples were incubated for 1 h at 37° C., washed four times, incubated with 2ug/ml HRP conjugated anti-β2m for 1h at 37° C., washed again and detected with TMB solution that is stopped with $NH_2SO_4$. Absorption was measured at 450 nm. Candidate peptides that show a high exchange yield (preferably higher than 50%, most preferred higher than 75%) are generally preferred for a generation and production of antibodies or fragments thereof, and/or T cell receptors or fragments thereof, as they show sufficient avidity to the MHC molecules and prevent dissociation of the MHC complexes.

TABLE 11

MHC class I binding scores.
Binding of HLA-class I restricted peptides to HLA-A*02:01 was ranged by peptide exchange yield:
≥10% = +; ≥20% = ++; ≥50 = +++; ≥75% = ++++

| Seq ID | Sequence | Peptide exchange |
|---|---|---|
| 1 | ALIVSLPYL | +++ |
| 2 | ILWREVVTL | +++ |
| 3 | RLLGEVQAL | ++ |
| 4 | FLSQDIITV | +++ |
| 5 | YLYPNLTRL | ++ |
| 6 | VLFELSKTV | +++ |
| 7 | FLLSLIDRL | +++ |
| 8 | GLASFKSFL | ++ |
| 9 | ILLQKPDSV | ++ |
| 10 | KLLQNNYGL | ++ |
| 11 | FIQTEAPKEV | ++ |
| 12 | ALDPSGNQLI | ++ |
| 13 | KIMAQILTV | +++ |
| 14 | ALLTETIFL | ++ |
| 15 | ILIKHLVKV | ++ |
| 16 | FMPEELPQL | ++ |
| 17 | ILAQQVHAL | +++ |
| 18 | YVLDLAAKV | +++ |
| 19 | LLDPGSLQL | ++ |
| 20 | AVANTTFTV | ++ |
| 21 | RLIQGDQILSV | ++ |
| 22 | FLSPPLPSV | +++ |
| 23 | YIQEVVQYI | +++ |
| 24 | FTLGTTVFL | +++ |
| 25 | LLVPAHLVAA | ++ |
| 27 | SLSDLLVSL | +++ |
| 28 | FIADLVVGL | ++ |
| 29 | ILLDLEQAL | +++ |
| 30 | QLFYTKIFL | ++ |
| 31 | VLFGLDPAVIKV | +++ |
| 33 | FIADVVEKI | ++ |
| 34 | ELNNQNFYL | +++ |

TABLE 11-continued

MHC class I binding scores.
Binding of HLA-class I restricted peptides to HLA-A*02:01 was ranged by peptide exchange yield:
≥10% = +; ≥20% = ++; ≥50 = +++; ≥75% = ++++

| Seq ID | Sequence | Peptide exchange |
|---|---|---|
| 35 | VLHSLQTQL | ++ |
| 36 | SLFGKKYIL | ++ |
| 37 | VLAPVILML | ++ |
| 38 | VLLDTILQL | +++ |
| 39 | YLLNLNHLGL | +++ |
| 40 | YIQEHLLQI | +++ |
| 41 | GLLKTLQKL | ++ |
| 42 | VILDTGTIQL | ++ |
| 43 | YLKDELDEL | +++ |
| 44 | ALFSFVTAL | +++ |
| 45 | ALLGIPLTL | +++ |
| 46 | GLSEVLVQI | +++ |
| 47 | TLAEVRAVQEI | +++ |
| 48 | VVASNIMEV | ++ |
| 49 | VLIVEVPGV | +++ |
| 50 | SLSDHIVLL | ++ |
| 51 | NLWPMILTL | +++ |
| 52 | SILDAVQRV | ++ |
| 53 | FLLEIRQTL | ++ |
| 54 | ALVAKGLVQA | ++ |
| 55 | YLALILPVL | ++ |
| 56 | ILMDFSNSM | +++ |
| 57 | SLQKEILYL | ++ |
| 58 | FLVDFEQSHL | ++++ |
| 59 | SLKNNVVSV | +++ |
| 60 | ILWKDIEYV | +++ |
| 61 | SLMGILLRI | ++ |
| 62 | VLAGPAFLVQL | +++ |
| 63 | GLIEDHFDVTV | ++ |
| 64 | LLAASVALA | ++ |
| 65 | IIYGGSVTGA | ++ |
| 66 | TLLKTIIKV | ++ |
| 67 | LLDVLAPLV | ++ |
| 68 | YVLTQPPSV | ++ |
| 69 | ILADLLPSL | ++ |
| 70 | SLTALRLLL | ++ |
| 71 | ALDGHLYAV | +++ |

TABLE 11-continued

MHC class I binding scores.
Binding of HLA-class I restricted peptides to
HLA-A*02:01 was ranged by peptide exchange yield:
≥10% = +; ≥20% = ++; ≥50 = +++; ≥75% = ++++

| Seq ID | Sequence | Peptide exchange |
|---|---|---|
| 72 | YSLEKVFGI | ++ |
| 73 | GLDGIPFTV | +++ |
| 74 | GLFHKQVTV | +++ |
| 75 | FLIKSINLV | +++ |
| 76 | VLADDHLIEV | ++ |
| 77 | SLIKHKIML | ++ |
| 78 | ALLDTVVQA | ++ |
| 79 | ALADIVWRA | +++ |
| 80 | KLASMLETL | +++ |
| 81 | SLLPALPKL | ++ |
| 82 | SLLQATDFMSL | +++ |
| 83 | IQWSIVPEV | +++ |
| 84 | YLMDEGAHL | ++ |
| 85 | FVMSEIRTV | +++ |
| 86 | GLLQGKLALL | ++ |
| 88 | TLAELHISL | ++ |
| 89 | SLLLAVTEV | ++ |
| 90 | FTLEKNFVI | ++ |
| 91 | MLLSSLVSL | ++ |
| 92 | FLFRDILEL | +++ |
| 93 | GVMAGDIYSV | ++++ |
| 94 | ILHHKVYDL | ++ |
| 95 | KLTDVGIATL | ++ |
| 96 | TLAETLVNL | +++ |
| 97 | TLISELVQA | ++ |
| 98 | KIPPVSPSI | ++ |
| 99 | GLAPHLEQI | ++ |
| 100 | KLNVAPLAV | ++ |
| 101 | HIYDKAFITV | ++ |
| 102 | LLFDVHTTL | +++ |
| 103 | KLQDGLLHI | ++ |
| 104 | ALFEGVVRQI | +++ |
| 105 | ALADLDELLIRA | +++ |
| 106 | VLMDLKALL | +++ |
| 107 | VLMDLKALLL | +++ |
| 108 | VLISVLQAI | ++ |
| 109 | YLWSRVEKL | ++++ |
| 110 | LLDLHSYLL | ++ |
| 111 | TLLETEMLL | ++ |
| 112 | LLFDHLEPIEL | +++ |
| 113 | SLFDWNVKL | +++ |
| 114 | ALAVNISAA | +++ |

Example 6

Absolute Quantitation of Tumor Associated Peptides Presented on the Cell Surface The generation of binders, such as antibodies and/or TCRs, is a laborious process, which may be conducted only for a number of selected targets. In the case of tumor-associated and -specific peptides, selection criteria include but are not restricted to exclusiveness of presentation and the density of peptide presented on the cell surface. The quantitation of TUMAP copies per cell in solid tumor samples requires the absolute quantitation of the isolated TUMAP, the efficiency of TUMAP isolation, and the cell count of the tissue sample analyzed.

Peptide Quantitation by nanoLC-MS/MS

For an accurate quantitation of peptides by mass spectrometry, a calibration curve was generated for each peptide using the internal standard method. The internal standard is a double-isotope-labelled variant of each peptide, i.e. two isotope-labelled amino acids were included in TUMAP synthesis. It differs from the tumor-associated peptide only in its mass but shows no difference in other physicochemical properties (Anderson et al., 2012). The internal standard was spiked to each MS sample and all MS signals were normalized to the MS signal of the internal standard to level out potential technical variances between MS experiments.

The calibration curves were prepared in at least three different matrices, i.e. HLA peptide eluates from natural samples similar to the routine MS samples, and each preparation was measured in duplicate MS runs. For evaluation, MS signals were normalized to the signal of the internal standard and a calibration curve was calculated by logistic regression.

For the quantitation of tumor-associated peptides from tissue samples, the respective samples were also spiked with the internal standard; the MS signals were normalized to the internal standard and quantified using the peptide calibration curve.

Efficiency of Peptide/MHC Isolation

As for any protein purification process, the isolation of proteins from tissue samples is associated with a certain loss of the protein of interest. To determine the efficiency of TUMAP isolation, peptide/MHC complexes were generated for all TUMAPs selected for absolute quantitation. To be able to discriminate the spiked from the natural peptide/MHC complexes, single-isotope-labelled versions of the TUMAPs were used, i.e. one isotope-labelled amino acid was included in TUMAP synthesis. These complexes were spiked into the freshly prepared tissue lysates, i.e. at the earliest possible point of the TUMAP isolation procedure, and then captured like the natural peptide/MHC complexes in the following affinity purification. Measuring the recovery of the single-labelled TUMAPs therefore allows conclusions regarding the efficiency of isolation of individual natural TUMAPs.

The efficiency of isolation was analyzed in a low number of samples and was comparable among these tissue samples. In contrast, the isolation efficiency differs between individual peptides. This suggests that the isolation efficiency, although determined in only a limited number of tissue samples, may be extrapolated to any other tissue preparation. However, it is necessary to analyze each TUMAP individually as the isolation efficiency may not be extrapolated from one peptide to others.

Determination of the Cell Count in Solid, Frozen Tissue

In order to determine the cell count of the tissue samples subjected to absolute peptide quantitation, the inventors applied DNA content analysis. This method is applicable to a wide range of samples of different origin and, most importantly, frozen samples (Alcoser et al., 2011; Forsey and Chaudhuri, 2009; Silva et al., 2013). During the peptide isolation protocol, a tissue sample is processed to a homogenous lysate, from which a small lysate aliquot is taken. The aliquot is divided in three parts, from which DNA is isolated (QiaAmp DNA Mini Kit, Qiagen, Hilden, Germany). The total DNA content from each DNA isolation is quantified using a fluorescence-based DNA quantitation assay (Qubit dsDNA HS Assay Kit, Life Technologies, Darmstadt, Germany) in at least two replicates.

In order to calculate the cell number, a DNA standard curve from aliquots of single healthy blood cells, with a range of defined cell numbers, has been generated. The standard curve is used to calculate the total cell content from the total DNA content from each DNA isolation. The mean total cell count of the tissue sample used for peptide isolation is extrapolated considering the known volume of the lysate aliquots and the total lysate volume.

Peptide Copies Per Cell

With data of the aforementioned experiments, the inventors calculated the number of TUMAP copies per cell by dividing the total peptide amount by the total cell count of the sample, followed by division through isolation efficiency. Copy cell numbers for selected peptides are shown in Table 12.

TABLE 12

Absolute copy numbers.

| SEQ ID No. | Peptide Code | Copies per cell (median) | Number of samples |
|---|---|---|---|
| 1 | SLC17A3-001 | ++ | 18 |

The table lists the results of absolute peptide quantitation in NSCLC tumor samples. The median number of copies per cell are indicated for each peptide: <100 = +; >=100 = ++; >=1,000 +++; >=10,000 = ++++. The number of samples, in which evaluable, high quality MS data are available, is indicated.

REFERENCE LIST

PLoS. One. 10 (2015): e0119247
Agalliu, I. et al., JAMA Neurol. 72 (2015): 58-65
Agesen, T. H. et al., Gut 61 (2012): 1560-1567
Alagaratnam, S. et al., Int. J Androl 34 (2011): e133-e150
Alcoser, S. Y. et al., BMC. Biotechnol. 11 (2011): 124
Alholle, A. et al., Epigenetics. 8 (2013): 1198-1204
Allison, J. P. et al., Science 270 (1995): 932-933
Altman, M. K. et al., Biochem. Res. Int. 2012 (2012): 518437
Amatschek, S. et al., Cancer Res 64 (2004): 844-856
Anastas, J. N. et al., J Clin Invest 124 (2014): 2877-2890
Andersen, R. K. et al., Pigment Cell Melanoma Res. 28 (2015): 267-280
Andersen, R. S. et al., Nat. Protoc. 7 (2012): 891-902
Anderson, L. N. et al., PLoS. One. 8 (2013): e66768
Anderson, N. L. et al., J Proteome. Res 11 (2012): 1868-1878
Antony-Debre, I. et al., Cancer Cell 27 (2015): 609-611
Appay, V. et al., Eur. J Immunol. 36 (2006): 1805-1814
Araujo, W. F. et al., Urol. Oncol (2015)
Arribas, A. J. et al., Blood 125 (2015): 1922-1931
Asad, M. et al., Cell Death. Dis. 5 (2014): e1346
Asaga, S. et al., Anticancer Res. 26 (2006): 35-42
Avery-Kiejda, K. A. et al., BMC. Cancer 14 (2014): 253
Avigan, D. et al., Clin Cancer Res. 10 (2004): 4699-4708
Awasthi, N. et al., Cancer Lett. 358 (2015): 59-66
Ayshamgul, H. et al., Chin Med. J (Engl.) 124 (2011): 341-346
Bae, D. H. et al., J Clin Pathol. 66 (2013): 911-917
Baek, G. et al., Cell Rep. 9 (2014): 2233-2249
Baenke, F. et al., J Pathol. (2015)
Bai, L. et al., J Cell Biochem. 113 (2012): 322-328
Banchereau, J. et al., Cell 106 (2001): 271-274
Bao, B. Y. et al., Clin Cancer Res. 17 (2011): 928-936
Bao, W. et al., Biomed. Pharmacother. 70 (2015): 97-102
Basson, M. D. et al., Mol. Oncol 9 (2015): 513-526
Bauer, K. M. et al., J Proteome. Res. 13 (2014): 4910-4918
Beatty, G. et al., J Immunol 166 (2001): 2276-2282
Bedir, R. et al., Iran J Otorhinolaryngol. 27 (2015): 69-74
Beggs, J. D., Nature 275 (1978): 104-109
Beleford, D. et al., Clin Cancer Res. 16 (2010): 398-409
Bell, J. L. et al., Cell Mol Life Sci. 70 (2013): 2657-2675
Benjamini, Y. et al., Journal of the Royal Statistical Society. Series B (Methodological), Vol. 57 (1995): 289-300
Bhatnagar, R. et al., Oral Oncol 48 (2012): 831-835
Bill, K. L. et al., Lab Invest (2015)
Blanke, K. L. et al., Cancer Causes Control 25 (2014): 1513-1521
Bleumer, I. et al., Eur. Urol. 44 (2003): 65-75
Bonventre, J. V., Trans. Am. Clin Climatol. Assoc. 125 (2014): 293-299
Boulter, J. M. et al., Protein Eng 16 (2003): 707-711
Braumuller, H. et al., Nature (2013)
Brendle, A. et al., Carcinogenesis 29 (2008): 1394-1399
Brossart, P. et al., Blood 90 (1997): 1594-1599
Bruckdorfer, T. et al., Curr. Pharm. Biotechnol. 5 (2004): 29-43
Bunatova, K. et al., Anticancer Res. 32 (2012): 4601-4606
Card, K. F. et al., Cancer Immunol Immunother. 53 (2004): 345-357
Carvalho, F. L. et al., Prostate 74 (2014): 933-945
Chanock, S. J. et al., Hum. Immunol. 65 (2004): 1211-1223
Chatterjee, M. et al., Haematologica 98 (2013): 1132-1141
Chen, K. et al., J Cancer Res. Clin Oncol 140 (2014a): 1715-1721
Chen, Q. et al., PLoS. One. 9 (2014b): e88386
Chen, S. T. et al., Cancer Sci. 102 (2011): 2191-2198
Chen, Y. C. et al., Int. J Cancer 135 (2014c): 117-127
Chen, Y. L. et al., Int J Surg. 11 (2013): 85-91
Cheng, A. S. et al., Gastroenterology 144 (2013): 122-133
Cheng, J. et al., Cancer Lett. 310 (2011): 35-45
Cheon, D. J. et al., Clin Cancer Res 20 (2014): 711-723

Cho, E. et al., Hematol. Oncol. Clin. North Am. 25 (2011): 651-665
Chong, Y. et al., Oncol Rep. 31 (2014): 2535-2544
Chu, X. et al., Asian Pac. J Cancer Prev. 15 (2014): 5819-5823
Cohen, C. J. et al., J Mol Recognit. 16 (2003a): 324-332
Cohen, C. J. et al., J Immunol 170 (2003b): 4349-4361
Cohen, S. N. et al., Proc. Natl. Acad. Sci. U.S.A 69 (1972): 2110-2114
Coligan, J. E. et al., Current Protocols in Protein Science (1995)
Colombetti, S. et al., J Immunol. 176 (2006): 2730-2738
Cuadros, T. et al., Cancer Res 74 (2014): 1416-1428
Cuadros, T. et al., Eur. J Cancer 49 (2013): 2034-2047
D'Angelo, V. et al., J Neurooncol. 117 (2014): 287-294
Dadkhah, E. et al., Arch.Iran Med. 16 (2013): 463-470
Dannenmann, S. R. et al., Cancer Immunol. Res. 1 (2013): 288-295
Davidov, T. et al., J Surg. Res. 190 (2014): 565-574
Deng, B. et al., Tumour. Biol. (2015)
Dengjel, J. et al., Clin Cancer Res 12 (2006): 4163-4170
Denkberg, G. et al., J Immunol 171 (2003): 2197-2207
Devaney, J. M. et al., Prostate Cancer Prostatic. Dis. 16 (2013): 292-300
Dey, N. et al., PLoS. One. 8 (2013): e77425
Dienstmann, R. et al., Am. Soc. Clin Oncol Educ. Book. 35 (2015): e149-e156
Ding, L. C. et al., Oncol Rep. (2015)
Dong, R. et al., PLoS. One. 9 (2014): e85599
El Behery, M. M. et al., Arch. Gynecol. Obstet. 288 (2013): 1371-1376
Elewa, M. A. et al., Clin Exp. Metastasis (2015)
Elouazzani, H. et al., J Clin Imaging Sci. 4 (2014): 33
Falk, K. et al., Nature 351 (1991): 290-296
Fan, H. Z. et al., J Cancer Res. Clin Oncol 135 (2009): 591-602
Fang, Z. Q. et al., Genet. Mol Res 12 (2013): 1479-1489
Fei, J. et al., Tumour. Biol. 34 (2013): 2329-2335
Felizola, S. J. et al., J Steroid Biochem. Mol. Biol. 144 Pt B (2014): 410-416
Feng, H. et al., J Clin Invest 124 (2014): 3741-3756
Ferguson, B. W. et al., BMC. Cancer 13 (2013): 593
Fernandez-Banet, J. et al., Genomics 103 (2014): 189-203
Ferrer-Ferrer, M. et al., Arch. Med. Res 44 (2013): 467-474
Findeis-Hosey, J. J. et al., Biotech. Histochem. 87 (2012): 24-29
Finocchiaro, G. et al., Ann. Transl. Med. 3 (2015): 83
Fleischer, M. et al., Genes Chromosomes. Cancer 50 (2011): 1010-1020
Fong, L. et al., Proc. Natl. Acad. Sci. U.S.A 98 (2001): 8809-8814
Fontes-Oliveira, C. C. et al., Biochim. Biophys. Acta 1830 (2013): 2770-2778
Forconi, F. et al., Haematologica 93 (2008): 697-705
Forloni, M. et al., Cancer Res. 70 (2010): 916-924
Forsey, R. W. et al., Biotechnol. Lett. 31 (2009): 819-823
Franco, R. et al., Histol. Histopathol. 30 (2015): 707-714
Fu, Q. F. et al., J Hematol. Oncol 8 (2015): 22
Fu, Y. et al., Mol. Biol. Rep. 38 (2011): 693-702
Fujinaga, T. et al., Int. J Oncol 44 (2014): 1614-1624
Gabrilovich, D. I. et al., Nat Med. 2 (1996): 1096-1103
Gackiere, F. et al., Biol. Open. 2 (2013): 941-951
Gadd, S. et al., Lab Invest 90 (2010): 724-738
Gantsev, S. K. et al., Biomed. Pharmacother. 67 (2013): 363-366
Gao, H. et al., Cancer Lett. 344 (2014): 54-61
Gao, H. J. et al., J Cancer Res. Clin Oncol 141 (2015a): 1151-1162
Gao, W. et al., BMC. Cancer 15 (2015b): 367
Garg, M. et al., Cancer 116 (2010a): 3785-3796
Garg, M. et al., Eur. J Cancer 46 (2010b): 207-215
Garner, J. M. et al., PLoS. One. 10 (2015): e0125838
Gattinoni, L. et al., Nat Rev. Immunol 6 (2006): 383-393
Gbormittah, F. O. et al., J Proteome. Res. 13 (2014): 4889-4900
Gilkes, D. M. et al., Mol Cancer Res 11 (2013): 456-466
Giovannetti, E. et al., J Natl. Cancer Inst. 106 (2014): djt346
Gnjatic, S. et al., Proc Natl. Acad. Sci. U.S.A 100 (2003): 8862-8867
Godkin, A. et al., Int. Immunol 9 (1997): 905-911
Goksel, G. et al., J BUON. 19 (2014): 207-214
Gomez-Villafuertes, R. et al., J Neurochem. 131 (2014): 290-302
Gong, Y. et al., Adv. Anat. Pathol. 21 (2014): 191-200
Gonzalez, J. E. et al., J Am. Acad. Audiol. 25 (2014): 253-260
Goode, G. et al., PLoS. One. 9 (2014): e100103
Granja, S. et al., Oncotarget. 6 (2015): 6708-6721
Green, M. R. et al., Molecular Cloning, A Laboratory Manual 4th (2012)
Greenfield, E. A., Antibodies: A Laboratory Manual 2nd (2014)
Griffith, O. L. et al., J Clin. Oncol. 24 (2006): 5043-5051
Grunewald, T. G. et al., Biol. Cell 105 (2013): 535-547
Guerrero-Preston, R. et al., Epigenetics. 9 (2014): 1031-1046
Guo, P. et al., Onco. Targets. Ther. 8 (2015): 73-79
Halldorsdottir, A. M. et al., Am. J Hematol. 87 (2012): 361-367
Han, B. et al., Mol. Cancer 14 (2015): 64
Havens, M. A. et al., PLoS.Genet. 10 (2014): e1004312
Heist, R. S. et al., Proc. Natl. Acad. Sci. U.S.A 112 (2015): 1547-1552
Hevir-Kene, N. et al., Chem Biol. Interact. 234 (2015): 309-319
Hirota, E. et al., Int. J Oncol. 29 (2006): 799-827
Hlavac, V. et al., Medicine (Baltimore) 93 (2014): e255
Hoffmann, N. E. et al., Cancer 112 (2008): 1471-1479
Hofmann, H. S. et al., Eur. Urol. 48 (2005): 77-81
Hogan, L. E. et al., Blood 118 (2011): 5218-5226
Holtl, L. et al., Clin. Cancer Res. 8 (2002): 3369-3376
Honke, K. et al., J Biochem. 119 (1996): 421-427
Hovnanian, A., Subcell. Biochem. 45 (2007): 337-363
Hu, C. A. et al., FEBS Lett. 586 (2012): 947-955
Hu, M. et al., J Surg. Oncol 108 (2013): 192-196
Hu, S. et al., J Cancer Res Clin Oncol 140 (2014): 883-893
Hu, Y. et al., Mol. Cancer Ther. 14 (2015): 289-297
Hua, D. et al., Int. J Mol Med. 30 (2012): 1267-1274
Huang, C. N. et al., Ann. Oncol 23 (2012a): 707-713
Huang, G. et al., J Surg. Oncol 105 (2012b): 420-424
Huang, Y. et al., Cell Biosci. 3 (2013): 16
Hung, T. H. et al., Int. J Biochem. Cell Biol. 53 (2014): 55-65
Hunt, J. D. et al., Int. J Cancer 114 (2005): 101-108
Hwang, M. L. et al., J Immunol. 179 (2007): 5829-5838
Illm, K. et al., Mol. Cancer 14 (2015): 38
Inoue, Y. et al., Cancer Chemother. Pharmacol. (2015)
Inzelberg, R. et al., Neurology 78 (2012): 781-786
Ishiguro, Y. et al., Gan 75 (1984): 53-60
Jeng, Y. M. et al., Br. J Surg. 96 (2009): 66-73
Jensen, D. H. et al., J Oral Pathol. Med. (2014)
Jiang, J. G. et al., Cancer Res 65 (2005): 4707-4715
Jiao, J. et al., Cancer Lett. 320 (2012): 96-103

Jin, Z. et al., Anticancer Res. 33 (2013): 5199-5203
Joerger, M. et al., Prostate Cancer Prostatic. Dis. 18 (2015): 167-172
Johnson, R. H. et al., Oncotarget. (2015)
Jose-Eneriz, E. S. et al., Br. J Haematol. 142 (2008): 571-582
Jung, G. et al., Proc Natl Acad Sci USA 84 (1987): 4611-4615
Junnila, S. et al., BMC. Cancer 10 (2010): 73
Kamphausen, E. et al., Cancer Immunol. Immunother. 59 (2010): 1273-1284
Kang, M. R. et al., J Pathol. 217 (2009): 702-706
Karagiannis, G. S. et al., Mol. Oncol 8 (2014): 1240-1252
Katoh, M. et al., Oncol Rep. 13 (2005): 367-370
Kawahara, R. et al., PLoS. One. 9 (2014): el 15004
Kawakami, K. et al., Int. J Oncol (2015)
Khan, R. et al., Clin. Proteomics. 10 (2013a): 6
Khan, Z. et al., Cancer Invest 31 (2013b): 404-411
Kibbe, A. H., Handbook of Pharmaceutical Excipients rd (2000)
Kim, J. H. et al., J Korean Med. Sci. 8 (1993): 68-72
Kim, J. S. et al., Cancer Biol. Ther. 13 (2012): 638-646
Kim, M. et al., Mol Cancer Res 6 (2008): 222-230
Kirov, A. et al., J Cell Biochem. (2015)
Kleiber, K. et al., Anticancer Res. 27 (2007): 55-61
Kobayashi, H. et al., Oncol Lett. 10 (2015): 612-618
Koh, J. et al., Mol. Endocrinol. 25 (2011): 867-876
Komatsu, S. et al., Br. J Cancer 112 (2015): 357-364
Konno, R., Hum. Cell 14 (2001): 261-266
Koo, J. S. et al., Am. J Clin Pathol. 143 (2015): 584-592
Korosec, B. et al., Cancer Genet. Cytogenet. 171 (2006): 105-111
Koshikawa, K. et al., Oncogene 21 (2002): 2822-2828
Krieg, A. M., Nat Rev. Drug Discov. 5 (2006): 471-484
Kuang, S. Q. et al., Leukemia 22 (2008): 1529-1538
Kubota, H. et al., Cell Stress. Chaperones. 15 (2010): 1003-1011
Kumps, C. et al., PLoS. One. 8 (2013): e52321
Kwon, J. et al., Int J Oncol 43 (2013): 1523-1530
Lai, K. K. et al., PLoS.Genet. 7 (2011): e1002147
Lai, Y. J. et al., Mol. Cell Biol. 30 (2010): 5582-5596
Lapointe, J. et al., Endocrinology 140 (1999): 4486-4493
Lebdai, S. et al., Urol. Oncol 33 (2015): 69-8
Lee, H. J. et al., Oncol Lett. 8 (2014): 1986-1992
Lee, H. K. et al., Oncotarget. 6 (2015): 1850-1864
Lee, J. et al., Yonsei Med. J 54 (2013): 1158-1167
Li, J. et al., J Mol. Histol. 45 (2014a): 47-57
Li, M. et al., Int. J Oncol. 24 (2004): 305-312
Li, R. et al., Curr. Cancer Drug Targets. 14 (2014b): 274-285
Li, W. et al., Int. J Clin Exp. Pathol. 6 (2013): 2430-2440
Li, X. X. et al., Int. J Clin Exp. Pathol. 7 (2014c): 2729-2736
Li, Y. et al., BMC. Cancer 15 (2015): 417
Liddy, N. et al., Nat Med. 18 (2012): 980-987
Lin, L. et al., Oncol Lett. 6 (2013): 740-744
Lin, M. C. et al., Oral Oncol 50 (2014): 478-484
Lin, Y. W. et al., Eur. J Cancer 45 (2009): 2041-2049
Lin, Z. Y. et al., Biomed. Pharmacother. 66 (2012): 454-458
Liu, B. et al., Zhonghua Fu Chan Ke. Za Zhi. 45 (2010a): 41-44
Liu, F. et al., World J Surg. Oncol 12 (2014a): 333
Liu, H. et al., Carcinogenesis 34 (2013): 885-892
Liu, J. et al., Oncotarget. (2015)
Liu, K. et al., Tumour. Biol. 35 (2014b): 995-1002
Liu, S. et al., Tumour. Biol. 35 (2014c): 9897-9904
Liu, Y. et al., J Neurooncol. 99 (2010b): 13-24
Liu, Y. et al., Mol. Cancer 9 (2010c): 186
Ljungberg, B. et al., Eur. Urol. 60 (2011): 615-621
Ljunggren, H. G. et al., J Exp. Med. 162 (1985): 1745-1759
Longenecker, B. M. et al., Ann N.Y.Acad. Sci. 690 (1993): 276-291
Lourenco, G. J. et al., Breast Cancer Res Treat. 100 (2006): 335-338
Lu, Y. Y. et al., Zhongguo Shi Yan. Xue. Ye. Xue. Za Zhi. 22 (2014): 1336-1340
Lukas, T. J. et al., Proc. Natl. Acad. Sci. U.S.A 78 (1981): 2791-2795
Lundblad, R. L., Chemical Reagents for Protein Modification 3rd (2004)
Lung, H. L. et al., Int. J Cancer 127 (2010): 304-312
Lustosa, S. A. et al., ScientificWorldJournal. 2014 (2014): 102541
Lv, Z. et al., Tumour. Biol. 35 (2014): 10497-10502
Ma, G. F. et al., Eur. Rev. Med. Pharmacol. Sci. 19 (2015): 578-585
Ma, J. et al., Pathol. Oncol Res 19 (2013): 821-832
Mak, A. B. et al., J Mol. Biol. 426 (2014): 2175-2182
Malik, M. A. et al., Mol. Biol. Rep. 39 (2012): 9095-9104
Marten, A. et al., Cancer Immunol. Immunother. 51 (2002): 637-644
Martinez-Lopez, N. et al., Gastroenterology 143 (2012): 787-798
Massari, F. et al., Cancer Treat. Rev. 41 (2015): 114-121
Masugi, Y. et al., Lab Invest 95 (2015): 308-319
Matsubara, J. et al., Cancer Epidemiol. Biomarkers Prev. 20 (2011): 2195-2203
Mehta, A. M. et al., Immunogenetics 67 (2015): 267-275
Mei, J. et al., Oncogene 25 (2006): 849-856
Mertens-Walker, I. et al., BMC. Cancer 15 (2015): 164
Meziere, C. et al., J Immunol 159 (1997): 3230-3237
Michael, A. et al., Lancet Oncol. 4 (2003): 215-223
Minami, T. et al., Int. Immunopharmacol. 20 (2014): 59-65
Minchenko, O. H. et al., World J Gastroenterol. 20 (2014): 13705-13717
Miyoshi, N. et al., Oncol Rep. 23 (2010): 505-510
Mo, Y. et al., Cancer Lett. 323 (2012): 147-154
Moch, H., Semin. Cancer Biol. 23 (2013): 3-9
Mochizuki, S. et al., Cancer Sci. 98 (2007): 621-628
Mohelnikova-Duchonova, B. et al., Cancer Chemother. Pharmacol. 72 (2013a): 669-682
Mohelnikova-Duchonova, B. et al., Pancreas 42 (2013b): 707-716
Molina-Pinelo, S. et al., PLoS. One. 9 (2014): e90524
Morgan, R. A. et al., Science 314 (2006): 126-129
Mori, M. et al., Transplantation 64 (1997): 1017-1027
Moriya, Y. et al., Oral Oncol 51 (2015): 84-89
Morrissey, J. J. et al., Urology 83 (2014): 256-14
Mortara, L. et al., Clin Cancer Res. 12 (2006): 3435-3443
Motzer, R. J. et al., Clin. Cancer Res. 10 (2004): 6302S-6303S
Moutinho, C. et al., J Natl. Cancer Inst. 106 (2014): djt322
Mueller, L. N. et al., J Proteome. Res 7 (2008): 51-61
Mueller, L. N. et al., Proteomics. 7 (2007): 3470-3480
Mukai, M. et al., Am. J Surg. Pathol. 10 (1986): 212-218
Mumberg, D. et al., Proc. Natl. Acad. Sci. U.S.A 96 (1999): 8633-8638
Mustafa, D. A. et al., Gene Regul. Syst. Bio 4 (2010): 103-107
Nagy, Z. et al., Mol. Cancer 13 (2014): 96
Nakai, Y. et al., J Cancer Res. Clin Oncol 141 (2015): 933-939
Narjoz, C. et al., PLoS. One. 9 (2014): e95532
Narkiewicz, J. et al., Oncol Rep. 21 (2009): 1529-1537
Naryzhnyi, S. N. et al., Biomed. Khim. 60 (2014): 308-321
Ng, K. T. et al., Mol. Cancer 13 (2014): 196

Nguyen, H. et al., J Biol. Chem 290 (2015): 13641-13653
Ni, I. B. et al., Hematol. Rep. 4 (2012): e19
Nikitovic, D. et al., Biochim. Biophys. Acta 1840 (2014): 2471-2481
Nimptsch, K. et al., Cancer Epidemiol. Biomarkers Prev. 18 (2009): 49-56
Nishio, S. et al., Cancer Lett. 264 (2008): 36-43
Notaridou, M. et al., Int. J Cancer 128 (2011): 2063-2074
Nowak, D. et al., Blood 115 (2010): 1049-1053
Oka, K. et al., Lab Invest 60 (1989): 38-44
Okudela, K. et al., PLoS. One. 9 (2014): e87193
Olesen, S. H. et al., Mol Cell Proteomics. 4 (2005): 534-544
Ozawa, D. et al., Ann. Surg. Oncol (2014)
Paradis, V. et al., Gut 62 (2013): 911-919
Pathan, N. et al., J Biol. Chem 276 (2001): 32220-32229
Pavlikova, N. et al., Exp. Cell Res. 333 (2015): 1-10
Pedersen, M. O. et al., Leuk. Lymphoma 51 (2010): 314-328
Penning, T. M., Chem Res. Toxicol. 27 (2014): 1901-1917
Pereira, P. M. et al., Org. Biomol. Chem. 12 (2014): 1804-1811
Peters, D. G. et al., Cancer Epidemiol. Biomarkers Prev. 14 (2005): 1717-1723
Petrini, I., Ann. Transl. Med. 3 (2015): 82
Pinheiro, J. et al., nlme: Linear and Nonlinear Mixed Effects Models (CRAN.R-project.org/packe=nlme) (2015)
Planutis, K. et al., J Transl. Med. 11 (2013): 50
Plebanski, M. et al., Eur. J Immunol 25 (1995): 1783-1787
Porta, C. et al., Virology 202 (1994): 949-955
Prakash, S. et al., J Pediatr. Hematol. Oncol 27 (2005): 179-187
Principe, M. et al., Oncotarget. 6 (2015): 11098-11113
Qian, Z. et al., Chem Biol. Interact. 184 (2010): 50-57
Quinn, M. C. et al., Int J Oncol 42 (2013): 912-920
Ragnum, H. B. et al., Int. J Radiat. Oncol Biol. Phys. 87 (2013): 753-760
Ramazzotti, G. et al., Crit Rev. Eukaryot. Gene Expr. 21 (2011): 291-301
Rammensee, H. G. et al., Immunogenetics 50 (1999): 213-219
RefSeq, The NCBI handbook [Internet], Chapter 18, (2002), www.ncbi.nlm.nih.gov/books/NBK21091/
Rehfeld, A. et al., Front Endocrinol. (Lausanne) 5 (2014): 46
Ren, Y. et al., Mol. Cell Proteomics. 13 (2014): 3126-3137
Renehan, A. G. et al., Int. J Cancer 126 (2010): 692-702
Renehan, A. G. et al., Lancet 371 (2008): 569-578
Renkvist, N. et al., Cancer Immunol. Immunother. 50 (2001): 3-15
Richardson, A. et al., Crit Rev. Oncog. 18 (2013): 409-434
Rini, B. I. et al., Curr. Opin. Oncol. 20 (2008): 300-306
Rini, B. I. et al., Cancer 107 (2006): 67-74
Rock, K. L. et al., Science 249 (1990): 918-921
Rocken, C. et al., Pathologe 33 Suppl 2 (2012): 235-240
Rodenko, B. et al., Nat Protoc. 1 (2006): 1120-1132
Royds, J. A. et al., J Clin Pathol. 38 (1985): 1258-1260
Ruiz-Martinez, J. et al., Mov Disord. 29 (2014): 750-755
Sachdeva K et al., emedicine.medscape.com/article/281340-overview (2010)
Sahasrabuddhe, N. A. et al., Biochem. Biophys. Res. Commun. 446 (2014): 863-869
Saiki, R. K. et al., Science 239 (1988): 487-491
Sakamoto, L. H. et al., Leuk. Res. 38 (2014): 496-502
Sasnauskiene, A. et al., Medicina (Kaunas.) 50 (2014): 14-18
Sato, T. et al., PLoS. One. 8 (2013): e59444
Schlomann, U. et al., Nat Commun. 6 (2015): 6175
Schuetz, A. N. et al., J Mol. Diagn. 7 (2005): 206-218
Schumann, T. et al., Oncotarget. (2015)
Scrideli, C. A. et al., Leuk. Res. 34 (2010): 32-37
Sedlakova, I. et al., Int. J Gynecol. Cancer 25 (2015): 236-243
Seeger, F. H. et al., Immunogenetics 49 (1999): 571-576
Seong, J. et al., Mol. Biol. Rep. 39 (2012): 3597-3601
Sethakorn, N. et al., J Recept. Signal. Transduct. Res. 33 (2013): 166-171
Sherman, F. et al., Laboratory Course Manual for Methods in Yeast Genetics (1986)
Shu, J. et al., Cancer Res. 66 (2006): 5077-5084
Shukla, S. et al., Cancer Res. 73 (2013): 6563-6573
Sieuwerts, A. M. et al., Clin. Chem 53 (2007): 1280-1288
Sigari, N. et al., Clin Lab 60 (2014): 23-27
Silva, L. P. et al., Anal. Chem. 85 (2013): 9536-9542
Singh, S. et al., Tumour. Biol. (2014)
Singh-Jasuja, H. et al., Cancer Immunol. Immunother. 53 (2004): 187-195
Slater, E. P. et al., Transl. Oncol. 6 (2013): 99-103
Small, E. J. et al., J Clin Oncol. 24 (2006): 3089-3094
Song, J. et al., PLoS. One. 9 (2014): el 110074
Sowalsky, A. G. et al., Mol. Cancer Res. 13 (2015): 98-106
Sprowl, J. A. et al., Clin Pharmacol. Ther. 94 (2013): 585-592
Staal-Viliare, A. et al., Leuk. Lymphoma 48 (2007): 439-441
Staehli, F. et al., J Immunol. 188 (2012): 3820-3828
Stamatopoulos, K. et al., Blood 106 (2005): 3575-3583
Stein, U., Expert. Opin. Ther. Targets. 17 (2013): 1039-1052
Steinway, S. N. et al., PLoS. One. 10 (2015): e0128159
Stoehr, C. G. et al., Int. J Clin Exp. Pathol. 6 (2013): 998-1008
Strekalova, E. et al., Clin. Cancer Res. (2015)
Sturm, M. et al., BMC. Bioinformatics. 9 (2008): 163
Su, H. et al., J Transl. Med. 13 (2015): 104
Su, Z. et al., Cancer Res. 63 (2003): 2127-2133
Suh, K. S. et al., Clin. Cancer Res. 13 (2007a): 121-131
Suh, K. S. et al., Mol. Carcinog. 46 (2007b): 599-604
Suhovskih, A. V. et al., Cell Tissue Res. (2015)
Sun, W. et al., Cancer Res. 74 (2014a): 1091-1104
Sun, Z. et al., J Proteome. Res 13 (2014b): 1593-1601
Szarvas, T. et al., Int J Cancer 135 (2014): 1596-1604
Taguchi, O. et al., Clin Chim. Acta 244 (1996): 69-81
Tam, C. W. et al., Endocrinology 147 (2006): 5023-5033
Tan, M. H. et al., Breast Cancer Res. Treat. 131 (2012): 849-858
Tanaka, J. et al., J Oral Pathol. Med. 44 (2015): 126-133
Tanaka, T. et al., J Cancer Res. Clin Oncol 140 (2014): 503-513
Tanic, N. et al., Anticancer Res. 26 (2006): 2137-2142
Tashiro, A. et al., Am. J Cancer Res. 4 (2014): 528-536
Teufel, R. et al., Cell Mol Life Sci. 62 (2005): 1755-1762
Thiel, A. et al., Oncol Rep. 26 (2011): 615-620
Tong, S. Y. et al., Cancer Invest 30 (2012): 642-645
Tong, W. G. et al., Epigenetics. 5 (2010): 499-508
Toth, K. et al., Appl. Immunohistochem. Mol. Morphol. 22 (2014): 642-647
Tran, E. et al., Science 344 (2014a): 641-645
Tran, T. T. et al., Photochem. Photobiol. 90 (2014b): 1136-1143
Tsourlakis, M. C. et al., Int. J Mol. Sci. 16 (2015): 8591-8606
Vachani, A. et al., Clin Cancer Res. 13 (2007): 2905-2915
Vasiljevic, A. et al., Neuropathology. 33 (2013): 149-161
Volz, N. B. et al., Pharmacogenomics. J 15 (2015): 69-76
Wake, N. C. et al., Hum. Mutat. 34 (2013): 1650-1661
Walter, S. et al., J Immunol 171 (2003): 4974-4978
Walter, S. et al., Nat Med. 18 (2012): 1254-1261

Wang, B. S. et al., Cell Stress. Chaperones. 18 (2013a): 359-366
Wang, D. et al., Mol. Cell Biochem. 396 (2014a): 67-77
Wang, G. et al., Tumour. Biol 36 (2015a): 1055-1065
Wang, H. et al., J Biol. Chem 289 (2014b): 4009-4017
Wang, J. H. et al., World J Gastroenterol. 16 (2010a): 5642-5646
Wang, L. H. et al., Tumour. Biol. 35 (2014c): 1157-1168
Wang, R. et al., Biomed. Res. Int. 2013 (2013b): 195692
Wang, T. P. et al., Exp. Cell Res. 316 (2010b): 2893-2902
Wang, W. M. et al., Mol. Med. Rep. (2015b)
Wang, Y. et al., J Biol. Chem 289 (2014d): 14225-14238
Wang, Y. et al., Clin. Chem Lab Med. 48 (2010c): 1475-1479
Wang, Y. et al., Anticancer Res 33 (2013c): 207-214
Wang, Y. et al., Pathol. Oncol Res. 20 (2014): 611-618
Wang, Z. et al., J Cancer Res Clin Oncol 141 (2015c): 1353-1361
Warren, C. R. et al., J Cell Biochem. 115 (2014): 1322-1333
Waugh, M. G., Mol. Neurobiol. (2014)
Wei, Q. et al., Cancer Res. 69 (2009): 2332-2339
Westphal, P. et al., Am. J Clin Pathol. 143 (2015): 248-256
Wierecky, J. et al., Cancer Res. 66 (2006): 5910-5918
Wikman, H. et al., PLoS. One. 7 (2012): e47537
Willcox, B. E. et al., Protein Sci. 8 (1999): 2418-2423
Wittig, B. et al., Hum. Gene Ther. 12 (2001): 267-278
Wlodarski, M. W. et al., J Leukoc. Biol 83 (2008): 589-601
World Cancer Report, (2014)
World Health Organization Classification of Tumours, (2004)
Wu, M. et al., Oncogene 23 (2004): 6815-6819
Wu, Y. M. et al., Cancer Res 71 (2011): 7270-7279
Xiao, L. et al., Biochim. Biophys. Acta (2015)
Xiao, W. et al., Mol. Med. Rep. 10 (2014): 453-458
Xin, Z. et al., Virchows Arch. 465 (2014): 35-47
Xu, Y. et al., J Cell Biochem. 115 (2014): 1112-1121
Xu, Z. et al., Oncol Rep. 33 (2015): 2899-2907
Yamamoto, M. et al., Cancer Res. 65 (2005): 8706-8714
Yan, P. et al., Asian Pac. J Cancer Prev. 15 (2014): 8923-8929
Yang, C. Y. et al., J Immunol 192 (2014a): 1547-1557
Yang, D. et al., Oncogene 30 (2011): 4590-4600
Yang, J. et al., J Proteomics. 109 (2014b): 162-175
Yang, W. et al., Med. Oncol 31 (2014c): 826
Yang, W. et al., Tumour. Biol. 35 (2014d): 8267-8279
Yano, Y. et al., Cancer Lett. 207 (2004): 139-147
Yao, Y. et al., Cell Physiol Biochem. 35 (2015): 983-996
Yeh, I. et al., Nat. Commun. 6 (2015): 7174
Yeom, S. Y. et al., Mol. Cancer Ther. 13 (2014): 3049-3061
Yin, Y. et al., Tumour. Biol. 34 (2013): 3611-3617
Yoshida, A. et al., Hum. Cell 26 (2013): 56-66
Yoshida, Y. et al., Anticancer Res. 32 (2012): 2301-2308
Yu, P. H. et al., PLoS. One. 8 (2013): e82254
Yu, Z. et al., Cancer Lett. 353 (2014): 182-193
Yuan, R. H. et al., Ann Surg. Oncol 16 (2009): 1711-1719
Zaghloul, R. A. et al., Eur. J Pharmacol. 746 (2015): 353-362
Zamani-Ahmadmahmudi, M. et al., Electrophoresis 35 (2014): 901-910
Zaremba, S. et al., Cancer Res. 57 (1997): 4570-4577
Zhang, B. et al., Blood 106 (2005): 1355-1361
Zhang, H. et al., Cancer Lett. 323 (2012a): 106-113
Zhang, J. et al., Mol. Med. Rep. 10 (2014a): 749-754
Zhang, J. et al., Xi. Bao. Yu Fen. Zi. Mian. Yi. Xue. Za Zhi. 29 (2013): 190-193
Zhang, L. et al., Dig. Dis. Sci. 57 (2012b): 2608-2614
Zhang, S. D. et al., Onco. Targets. Ther. 8 (2015): 835-843
Zhang, X. D. et al., Int. J Clin Exp. Med. 7 (2014b): 1190-1196
Zhao, M. et al., Cancer Invest 32 (2014): 464-469
Zhao, M. et al., Oncotarget. (2015a)
Zhao, Z. et al., Med. Oncol 32 (2015b): 112
Zhen, T. et al., Oncotarget. 5 (2014): 3756-3769
Zhou, J. et al., Oncol Rep. 30 (2013): 2229-2237
Zhu, J. et al., Int. J Clin Exp. Pathol. 8 (2015): 702-710
Zienert, E. et al., Cancer Lett. 364 (2015): 17-24
Zietek, Z. et al., Pol. Tyg. Lek. 51 (1996): 86-88
Zizi-Sermpetzoglou, A. et al., Eur. J Gynaecol. Oncol 35 (2014): 325-327
Zu, X. Y. et al., Recent Pat Anticancer Drug Discov. 7 (2012): 154-167
Zubor, P. et al., Mol. Biol. Rep. 42 (2015): 977-988
Zuniga-Garcia, V. et al., Dig. Dis. Sci. (2015)
Zurawa-Janicka, D. et al., Oncol Rep. 28 (2012): 1838-1844
Follenzi A, et al. Nat Genet. 2000 June; 25(2):217-22.
Zufferey R, et al. J Virol. 1999 April; 73(4):2886-92.
Scholten K B, et al. Clin Immunol. 2006 May; 119(2):135-45.
Gustafsson C, et al. Trends Biotechnol. 2004 July; 22(7): 346-53. Review.
Kuball, J., et al. (2007). Blood 109, 2331-2338.
Schmitt, T. M., et al. (2009). Hum. Gene Ther. 20, 1240-1248

The invention claimed is:

1. A method of eliciting an immune response in a patient who has cancer, comprising administering to said patient a population of activated T cells that kill cancer cells that aberrantly present a peptide consisting of the amino acid sequence selected from SEQ ID NOs: 3-5, and 8,
wherein said cancer is selected from kidney cancer, lung cancer, brain cancer, stomach cancer, colon or rectal cancer, liver cancer, pancreatic cancer, prostate cancer, leukemias, breast cancer, melanoma, ovarian cancer, and esophageal cancer.

2. The method of claim 1, wherein the T cells are autologous to the patient.

3. The method of claim 1, wherein the T cells are obtained from a healthy donor.

4. The method of claim 1, wherein the T cells are obtained from tumor infiltrating lymphocytes or peripheral blood mononuclear cells.

5. The method of claim 1, wherein the activated T cells are expanded in vitro.

6. The method of claim 1, wherein the population of activated T cells are administered in the form of a composition.

7. The method of claim 6, wherein the composition further comprises an adjuvant.

8. The method of claim 7, wherein the adjuvant is selected from anti-CD40 antibody, imiquimod, resiquimod, GM-CSF, cyclophosphamide, sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

9. A method of treating a patient who has cancer, comprising administering to said patient a population of activated T cells that kill cancer cells that aberrantly present a peptide consisting of the amino acid sequence selected from SEQ ID NOs: 3-5, and 8;
wherein said cancer is selected from the group consisting of kidney cancer, lung cancer, brain cancer, stomach cancer, colon or rectal cancer, liver cancer, pancreatic cancer, prostate cancer, leukemias, breast cancer, melanoma, ovarian cancer, and esophageal cancer.

10. The method of claim 9, wherein the activated T cells are cytotoxic T cells produced by contacting T cells with an antigen presenting cell that presents the peptide in a complex with an MHC class I molecule on the surface of the antigen presenting cell, for a period of time sufficient to activate said T cell.

11. The method of claim 1, wherein the peptide consists of the amino acid sequence SEQ ID NO: 3.

12. The method of claim 1, wherein the peptide consists of the amino acid sequence SEQ ID NO: 4.

13. The method of claim 1, wherein the peptide consists of the amino acid sequence SEQ ID NO: 5.

14. The method of claim 1, wherein the peptide consists of the amino acid sequence SEQ ID NO: 8.

15. The method of claim 9, wherein the peptide consists of the amino acid sequence SEQ ID NO: 3.

16. The method of claim 9, wherein the peptide consists of the amino acid sequence SEQ ID NO: 4.

17. The method of claim 9, wherein the peptide consists of the amino acid sequence SEQ ID NO: 5.

18. The method of claim 9, wherein the peptide consists of the amino acid sequence SEQ ID NO: 8.

19. The method of claim 7, wherein the adjuvant comprises IL-2.

20. The method of claim 7, wherein the adjuvant comprises IL-7.

21. The method of claim 7, wherein the adjuvant comprises IL-12.

22. The method of claim 7, wherein the adjuvant comprises IL-15.

23. The method of claim 7, wherein the adjuvant comprises IL-21.

* * * * *

SEQUENCE LISTING

```
<160> NUMBER OF SEQ ID NOS: 153

<210> SEQ ID NO 1
<211> LENGTH: 9
<212> TYPE: PRT
<213> ORGANISM: Homo sapiens

<400> SEQUENCE: 1

Ala Leu Ile Val Ser Leu Pro Tyr Leu
1               5

<210> SEQ ID NO 2
<211> LENGTH: 9
<212> TYPE: PRT
<213> ORGANISM: Homo sapiens

<400> SEQUENCE: 2
```

Ile Leu Trp Arg Glu Val Val Thr Leu
1               5

<210> SEQ ID NO 3
<211> LENGTH: 9
<212> TYPE: PRT
<213> ORGANISM: Homo sapiens

<400> SEQUENCE: 3

Arg Leu Leu Gly Glu Val Gln Ala Leu
1               5

<210> SEQ ID NO 4
<211> LENGTH: 9
<212> TYPE: PRT
<213> ORGANISM: Homo sapiens

<400> SEQUENCE: 4

Phe Leu Ser Gln Asp Ile Ile Thr Val
1               5

<210> SEQ ID NO 5
<211> LENGTH: 9
<212> TYPE: PRT
<213> ORGANISM: Homo sapiens

<400> SEQUENCE: 5

Tyr Leu Tyr Pro Asn Leu Thr Arg Leu
1               5

<210> SEQ ID NO 6
<211> LENGTH: 9
<212> TYPE: PRT
<213> ORGANISM: Homo sapiens

<400> SEQUENCE: 6

Val Leu Phe Glu Leu Ser Lys Thr Val
1               5

<210> SEQ ID NO 7
<211> LENGTH: 9
<212> TYPE: PRT
<213> ORGANISM: Homo sapiens

<400> SEQUENCE: 7

Phe Leu Leu Ser Leu Ile Asp Arg Leu
1               5

<210> SEQ ID NO 8
<211> LENGTH: 9
<212> TYPE: PRT
<213> ORGANISM: Homo sapiens

<400> SEQUENCE: 8

Gly Leu Ala Ser Phe Lys Ser Phe Leu
1               5

<210> SEQ ID NO 9
<211> LENGTH: 9
<212> TYPE: PRT
<213> ORGANISM: Homo sapiens

<400> SEQUENCE: 9

Ile Leu Leu Gln Lys Pro Asp Ser Val
1               5

```
<210> SEQ ID NO 10
<211> LENGTH: 9
<212> TYPE: PRT
<213> ORGANISM: Homo sapiens

<400> SEQUENCE: 10

Lys Leu Leu Gln Asn Asn Tyr Gly Leu
1               5

<210> SEQ ID NO 11
<211> LENGTH: 10
<212> TYPE: PRT
<213> ORGANISM: Homo sapiens

<400> SEQUENCE: 11

Phe Ile Gln Thr Glu Ala Pro Lys Glu Val
1               5                   10

<210> SEQ ID NO 12
<211> LENGTH: 10
<212> TYPE: PRT
<213> ORGANISM: Homo sapiens

<400> SEQUENCE: 12

Ala Leu Asp Pro Ser Gly Asn Gln Leu Ile
1               5                   10

<210> SEQ ID NO 13
<211> LENGTH: 9
<212> TYPE: PRT
<213> ORGANISM: Homo sapiens

<400> SEQUENCE: 13

Lys Ile Met Ala Gln Ile Leu Thr Val
1               5

<210> SEQ ID NO 14
<211> LENGTH: 9
<212> TYPE: PRT
<213> ORGANISM: Homo sapiens

<400> SEQUENCE: 14

Ala Leu Leu Thr Glu Thr Ile Phe Leu
1               5

<210> SEQ ID NO 15
<211> LENGTH: 9
<212> TYPE: PRT
<213> ORGANISM: Homo sapiens

<400> SEQUENCE: 15

Ile Leu Ile Lys His Leu Val Lys Val
1               5

<210> SEQ ID NO 16
<211> LENGTH: 9
<212> TYPE: PRT
<213> ORGANISM: Homo sapiens

<400> SEQUENCE: 16

Phe Met Pro Glu Glu Leu Pro Gln Leu
1               5
```

```
<210> SEQ ID NO 17
<211> LENGTH: 9
<212> TYPE: PRT
<213> ORGANISM: Homo sapiens

<400> SEQUENCE: 17

Ile Leu Ala Gln Gln Val His Ala Leu
1               5

<210> SEQ ID NO 18
<211> LENGTH: 9
<212> TYPE: PRT
<213> ORGANISM: Homo sapiens

<400> SEQUENCE: 18

Tyr Val Leu Asp Leu Ala Ala Lys Val
1               5

<210> SEQ ID NO 19
<211> LENGTH: 9
<212> TYPE: PRT
<213> ORGANISM: Homo sapiens

<400> SEQUENCE: 19

Leu Leu Asp Pro Gly Ser Leu Gln Leu
1               5

<210> SEQ ID NO 20
<211> LENGTH: 9
<212> TYPE: PRT
<213> ORGANISM: Homo sapiens

<400> SEQUENCE: 20

Ala Val Ala Asn Thr Thr Phe Thr Val
1               5

<210> SEQ ID NO 21
<211> LENGTH: 11
<212> TYPE: PRT
<213> ORGANISM: Homo sapiens

<400> SEQUENCE: 21

Arg Leu Ile Gln Gly Asp Gln Ile Leu Ser Val
1               5                   10

<210> SEQ ID NO 22
<211> LENGTH: 9
<212> TYPE: PRT
<213> ORGANISM: Homo sapiens

<400> SEQUENCE: 22

Phe Leu Ser Pro Pro Leu Pro Ser Val
1               5

<210> SEQ ID NO 23
<211> LENGTH: 9
<212> TYPE: PRT
<213> ORGANISM: Homo sapiens

<400> SEQUENCE: 23

Tyr Ile Gln Glu Val Val Gln Tyr Ile
1               5

<210> SEQ ID NO 24
<211> LENGTH: 9
```

```
<212> TYPE: PRT
<213> ORGANISM: Homo sapiens

<400> SEQUENCE: 24

Phe Thr Leu Gly Thr Thr Val Phe Leu
1               5

<210> SEQ ID NO 25
<211> LENGTH: 10
<212> TYPE: PRT
<213> ORGANISM: Homo sapiens

<400> SEQUENCE: 25

Leu Leu Val Pro Ala His Leu Val Ala Ala
1               5                   10

<210> SEQ ID NO 26
<211> LENGTH: 9
<212> TYPE: PRT
<213> ORGANISM: Homo sapiens

<400> SEQUENCE: 26

Ser Leu Met Glu Ile Leu Tyr Thr Leu
1               5

<210> SEQ ID NO 27
<211> LENGTH: 9
<212> TYPE: PRT
<213> ORGANISM: Homo sapiens

<400> SEQUENCE: 27

Ser Leu Ser Asp Leu Leu Val Ser Leu
1               5

<210> SEQ ID NO 28
<211> LENGTH: 9
<212> TYPE: PRT
<213> ORGANISM: Homo sapiens

<400> SEQUENCE: 28

Phe Ile Ala Asp Leu Val Val Gly Leu
1               5

<210> SEQ ID NO 29
<211> LENGTH: 9
<212> TYPE: PRT
<213> ORGANISM: Homo sapiens

<400> SEQUENCE: 29

Ile Leu Leu Asp Leu Glu Gln Ala Leu
1               5

<210> SEQ ID NO 30
<211> LENGTH: 9
<212> TYPE: PRT
<213> ORGANISM: Homo sapiens

<400> SEQUENCE: 30

Gln Leu Phe Tyr Thr Lys Ile Phe Leu
1               5

<210> SEQ ID NO 31
<211> LENGTH: 12
<212> TYPE: PRT
<213> ORGANISM: Homo sapiens
```

<400> SEQUENCE: 31

Val Leu Phe Gly Leu Asp Pro Ala Val Ile Lys Val
1               5                   10

<210> SEQ ID NO 32
<211> LENGTH: 11
<212> TYPE: PRT
<213> ORGANISM: Homo sapiens

<400> SEQUENCE: 32

Phe Leu Ala Gly Gly Ile Arg Gly Ser Gly Ala
1               5                   10

<210> SEQ ID NO 33
<211> LENGTH: 9
<212> TYPE: PRT
<213> ORGANISM: Homo sapiens

<400> SEQUENCE: 33

Phe Ile Ala Asp Val Val Glu Lys Ile
1               5

<210> SEQ ID NO 34
<211> LENGTH: 9
<212> TYPE: PRT
<213> ORGANISM: Homo sapiens

<400> SEQUENCE: 34

Glu Leu Asn Asn Gln Asn Phe Tyr Leu
1               5

<210> SEQ ID NO 35
<211> LENGTH: 9
<212> TYPE: PRT
<213> ORGANISM: Homo sapiens

<400> SEQUENCE: 35

Val Leu His Ser Leu Gln Thr Gln Leu
1               5

<210> SEQ ID NO 36
<211> LENGTH: 9
<212> TYPE: PRT
<213> ORGANISM: Homo sapiens

<400> SEQUENCE: 36

Ser Leu Phe Gly Lys Lys Tyr Ile Leu
1               5

<210> SEQ ID NO 37
<211> LENGTH: 9
<212> TYPE: PRT
<213> ORGANISM: Homo sapiens

<400> SEQUENCE: 37

Val Leu Ala Pro Val Ile Leu Met Leu
1               5

<210> SEQ ID NO 38
<211> LENGTH: 9
<212> TYPE: PRT
<213> ORGANISM: Homo sapiens

<400> SEQUENCE: 38

Val Leu Leu Asp Thr Ile Leu Gln Leu
1               5

<210> SEQ ID NO 39
<211> LENGTH: 10
<212> TYPE: PRT
<213> ORGANISM: Homo sapiens

<400> SEQUENCE: 39

Tyr Leu Leu Asn Leu Asn His Leu Gly Leu
1               5                   10

<210> SEQ ID NO 40
<211> LENGTH: 9
<212> TYPE: PRT
<213> ORGANISM: Homo sapiens

<400> SEQUENCE: 40

Tyr Ile Gln Glu His Leu Leu Gln Ile
1               5

<210> SEQ ID NO 41
<211> LENGTH: 9
<212> TYPE: PRT
<213> ORGANISM: Homo sapiens

<400> SEQUENCE: 41

Gly Leu Leu Lys Thr Leu Gln Lys Leu
1               5

<210> SEQ ID NO 42
<211> LENGTH: 10
<212> TYPE: PRT
<213> ORGANISM: Homo sapiens

<400> SEQUENCE: 42

Val Ile Leu Asp Thr Gly Thr Ile Gln Leu
1               5                   10

<210> SEQ ID NO 43
<211> LENGTH: 9
<212> TYPE: PRT
<213> ORGANISM: Homo sapiens

<400> SEQUENCE: 43

Tyr Leu Lys Asp Glu Leu Asp Glu Leu
1               5

<210> SEQ ID NO 44
<211> LENGTH: 9
<212> TYPE: PRT
<213> ORGANISM: Homo sapiens

<400> SEQUENCE: 44

Ala Leu Phe Ser Phe Val Thr Ala Leu
1               5

<210> SEQ ID NO 45
<211> LENGTH: 9
<212> TYPE: PRT
<213> ORGANISM: Homo sapiens

<400> SEQUENCE: 45

Ala Leu Leu Gly Ile Pro Leu Thr Leu

```
<210> SEQ ID NO 46
<211> LENGTH: 9
<212> TYPE: PRT
<213> ORGANISM: Homo sapiens

<400> SEQUENCE: 46

Gly Leu Ser Glu Val Leu Val Gln Ile
1               5

<210> SEQ ID NO 47
<211> LENGTH: 11
<212> TYPE: PRT
<213> ORGANISM: Homo sapiens

<400> SEQUENCE: 47

Thr Leu Ala Glu Val Arg Ala Val Gln Glu Ile
1               5                   10

<210> SEQ ID NO 48
<211> LENGTH: 9
<212> TYPE: PRT
<213> ORGANISM: Homo sapiens

<400> SEQUENCE: 48

Val Val Ala Ser Asn Ile Met Glu Val
1               5

<210> SEQ ID NO 49
<211> LENGTH: 9
<212> TYPE: PRT
<213> ORGANISM: Homo sapiens

<400> SEQUENCE: 49

Val Leu Ile Val Glu Val Pro Gly Val
1               5

<210> SEQ ID NO 50
<211> LENGTH: 9
<212> TYPE: PRT
<213> ORGANISM: Homo sapiens

<400> SEQUENCE: 50

Ser Leu Ser Asp His Ile Val Leu Leu
1               5

<210> SEQ ID NO 51
<211> LENGTH: 9
<212> TYPE: PRT
<213> ORGANISM: Homo sapiens

<400> SEQUENCE: 51

Asn Leu Trp Pro Met Ile Leu Thr Leu
1               5

<210> SEQ ID NO 52
<211> LENGTH: 9
<212> TYPE: PRT
<213> ORGANISM: Homo sapiens

<400> SEQUENCE: 52

Ser Ile Leu Asp Ala Val Gln Arg Val
1               5
```

```
<210> SEQ ID NO 53
<211> LENGTH: 9
<212> TYPE: PRT
<213> ORGANISM: Homo sapiens

<400> SEQUENCE: 53

Phe Leu Leu Glu Ile Arg Gln Thr Leu
1               5

<210> SEQ ID NO 54
<211> LENGTH: 10
<212> TYPE: PRT
<213> ORGANISM: Homo sapiens

<400> SEQUENCE: 54

Ala Leu Val Ala Lys Gly Leu Val Gln Ala
1               5                   10

<210> SEQ ID NO 55
<211> LENGTH: 9
<212> TYPE: PRT
<213> ORGANISM: Homo sapiens

<400> SEQUENCE: 55

Tyr Leu Ala Leu Ile Leu Pro Val Leu
1               5

<210> SEQ ID NO 56
<211> LENGTH: 9
<212> TYPE: PRT
<213> ORGANISM: Homo sapiens

<400> SEQUENCE: 56

Ile Leu Met Asp Phe Ser Asn Ser Met
1               5

<210> SEQ ID NO 57
<211> LENGTH: 9
<212> TYPE: PRT
<213> ORGANISM: Homo sapiens

<400> SEQUENCE: 57

Ser Leu Gln Lys Glu Ile Leu Tyr Leu
1               5

<210> SEQ ID NO 58
<211> LENGTH: 10
<212> TYPE: PRT
<213> ORGANISM: Homo sapiens

<400> SEQUENCE: 58

Phe Leu Val Asp Phe Glu Gln Ser His Leu
1               5                   10

<210> SEQ ID NO 59
<211> LENGTH: 9
<212> TYPE: PRT
<213> ORGANISM: Homo sapiens

<400> SEQUENCE: 59

Ser Leu Lys Asn Asn Val Val Ser Val
1               5

<210> SEQ ID NO 60
```

```
<211> LENGTH: 9
<212> TYPE: PRT
<213> ORGANISM: Homo sapiens

<400> SEQUENCE: 60

Ile Leu Trp Lys Asp Ile Glu Tyr Val
1               5

<210> SEQ ID NO 61
<211> LENGTH: 9
<212> TYPE: PRT
<213> ORGANISM: Homo sapiens

<400> SEQUENCE: 61

Ser Leu Met Gly Ile Leu Leu Arg Ile
1               5

<210> SEQ ID NO 62
<211> LENGTH: 11
<212> TYPE: PRT
<213> ORGANISM: Homo sapiens

<400> SEQUENCE: 62

Val Leu Ala Gly Pro Ala Phe Leu Val Gln Leu
1               5                   10

<210> SEQ ID NO 63
<211> LENGTH: 11
<212> TYPE: PRT
<213> ORGANISM: Homo sapiens

<400> SEQUENCE: 63

Gly Leu Ile Glu Asp His Phe Asp Val Thr Val
1               5                   10

<210> SEQ ID NO 64
<211> LENGTH: 9
<212> TYPE: PRT
<213> ORGANISM: Homo sapiens

<400> SEQUENCE: 64

Leu Leu Ala Ala Ser Val Ala Leu Ala
1               5

<210> SEQ ID NO 65
<211> LENGTH: 10
<212> TYPE: PRT
<213> ORGANISM: Homo sapiens

<400> SEQUENCE: 65

Ile Ile Tyr Gly Gly Ser Val Thr Gly Ala
1               5                   10

<210> SEQ ID NO 66
<211> LENGTH: 9
<212> TYPE: PRT
<213> ORGANISM: Homo sapiens

<400> SEQUENCE: 66

Thr Leu Leu Lys Thr Ile Ile Lys Val
1               5

<210> SEQ ID NO 67
<211> LENGTH: 9
<212> TYPE: PRT
```

```
<213> ORGANISM: Homo sapiens

<400> SEQUENCE: 67

Leu Leu Asp Val Leu Ala Pro Leu Val
1               5

<210> SEQ ID NO 68
<211> LENGTH: 9
<212> TYPE: PRT
<213> ORGANISM: Homo sapiens

<400> SEQUENCE: 68

Tyr Val Leu Thr Gln Pro Pro Ser Val
1               5

<210> SEQ ID NO 69
<211> LENGTH: 9
<212> TYPE: PRT
<213> ORGANISM: Homo sapiens

<400> SEQUENCE: 69

Ile Leu Ala Asp Leu Leu Pro Ser Leu
1               5

<210> SEQ ID NO 70
<211> LENGTH: 9
<212> TYPE: PRT
<213> ORGANISM: Homo sapiens

<400> SEQUENCE: 70

Ser Leu Thr Ala Leu Arg Leu Leu Leu
1               5

<210> SEQ ID NO 71
<211> LENGTH: 9
<212> TYPE: PRT
<213> ORGANISM: Homo sapiens

<400> SEQUENCE: 71

Ala Leu Asp Gly His Leu Tyr Ala Val
1               5

<210> SEQ ID NO 72
<211> LENGTH: 9
<212> TYPE: PRT
<213> ORGANISM: Homo sapiens

<400> SEQUENCE: 72

Tyr Ser Leu Glu Lys Val Phe Gly Ile
1               5

<210> SEQ ID NO 73
<211> LENGTH: 9
<212> TYPE: PRT
<213> ORGANISM: Homo sapiens

<400> SEQUENCE: 73

Gly Leu Asp Gly Ile Pro Phe Thr Val
1               5

<210> SEQ ID NO 74
<211> LENGTH: 9
<212> TYPE: PRT
<213> ORGANISM: Homo sapiens
```

<400> SEQUENCE: 74

Gly Leu Phe His Lys Gln Val Thr Val
1               5

<210> SEQ ID NO 75
<211> LENGTH: 9
<212> TYPE: PRT
<213> ORGANISM: Homo sapiens

<400> SEQUENCE: 75

Phe Leu Ile Lys Ser Ile Asn Leu Val
1               5

<210> SEQ ID NO 76
<211> LENGTH: 10
<212> TYPE: PRT
<213> ORGANISM: Homo sapiens

<400> SEQUENCE: 76

Val Leu Ala Asp Asp His Leu Ile Glu Val
1               5                   10

<210> SEQ ID NO 77
<211> LENGTH: 9
<212> TYPE: PRT
<213> ORGANISM: Homo sapiens

<400> SEQUENCE: 77

Ser Leu Ile Lys His Lys Ile Met Leu
1               5

<210> SEQ ID NO 78
<211> LENGTH: 9
<212> TYPE: PRT
<213> ORGANISM: Homo sapiens

<400> SEQUENCE: 78

Ala Leu Leu Asp Thr Val Val Gln Ala
1               5

<210> SEQ ID NO 79
<211> LENGTH: 9
<212> TYPE: PRT
<213> ORGANISM: Homo sapiens

<400> SEQUENCE: 79

Ala Leu Ala Asp Ile Val Trp Arg Ala
1               5

<210> SEQ ID NO 80
<211> LENGTH: 9
<212> TYPE: PRT
<213> ORGANISM: Homo sapiens

<400> SEQUENCE: 80

Lys Leu Ala Ser Met Leu Glu Thr Leu
1               5

<210> SEQ ID NO 81
<211> LENGTH: 9
<212> TYPE: PRT
<213> ORGANISM: Homo sapiens

<400> SEQUENCE: 81

Ser Leu Leu Pro Ala Leu Pro Lys Leu
1               5

<210> SEQ ID NO 82
<211> LENGTH: 11
<212> TYPE: PRT
<213> ORGANISM: Homo sapiens

<400> SEQUENCE: 82

Ser Leu Leu Gln Ala Thr Asp Phe Met Ser Leu
1               5                   10

<210> SEQ ID NO 83
<211> LENGTH: 9
<212> TYPE: PRT
<213> ORGANISM: Homo sapiens

<400> SEQUENCE: 83

Ile Gln Trp Ser Ile Val Pro Glu Val
1               5

<210> SEQ ID NO 84
<211> LENGTH: 9
<212> TYPE: PRT
<213> ORGANISM: Homo sapiens

<400> SEQUENCE: 84

Tyr Leu Met Asp Glu Gly Ala His Leu
1               5

<210> SEQ ID NO 85
<211> LENGTH: 9
<212> TYPE: PRT
<213> ORGANISM: Homo sapiens

<400> SEQUENCE: 85

Phe Val Met Ser Glu Ile Arg Thr Val
1               5

<210> SEQ ID NO 86
<211> LENGTH: 10
<212> TYPE: PRT
<213> ORGANISM: Homo sapiens

<400> SEQUENCE: 86

Gly Leu Leu Gln Gly Lys Leu Ala Leu Leu
1               5                   10

<210> SEQ ID NO 87
<211> LENGTH: 8
<212> TYPE: PRT
<213> ORGANISM: Homo sapiens

<400> SEQUENCE: 87

Leu Ala Asp Gly Val Gln Lys Val
1               5

<210> SEQ ID NO 88
<211> LENGTH: 9
<212> TYPE: PRT
<213> ORGANISM: Homo sapiens

<400> SEQUENCE: 88

Thr Leu Ala Glu Leu His Ile Ser Leu
1               5

```
<210> SEQ ID NO 89
<211> LENGTH: 9
<212> TYPE: PRT
<213> ORGANISM: Homo sapiens

<400> SEQUENCE: 89

Ser Leu Leu Leu Ala Val Thr Glu Val
1               5

<210> SEQ ID NO 90
<211> LENGTH: 9
<212> TYPE: PRT
<213> ORGANISM: Homo sapiens

<400> SEQUENCE: 90

Phe Thr Leu Glu Lys Asn Phe Val Ile
1               5

<210> SEQ ID NO 91
<211> LENGTH: 9
<212> TYPE: PRT
<213> ORGANISM: Homo sapiens

<400> SEQUENCE: 91

Met Leu Leu Ser Ser Leu Val Ser Leu
1               5

<210> SEQ ID NO 92
<211> LENGTH: 9
<212> TYPE: PRT
<213> ORGANISM: Homo sapiens

<400> SEQUENCE: 92

Phe Leu Phe Arg Asp Ile Leu Glu Leu
1               5

<210> SEQ ID NO 93
<211> LENGTH: 10
<212> TYPE: PRT
<213> ORGANISM: Homo sapiens

<400> SEQUENCE: 93

Gly Val Met Ala Gly Asp Ile Tyr Ser Val
1               5                   10

<210> SEQ ID NO 94
<211> LENGTH: 9
<212> TYPE: PRT
<213> ORGANISM: Homo sapiens

<400> SEQUENCE: 94

Ile Leu His His Lys Val Tyr Asp Leu
1               5

<210> SEQ ID NO 95
<211> LENGTH: 10
<212> TYPE: PRT
<213> ORGANISM: Homo sapiens

<400> SEQUENCE: 95

Lys Leu Thr Asp Val Gly Ile Ala Thr Leu
1               5                   10
```

-continued

<210> SEQ ID NO 96
<211> LENGTH: 9
<212> TYPE: PRT
<213> ORGANISM: Homo sapiens

<400> SEQUENCE: 96

Thr Leu Ala Glu Thr Leu Val Asn Leu
1               5

<210> SEQ ID NO 97
<211> LENGTH: 9
<212> TYPE: PRT
<213> ORGANISM: Homo sapiens

<400> SEQUENCE: 97

Thr Leu Ile Ser Glu Leu Val Gln Ala
1               5

<210> SEQ ID NO 98
<211> LENGTH: 9
<212> TYPE: PRT
<213> ORGANISM: Homo sapiens

<400> SEQUENCE: 98

Lys Ile Pro Pro Val Ser Pro Ser Ile
1               5

<210> SEQ ID NO 99
<211> LENGTH: 9
<212> TYPE: PRT
<213> ORGANISM: Homo sapiens

<400> SEQUENCE: 99

Gly Leu Ala Pro His Leu Glu Gln Ile
1               5

<210> SEQ ID NO 100
<211> LENGTH: 9
<212> TYPE: PRT
<213> ORGANISM: Homo sapiens

<400> SEQUENCE: 100

Lys Leu Asn Val Ala Pro Leu Ala Val
1               5

<210> SEQ ID NO 101
<211> LENGTH: 10
<212> TYPE: PRT
<213> ORGANISM: Homo sapiens

<400> SEQUENCE: 101

His Ile Tyr Asp Lys Ala Phe Ile Thr Val
1               5                   10

<210> SEQ ID NO 102
<211> LENGTH: 9
<212> TYPE: PRT
<213> ORGANISM: Homo sapiens

<400> SEQUENCE: 102

Leu Leu Phe Asp Val His Thr Thr Leu
1               5

<210> SEQ ID NO 103
<211> LENGTH: 9

-continued

<212> TYPE: PRT
<213> ORGANISM: Homo sapiens

<400> SEQUENCE: 103

Lys Leu Gln Asp Gly Leu Leu His Ile
1               5

<210> SEQ ID NO 104
<211> LENGTH: 10
<212> TYPE: PRT
<213> ORGANISM: Homo sapiens

<400> SEQUENCE: 104

Ala Leu Phe Glu Gly Val Val Arg Gln Ile
1               5                   10

<210> SEQ ID NO 105
<211> LENGTH: 12
<212> TYPE: PRT
<213> ORGANISM: Homo sapiens

<400> SEQUENCE: 105

Ala Leu Ala Asp Leu Asp Glu Leu Leu Ile Arg Ala
1               5                   10

<210> SEQ ID NO 106
<211> LENGTH: 9
<212> TYPE: PRT
<213> ORGANISM: Homo sapiens

<400> SEQUENCE: 106

Val Leu Met Asp Leu Lys Ala Leu Leu
1               5

<210> SEQ ID NO 107
<211> LENGTH: 10
<212> TYPE: PRT
<213> ORGANISM: Homo sapiens

<400> SEQUENCE: 107

Val Leu Met Asp Leu Lys Ala Leu Leu Leu
1               5                   10

<210> SEQ ID NO 108
<211> LENGTH: 9
<212> TYPE: PRT
<213> ORGANISM: Homo sapiens

<400> SEQUENCE: 108

Val Leu Ile Ser Val Leu Gln Ala Ile
1               5

<210> SEQ ID NO 109
<211> LENGTH: 9
<212> TYPE: PRT
<213> ORGANISM: Homo sapiens

<400> SEQUENCE: 109

Tyr Leu Trp Ser Arg Val Glu Lys Leu
1               5

<210> SEQ ID NO 110
<211> LENGTH: 9
<212> TYPE: PRT
<213> ORGANISM: Homo sapiens

```
<400> SEQUENCE: 110

Leu Leu Asp Leu His Ser Tyr Leu Leu
1               5

<210> SEQ ID NO 111
<211> LENGTH: 9
<212> TYPE: PRT
<213> ORGANISM: Homo sapiens

<400> SEQUENCE: 111

Thr Leu Leu Glu Thr Glu Met Leu Leu
1               5

<210> SEQ ID NO 112
<211> LENGTH: 11
<212> TYPE: PRT
<213> ORGANISM: Homo sapiens

<400> SEQUENCE: 112

Leu Leu Phe Asp His Leu Glu Pro Ile Glu Leu
1               5                   10

<210> SEQ ID NO 113
<211> LENGTH: 9
<212> TYPE: PRT
<213> ORGANISM: Homo sapiens

<400> SEQUENCE: 113

Ser Leu Phe Asp Trp Asn Val Lys Leu
1               5

<210> SEQ ID NO 114
<211> LENGTH: 9
<212> TYPE: PRT
<213> ORGANISM: Homo sapiens

<400> SEQUENCE: 114

Ala Leu Ala Val Asn Ile Ser Ala Ala
1               5

<210> SEQ ID NO 115
<211> LENGTH: 9
<212> TYPE: PRT
<213> ORGANISM: Homo sapiens

<400> SEQUENCE: 115

Leu Leu Asp Pro Lys Thr Ile Phe Leu
1               5

<210> SEQ ID NO 116
<211> LENGTH: 9
<212> TYPE: PRT
<213> ORGANISM: Homo sapiens

<400> SEQUENCE: 116

Gly Leu Val Asp Ile Met Val His Leu
1               5

<210> SEQ ID NO 117
<211> LENGTH: 9
<212> TYPE: PRT
<213> ORGANISM: Homo sapiens

<400> SEQUENCE: 117
```

Val Leu Phe Gly Glu Leu Pro Ala Leu
1               5

<210> SEQ ID NO 118
<211> LENGTH: 9
<212> TYPE: PRT
<213> ORGANISM: Homo sapiens

<400> SEQUENCE: 118

Phe Leu Asn Ala Ile Glu Thr Ala Leu
1               5

<210> SEQ ID NO 119
<211> LENGTH: 9
<212> TYPE: PRT
<213> ORGANISM: Homo sapiens

<400> SEQUENCE: 119

Arg Leu His Asp Glu Asn Ile Leu Leu
1               5

<210> SEQ ID NO 120
<211> LENGTH: 9
<212> TYPE: PRT
<213> ORGANISM: Homo sapiens

<400> SEQUENCE: 120

Gly Leu Ala Gly Asp Asn Ile Tyr Leu
1               5

<210> SEQ ID NO 121
<211> LENGTH: 9
<212> TYPE: PRT
<213> ORGANISM: Homo sapiens

<400> SEQUENCE: 121

Ala Leu Leu Arg Thr Val Val Ser Val
1               5

<210> SEQ ID NO 122
<211> LENGTH: 9
<212> TYPE: PRT
<213> ORGANISM: Homo sapiens

<400> SEQUENCE: 122

Ser Leu Asp Pro Ser Ser Pro Gln Val
1               5

<210> SEQ ID NO 123
<211> LENGTH: 9
<212> TYPE: PRT
<213> ORGANISM: Homo sapiens

<400> SEQUENCE: 123

Tyr Val Asp Pro Val Ile Thr Ser Ile
1               5

<210> SEQ ID NO 124
<211> LENGTH: 9
<212> TYPE: PRT
<213> ORGANISM: Homo sapiens

<400> SEQUENCE: 124

Ile Leu Ser Pro Leu Ser Val Ala Leu

<210> SEQ ID NO 125
<211> LENGTH: 9
<212> TYPE: PRT
<213> ORGANISM: Homo sapiens

<400> SEQUENCE: 125

Lys Leu Asp Pro Thr Lys Thr Thr Leu
1               5

<210> SEQ ID NO 126
<211> LENGTH: 9
<212> TYPE: PRT
<213> ORGANISM: Homo sapiens

<400> SEQUENCE: 126

Lys Ile Gln Glu Ile Leu Thr Gln Val
1               5

<210> SEQ ID NO 127
<211> LENGTH: 9
<212> TYPE: PRT
<213> ORGANISM: Homo sapiens

<400> SEQUENCE: 127

Val Leu Ala Pro Leu Phe Val Tyr Leu
1               5

<210> SEQ ID NO 128
<211> LENGTH: 9
<212> TYPE: PRT
<213> ORGANISM: Homo sapiens

<400> SEQUENCE: 128

Tyr Leu Glu Glu Asp Val Tyr Gln Leu
1               5

<210> SEQ ID NO 129
<211> LENGTH: 9
<212> TYPE: PRT
<213> ORGANISM: Homo sapiens

<400> SEQUENCE: 129

Val Leu Ala Pro Arg Val Leu Arg Ala
1               5

<210> SEQ ID NO 130
<211> LENGTH: 9
<212> TYPE: PRT
<213> ORGANISM: Homo sapiens

<400> SEQUENCE: 130

Ala Leu Pro Thr Val Leu Val Gly Val
1               5

<210> SEQ ID NO 131
<211> LENGTH: 9
<212> TYPE: PRT
<213> ORGANISM: Homo sapiens

<400> SEQUENCE: 131

Val Met Ala Gly Asp Ile Tyr Ser Val
1               5

```
<210> SEQ ID NO 132
<211> LENGTH: 9
<212> TYPE: PRT
<213> ORGANISM: Homo sapiens

<400> SEQUENCE: 132

Ser Val Ala Ser Thr Ile Thr Gly Val
1               5

<210> SEQ ID NO 133
<211> LENGTH: 9
<212> TYPE: PRT
<213> ORGANISM: Homo sapiens

<400> SEQUENCE: 133

Gln Leu Ile Asp Tyr Glu Arg Gln Leu
1               5

<210> SEQ ID NO 134
<211> LENGTH: 8
<212> TYPE: PRT
<213> ORGANISM: Homo sapiens

<400> SEQUENCE: 134

Val Ala Asp Lys Ile His Ser Val
1               5

<210> SEQ ID NO 135
<211> LENGTH: 9
<212> TYPE: PRT
<213> ORGANISM: Homo sapiens

<400> SEQUENCE: 135

Val Val Asp Glu Gly Pro Thr Gly Val
1               5

<210> SEQ ID NO 136
<211> LENGTH: 9
<212> TYPE: PRT
<213> ORGANISM: Homo sapiens

<400> SEQUENCE: 136

Tyr Gln Asp Pro His Ser Thr Ala Val
1               5

<210> SEQ ID NO 137
<211> LENGTH: 9
<212> TYPE: PRT
<213> ORGANISM: Homo sapiens

<400> SEQUENCE: 137

Thr Leu Val Ala Ile Val Val Gly Val
1               5

<210> SEQ ID NO 138
<211> LENGTH: 9
<212> TYPE: PRT
<213> ORGANISM: Homo sapiens

<400> SEQUENCE: 138

Ser Leu Asp Thr Leu Met Thr Tyr Val
1               5

<210> SEQ ID NO 139
```

```
<211> LENGTH: 10
<212> TYPE: PRT
<213> ORGANISM: Homo sapiens

<400> SEQUENCE: 139

Ile Leu Asn Val Asp Gly Leu Ile Gly Val
1               5                   10

<210> SEQ ID NO 140
<211> LENGTH: 9
<212> TYPE: PRT
<213> ORGANISM: Homo sapiens

<400> SEQUENCE: 140

Ser Leu Ala Asn Asn Val Thr Ser Val
1               5

<210> SEQ ID NO 141
<211> LENGTH: 11
<212> TYPE: PRT
<213> ORGANISM: Homo sapiens

<400> SEQUENCE: 141

Leu Leu Val Asp Asp Ser Phe Leu His Thr Val
1               5                   10

<210> SEQ ID NO 142
<211> LENGTH: 9
<212> TYPE: PRT
<213> ORGANISM: Homo sapiens

<400> SEQUENCE: 142

Ser Val Asp Val Ser Pro Pro Lys Val
1               5

<210> SEQ ID NO 143
<211> LENGTH: 10
<212> TYPE: PRT
<213> ORGANISM: Homo sapiens

<400> SEQUENCE: 143

Ala Leu Phe Val Arg Leu Leu Ala Leu Ala
1               5                   10

<210> SEQ ID NO 144
<211> LENGTH: 10
<212> TYPE: PRT
<213> ORGANISM: Homo sapiens

<400> SEQUENCE: 144

Arg Leu Leu Asp Val Leu Ala Pro Leu Val
1               5                   10

<210> SEQ ID NO 145
<211> LENGTH: 9
<212> TYPE: PRT
<213> ORGANISM: Homo sapiens

<400> SEQUENCE: 145

Ser Leu His Phe Leu Ile Leu Tyr Val
1               5

<210> SEQ ID NO 146
<211> LENGTH: 11
<212> TYPE: PRT
```

```
<213> ORGANISM: Homo sapiens

<400> SEQUENCE: 146

Lys Leu Ile Asp Leu Ser Gln Val Met Tyr Leu
1               5                   10

<210> SEQ ID NO 147
<211> LENGTH: 11
<212> TYPE: PRT
<213> ORGANISM: Homo sapiens

<400> SEQUENCE: 147

Ala Leu Ala Asp Lys Glu Leu Leu Pro Ser Val
1               5                   10

<210> SEQ ID NO 148
<211> LENGTH: 9
<212> TYPE: PRT
<213> ORGANISM: Homo sapiens

<400> SEQUENCE: 148

Lys Leu Leu Thr Glu Val His Ala Ala
1               5

<210> SEQ ID NO 149
<211> LENGTH: 12
<212> TYPE: PRT
<213> ORGANISM: Homo sapiens

<400> SEQUENCE: 149

Ser Ile Leu Thr Ile Glu Asp Gly Ile Phe Glu Val
1               5                   10

<210> SEQ ID NO 150
<211> LENGTH: 9
<212> TYPE: PRT
<213> ORGANISM: Homo sapiens

<400> SEQUENCE: 150

Thr Leu Met Pro Asn Ile Asn Lys Leu
1               5

<210> SEQ ID NO 151
<211> LENGTH: 10
<212> TYPE: PRT
<213> ORGANISM: Homo sapiens

<400> SEQUENCE: 151

Tyr Met Tyr Glu Gly Pro Ala Pro Arg Ile
1               5                   10

<210> SEQ ID NO 152
<211> LENGTH: 10
<212> TYPE: PRT
<213> ORGANISM: Homo sapiens

<400> SEQUENCE: 152

Glu Leu Ala Gly Ile Gly Ile Leu Thr Val
1               5                   10
```

```
<210> SEQ ID NO 153
<211> LENGTH: 9
<212> TYPE: PRT
<213> ORGANISM: Homo sapiens

<400> SEQUENCE: 153

Tyr Leu Leu Pro Ala Ile Val His Ile
1               5
```